United States Patent
Beswick et al.

(10) Patent No.: US 7,091,237 B2
(45) Date of Patent: Aug. 15, 2006

(54) FURAN AND THIOPHENE DERIVATIVES THAT ACTIVATE HUMAN PEROXISOME PROLIFERATOR ACTIVATED RECEPTORS

(75) Inventors: Paul John Beswick, Stevenage (GB); Christopher Charles Hamlett, Stevenage (GB); Vipulkumar Patel, Stevenage (GB); Michael Lawrence Sierra, Les Ulis (FR); Nigel Grahame Ramsden, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 196 days.

(21) Appl. No.: 10/476,194

(22) PCT Filed: May 9, 2002

(86) PCT No.: PCT/GB02/02152

§ 371 (c)(1),
(2), (4) Date: Mar. 23, 2004

(87) PCT Pub. No.: WO02/092590

PCT Pub. Date: Nov. 21, 2002

(65) Prior Publication Data

US 2004/0157890 A1    Aug. 12, 2004

(30) Foreign Application Priority Data

May 11, 2001  (GB) .................................. 0111523.7

(51) Int. Cl.
*A61K 31/38*    (2006.01)
*A61K 31/34*    (2006.01)
*C07D 333/24*   (2006.01)
*C07D 307/02*   (2006.01)

(52) U.S. Cl. ..................... 514/438; 514/461; 549/79; 549/499

(58) Field of Classification Search ................ 514/438, 514/461; 549/79, 499
See application file for complete search history.

(56) References Cited

FOREIGN PATENT DOCUMENTS

| WO | WO 00 08002 | 2/2000 |
|---|---|---|
| WO | WO 00 64888 | 11/2000 |

*Primary Examiner*—Deborah C. Lambkin
(74) *Attorney, Agent, or Firm*—Jennifer L. Fox

(57) ABSTRACT

A compound of formula (I) or pharmaceutically acceptable salts and solvates thereof, for the treatment of a hPPAR mediated disease or condition (I)

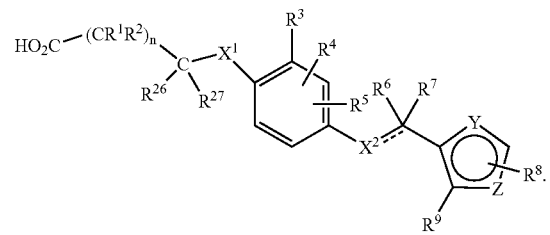

22 Claims, No Drawings

FURAN AND THIOPHENE DERIVATIVES THAT ACTIVATE HUMAN PEROXISOME PROLIFERATOR ACTIVATED RECEPTORS

This application is filed pursuant to 35 U.S.C. § 371 as a United States National Phase Application of International Application No. PCT/GB02/02152 filed May 9, 2002, which claims priority from 0111523.7 filed May 11, 2001.

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. *Curr. Pharm. Des.* 1998, 4, 53–70).

Syndrome X (including metabolic syndrome) is loosely defined as a collection of abnormalities including hyperinsulemia, obesity, elevated levels of trigycerides, uric acid, fibrinogen, small dense LDL particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are ophan receptors belonging to the steroid/retinoid receptor superfamily of ligand-activated transcription factors. See, for example Willson T. M. and Wahli, W., *Curr. Opin. Chem. Biol.* (1997) Vol 1 pp 235–241 and Willson T. M. et. al., *J. Med. Chem* (2000) Vol 43 p 527–549. The binding of agonist ligands to the receptor results in changes in the expression level of MRNA's encided by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endocrin. Metab* 291–296, 4 (1993)).

It has now been reported that thiazolidinediones are potent and selective activators of PPAR-gamma and bind directly to the PPAR-gamma receptor (J. M. Lehmann et. al., *J. Biol. Chem.* 12953–12956, 270 (1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., *Curr. Opin. Endocrnol. Diabetes*, 90–96, 5 (2), (1998); M. D. Johnson et al., *Ann. Pharmacother.*, 337–348, 32 (3), (1997); and M. Leutenegger et al., *Curr. Ther. Res.*, 403–416, 58 (7), (1997).

The mechanism for this triglyceride lowering effect appears to be predominantly increased clearance of very low density lipoproteins (VLDL) through induction of liporotein lipase (LPL) gene expression. See, for example, B. Staels et al., *Arterioscler. Thromb., Vasc. Biol.*, 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., *Curr. Pharm. Des.*, 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., *Atherosclerosis*, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. Nos. 5,847,008 (Doebber et al.) and U.S. Pat. No. 5,859,051 (Adams et al.) and PCT publications WO 97/28149 (Leibowitz et al.) and WO99/04815 (Shimokawa et al.). In a recent report (Berger et al., *J. Biol. Chem.* 1999), vol. 274, pp. 6718–6725) it was stated that PPARδ activation does not appear to modulate glucose or triglyceride levels.

Accordingly, the present invention provides a compound of formula (I) and pharmaceutically acceptable salts, hydrolysable esters and solvates thereof;

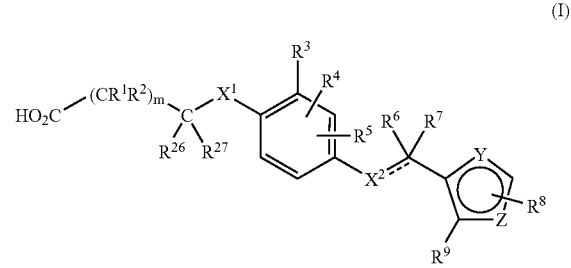

wherein
$X^1$ is O, S, NH or $NCH_3$, $C_{1-3}$ alkyl.
$R^1$ and $R^2$ are independently H or $C_{1-3}$ alkyl.
$R^3$, $R^4$ and $R^5$ are independently H, $CH_3$, $OCH_3$, $CF_3$ or halogen;
$R^{26}$ and $R^{27}$ are independently H. $C_{1-3}$ alkyl or an $R^{26}$ and $R^{27}$ may, together with the carbon atom to which they are bonded form a 3–5 membered cycloalkyl ring;
m is 0–3;

$X^2$ is $(CR^{10}R^{11})_n$, O, S, $OCH_2$;

n=1 or 2;

$R^6$, $R^7$, $R^{10}$ and $R^{11}$ independently represent H, F, $C_{1-6}$alkyl, phenyl or allyl or form a double bond as indicated by the depicted dashed line;

one of Y and Z is CH, the other is S or O with the proviso that Y cannot be substituted and Z can only be substituted when it is carbon.

$R^8$ is phenyl or pyridyl (wherein the N is in position 2 or 3) either of which may optionally be substituted by one or more halogen, $CF_3$, $OCF_3$, $C_{1-6}$ straight or branched alkyl with the provision that when $R^3$ is pyridyl, the N is unsubstituted.

$R^9$ is $C_{1-6}$alkyl, $CF_3$ or —$CH_2D$, wherein D is selected from:

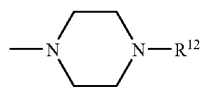

A wherein
$R^{12}$ is selected from the group consisting of moieties depicted below.

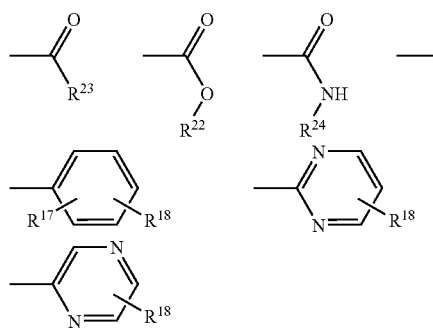

$R^{17}$ and $R^{18}$ are independently hydrogen $C_{1-6}$alkyl, $C_{1-6}$perfluoroalkyl, $C_{1-6}$acyl, —$OC_{1-6}$alkyl, perfluoroO$C_{1-6}$alkyl, or 1-hydroxy$C_{1-6}$alkyl;

$R^{19}$ is $C_{1-6}$alkyl;

$R^{22}$ is $C_{1-6}$alkyl, 5-membered aryl, 5-membered heteroaryl, —$C_{1-6}$alkylenearyl;

$R^{23}$ is $C_{1-6}$alkyl, $C_{3-6}$cycloalkyl, 6-membered aryl or a 5-membered heteroaryl optionally substituted with one or two substituents selected from perfluro$C_{1-6}$alkyl, perfluroO$C_{1-6}$alkyl, $C_{1-6}$alkyl, —$OC_{1-6}$alkyl and —$SC_{1-6}$alkyl; and.

$R^{24}$ is $C_{1-6}$alkyl, —$C_{1-6}$alkylenearyl$C_{1-6}$alkylaryl, or a 6-membered aryl optionally substituted with one or two substituents selected from perfluro$C_{1-6}$alkyl, perfluroO$C_{1-6}$alkyl, $C_{1-6}$alkyl, —$OC_{1-6}$alkyl, and —$SC_{1-6}$alkyl;

B

where Z is O, N or S (note that when Z is N, the depicted bond can be attached to the nitrogen in the ring as well as any of the carbons in the ring);

C

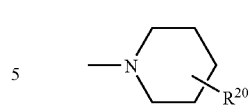

$R^{20}$ is $C_{1-6}$alkyl, 6 membered aryl, —$OC_{1-6}$alkyl, hydroxy or 1-alkoxy $C_{1-6}$alkyl.

D

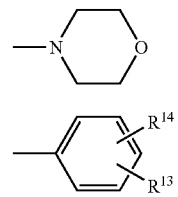

E where $R^{13}$ and $R^{14}$ are independently halogen, a 6-membered aryl or a 5-membered heteroaryl optionally substituted with one or two substituents selected from perfluro$C_{1-6}$alkyl, perfluroO$C_{1-6}$alkyl, $C_{1-6}$-alkyl, —$OC_{1-6}$alkyl, and —$SC_{1-6}$alkyl;

F

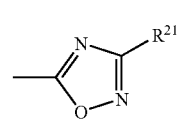

$R^{21}$ is $C_{1-3}$alkyl, —$C_{1-6}$alkylenephenyl, 6 membered aryl, each optionally substituted with one or two substituents selected from CN, halogen 5 or 6 membered heteroaryl, bicyclic aryl or bicyclic heteroaryl, perfluro$C_{1-6}$alkyl, perfluroO$C_{1-6}$alkyl, $C_{1-6}$alkyl, —$OC_{1-6}$alkyl and —$SC_{1-6}$alkyl.

G

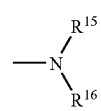

$R^{15}$ and $R^{16}$ are independently $C_{1-6}$alkyl, $C_{3-6}$cycloalkyl, $C_{0-6}$alkylene 6-membered aryl optionally substituted with 1 or 2 $C_{1-3}$alkyl or alkoxy groups, $C_{0-6}$alkylene 5-membered heteroaryl, pyridyl, bicyclic aryl or bicyclic heteroaryl or $R^{12}$ as defined above.

H

I

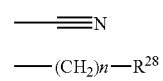

wherein n is 1–3, $R^{28}$ is 6 membered aryl, 5 or 6 membered heteroaryl or bicyclic aryl or bicyclic heteroaryl.

J

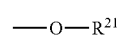

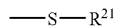

K wherein $R^{21}$ is defined above.

As used herein, "aryl" or any phrase or term including aryl such as "$C_{1-6}$alkylenearyl", the "aryl" means a phenyl group or a 5 or 6 membered heteroaryl group. As used herein the term "heteroaryl" means a 5 or 6 membered heteroaryl group.

As used herein any such "aryl" or "heteroaryl" group may optionally be substituted with one or two substituents selected from the group consisting of halogen, CN, dimethylamino, perfluro$C_{1-6}$alkyl, perfluroO$C_{1-6}$alkyl, $C_{1-6}$alkyl, —O$C_{1-6}$alkyl, —$C_{1-6}$alkyleneO$C_{1-6}$alkyl, and —S$C_{1-6}$alkyl.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable hydrolysable ester or, solvate, thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $R^{26}$ and $R^{27}$ are independently H or $CH_3$. More preferably $R^1$ and $R^2$ are H.

Preferably m is 0

Preferably $X^1$ is O, S, NH, $NCH_3$. More preferably $X^1$ is O or S.

Preferably $X^2$ is $(CR^{10}R^{11})_n$, O or S and where n is preferably 1.

Preferably $R^6$, $R^7$, $R^{10}$ and $R^{11}$ are H.

Preferably $R^8$ is phenyl, optionally substituted by 1, 2, 3, 4 or 5 substituents independently selected from $CH_3$, $OCH_3$, $CF_3$ or halogen.

Preferably $R^8$ whether phenyl or pyridyl is mono or disubstituted. When disubstituted preferably one of the substituents is halogen, more preferably one is halogen and the other is $CF_3$.

More preferably $R^8$ whether phenyl or pyridyl is monosubstituted. When monosubstituted, preferably the substituent is in the para position on the ring and is most preferably $CF_3$.

Preferably $R^3$ is H, $CH_3$ or $CF_3$. More preferably, $R^3$ is $CH_3$.

Preferably $R^4$ and $R^5$ are both H.

Preferably $R^9$ is $C_{1-6}$-alkyl, $CF_3$ or $CH_2D$ wherein D is selected from moieties G, H, I, J and K.

When D represents moiety 1, preferably n is 1 or 2 and $R^{28}$ is pyridyl or optionally substituted phenyl.

When D represents moiety J or K, preferably $R^{21}$ is $C_{1-3}$alkyl, $C_{1-6}$alkylenephenyl, a bicyclic heteroaryl group or a 5 or 6 membered heteroaryl group.

When D represents moiety G. $R^{15}$ and $R^{16}$ preferably independently represent:

$C_{1-6}$-alkyl, $C_{3-6}$cycloalkyl, phenyl, —$C_{1-6}$alkylenephenyl (optionally substituted), —$C_{1-6}$-alkylenepyridyl.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ? in the binding assay described below, and which achieve at least 50% activation of the relevant PPAR relative to the appropriate indicated positive control in the transfection assay described below at concentrations of $10^{-5}$ M or less. More preferably, the compounds of this invention achieve 50% activation of at least one human PPAR in the relevant transfection assay at concentrations of $10^{-6}$ M or less. More preferably the compounds of the invention achieve 50% activation of at least one human PPAR in the relevant transfection assay at concentrations of $10^{-7}$M or less.

Preferred compounds of the invention include
{4-[({3-ethyl-5-[4-(trifluoromethyl)phenyl]thien-2-yl}methyl)thio]-2-methylphenoxy}acetic acid
[4-({[5-(4-chlorophenyl)-2-(trifluoromethyl)-3-furyl]methyl}thio)-2-methylphenoxy]acetic acid
[2-methyl-4-({3-methyl-5-[4-(trifluoromethyl)phenyl]thien-2-yl}methoxy)phenoxy]acetic acid {2-methyl-4-[({3-methyl-5-[4-(trifluoromethyl)phenyl]thien-2-yl}methyl)thio]phenoxy}acetic acid
{2-methyl-4-[({2-methyl-5-[4-(trifluoromethyl)phenyl]-3-furyl}methyl)thio]phenoxy}acetic acid
{2-ethyl-4-[({2-methyl-5-[4-(trifluoromethyl)phenyl]-3-furyl}methyl)thio]phenoxy}acetic acid
{2-isopropyl-4-[({2-methyl-5-[4-(trifluoromethyl)phenyl]-3-furyl}methyl)thio]phenoxy}acetic acid
[2-methyl-4-({3-methyl-5-[4-(trifluoromethoxy)phenyl]thien-2-yl}methoxy)phenoxy]acetic acid
{4-[({2-[(benzylthio)methyl]-5-[4-(trifluoromethyl)phenyl]-3-furyl}methyl)thio]-2-methylphenoxy}acetic acid
{2-methyl-4-[({3-methyl-5-[4-(trifluoromethyl)phenyl]-2-furyl}methyl)thio]phenoxy}acetic acid
{2-methyl-4-[({3-methyl-4-[4-(trifluoromethyl)phenyl]thien-2-yl}methyl)thio]phenoxy}acetic acid
[4-({[5-(4-chlorophenyl)-2-methyl-3-furyl]methyl}thio)-2-methylphenoxy]acetic acid
{2-methyl-4-[({2-(trifluoromethyl)-5-[4-(trifluoromethyl)phenyl]-3-furyl}methyl)thio]phenoxy}acetic acid
[2-methyl-4-(2-{4-methyl-2-[4-(trifluoromethyl)phenyl]-1,3-thiazol-5-yl}ethyl)phenoxy]acetic acid
[2-methyl-4-(2-{3-methyl-5-[4-(trifluoromethyl)phenyl]thien-2-yl}ethyl)phenoxy]acetic acid
(4-{2-[5-(4-chlorophenyl)-2-(trifluoromethyl)-3-furyl]ethyl}-2-methylphenoxy)acetic acid
3-[4-({3-methyl-5-[4-(trifluoromethyl)phenyl]thien-2-yl}methoxy)phenyl]propanoic acid
{2-methyl-4-[({3-(phenoxymethyl)-5-[4-(trifluoromethyl)phenyl]thien-2-yl}methyl)thio]phenoxy}acetic acid
3-[2-methyl-4-({3-methyl-5-[4-(trifluoromethyl)phenyl]thien-2-yl}methoxy)phenyl]propanoic acid
{4-[({2-[(benzylthio)methyl]-5-[4-(trifluoromethyl)phenyl]-3-furyl}methyl)thio]-2-methylphenoxy}acetic acid
{4-[({2-[(isopropylthio)methyl]-5-[4-(trifluoromethyl)phenyl]-3-furyl}methyl)thio]-2-methylphenoxy}acetic acid
{2-methyl-4-[({2-{[methyl(phenyl)amino]methyl}-5-[4-(trifluoromethyl)phenyl]-3-furyl}methyl)thio]phenoxy}acetic acid
[2-methyl-4-(2-{2-methyl-5-[4-(trifluoromethyl)phenyl]-3-furyl}ethyl)phenoxy]acetic acid
3-[2-methyl-4-(2-{3-methyl-5-[4-(trifluoromethyl)phenyl]thien-2-yl}ethyl)phenyl]propanoic acid
[2-methyl-4-({2-methyl-5-[4-(trifluoromethyl)phenyl]thien-3-yl}methoxy)phenoxy]acetic acid
{4-[({2-isopentyl-5-[4-(trifluoromethyl)phenyl]-3-furyl}methyl)thio]-2-methylphenoxy}acetic acid
{2-methyl-4-[({2-methyl-5-[4-(trifluoromethyl)phenyl]thien-3-yl}methyl)thio]phenoxy}acetic acid
[4-[({2-methyl-5-[4-(trifluoromethyl)phenyl]-3-furyl}methyl)thio]-2-(trifluoromethyl)phenoxy]acetic acid
{2-methyl-4-[({5-[4-(trifluoromethyl)phenyl]-3-furyl}methyl)thio]phenoxy}acetic acid
{2-methyl-4-[({5-[4-(trifluoromethyl)phenyl]-2-furyl}methyl)thio]phenoxy}acetic acid
{2-methyl-4-[({5-[4-(trifluoromethyl)phenyl]thien-3-yl}methyl)thio]phenoxy}acetic acid
{2-methyl-4-[({5-[4-(trifluoromethyl)phenyl]thien-2-yl}methyl)thio]phenoxy}acetic acid
[4-({[5-(4-chlorophenyl)-2-(trifluoromethyl)-3-furyl]methyl}thio)-2-methylphenoxy]acetic acid
(4-{[5-(4-chlorophenyl)-2-methyl-3-furyl]methoxy}-2-methylphenoxy)acetic acid
[2-methyl-4-({2-(trifluoromethyl)-5-[4-(trifluoromethyl)phenyl]-3-furyl}methoxy)phenoxy]acetic acid
[2-methyl-4-({2-methyl-5-[4-(trifluoromethyl)phenyl]-3-furyl}methoxy)phenoxy]acetic acid
[2-methyl-4-({3-methyl-5-[4-(trifluoromethyl)phenyl]-2-furyl}methoxy)phenoxy]acetic acid
3-(4-{[5-(4-chlorophenyl)-2-(trifluoromethyl)-3-furyl]methoxy}phenyl)propanoic acid
(4-{[5-(4-chlorophenyl)-2-(trifluoromethyl)-3-furyl]methoxy}-2-methylphenoxy)acetic acid
[4-({[5-(4-chlorophenyl)-2-methyl-3-furyl]methyl}thio)-2-(trifluoromethyl)phenoxy]acetic acid
{4-[({3-[(isopropylthio)methyl]-5-[4-(trifluoromethyl)phenyl]thien-2-yl}methyl)thio]-2-methylphenoxy}acetic acid
{4-[({3-[(benzylthio)methyl]-5-[4-(trifluoromethyl)phenyl]thien-2-yl}methyl)thio]-2-methylphenoxy}acetic acid
3-(4-{[5-(4-chlorophenyl)-2-(trifluoromethyl)-3-furyl]methoxy}-2-methylphenyl)propanoic acid
{2-methyl-4-[({2-(phenoxymethyl)-5-[4-(trifluoromethyl)phenyl]-3 furyl}methyl)thio]phenoxy}acetic acid
3-[2-methyl-4-(2-{2-methyl-5-[4-(trifluoromethyl)phenyl]-3-furyl}ethyl)phenyl]propanoic acid
{2-methyl-4-[({3-{[4-(trifluoromethyl)phenoxy]methyl}-5-[4-(trifluoromethyl)phenyl]thien-2-yl}methyl)thio]phenoxy}acetic acid
{4-[({2-{[(2-furylmethyl)thio]methyl}-5-[4-(trifluoromethyl)phenyl]-3-furyl}methyl)thio]-2-methylphenoxy}acetic acid
{2-methyl-[({2-[2-(4-methylphenyl)ethyl]-5-[4-(trifluoromethyl)phenyl]-3-furyl}methyl)thio]phenoxy}acetic acid
{4-[({2-{[(2,4-difluorophenyl)thio]methyl}-5-[4-(trifluoromethyl)phenyl]-3-furyl}methyl)thio]-2-methylphenoxy}acetic acid
{4-[({2-{[(3,5-dimethylphenyl)thio]methyl}-5-[4-(trifluoromethyl)phenyl]-3-furyl}methyl)thio]-2-methylphenoxy}acetic acid
{4-[({2-{[(4-tert-butylphenyl)thio]methyl}-5-[4-(trifluoromethyl)phenyl]-3-furyl}methyl)thio]-2-methylphenoxy}acetic acid
{2-methyl-4-[({3-{[methyl(phenyl)amino]methyl}-5-[4-(trifluoromethyl)phenyl]thien-2-yl}methyl)thio]phenoxy}acetic acid
{2-methyl-4-[({2-(2-pyridin-4-ylethyl)-5-[4-(trifluoromethyl)phenyl]-3-furyl}methyl)thio]phenoxy}acetic acid hydrochloride
{4-[({2-isobutyl-5-[4-(trifluoromethyl)phenyl]-3-furyl}methyl)thio]-2-methylphenoxy}acetic acid
{2-methyl-4-[({2-{[methyl(pyridin-3-yl)methyl)amino]methyl}-5-[4-(trifluoromethyl)phenyl]-3-furyl}methyl)thio]phenoxy}acetic acid hydrochloride
{4-[({2-{[cyclohexyl(methyl)amino]methyl}-5-[4-(trifluoromethyl)phenyl]-3-furyl}methyl)thio]-2-methylphenoxy}acetic acid hydrochloride
{2-methyl-4-[({2-{[methyl(2-phenylethyl)amino]methyl}-5-[4-(trifluoromethyl)phenyl]-3-furyl}methyl)thio]phenoxy}acetic acid hydrochloride
[2-methyl-4-(1-{3-methyl-5-[4-(trifluoromethyl)phenyl]thien-2-yl}ethoxy)phenoxy]acetic acid
[4-({3-[(isopropylthio)methyl]-5-[4-(trifluoromethyl)phenyl]thien-2-yl}methoxy)-2-methylphenoxy]acetic acid
[2-methyl-4-(1-{5-[4-(trifluoromethyl)phenyl]thien-2-yl}ethoxy)phenoxy]acetic acid
[2-methyl-4-(1-{5-[4-(trifluoromethyl)phenyl]thien-3-yl}ethoxy)phenoxy]acetic acid
[2-methyl-4-(phenyl{5-[4-(trifluoromethyl)phenyl]thien-3-yl}methoxy)phenoxy]acetic acid
2-methyl-2-[2-methyl-4-(phenyl{5-[4-(trifluoromethyl)phenyl]thien-3-yl}methoxy)phenoxy]propanoic acid
{2-methyl-4-[({3-methyl-5-[4-(trifluoromethoxy)phenyl]thien-2-yl}methyl)thio]phenoxy}acetic acid

[4-({5-[2,5-difluoro-4-(trifluoromethyl)phenyl]-3-methylthien-2-yl}methoxy)-2-methylphenoxy]acetic acid

[4-({5-[2,3-difluoro-4-(trifluoromethyl)phenyl]-3-methylthien-2-yl}methoxy)-2-methylphenoxy]acetic acid

[2-methyl-4-({3-methyl-5-[4-(1,1,2,2-tetrafluoroethoxy)phenyl]thien-2-yl}methoxy)phenoxy]acetic acid

[4-({5-[2-fluoro-4-(trifluoromethyl)phenyl]-3-methylthien-2-yl}methoxy)-2-methylphenoxy]acetic acid More Preferred:

{2-methyl-4-[({3-methyl-5-[4-(trifluoromethyl)phenyl]-2-furyl}methyl)thio]phenoxy}acetic acid {2-methyl-4-[({3-methyl-4-[4-(trifluoromethyl)phenyl]thien-2-yl}methyl)thio]phenoxy}acetic acid

[4-({[5-(4-chlorophenyl)-2-methyl-3-furyl]methyl}thio)-2-methylphenoxy]acetic acid {2-methyl-4-[({2-(trifluoromethyl)-5-[4-(trifluoromethyl)phenyl]-3-furyl}methyl)thio]phenoxy}acetic acid

[2-methyl-4-(2-{4-methyl-2-[4-(trifluoromethyl)phenyl]-1,3-thiazol-5-yl}ethyl)phenoxy]acetic acid

[2-methyl-4-(2-{3-methyl-5-[4-(trifluoromethyl)phenyl]thien-2-yl}ethyl)phenoxy]acetic acid (4-{2-[5-(4-chlorophenyl)-2-(trifluoromethyl)-3-furyl]ethyl}-2-methylphenoxy)acetic acid 3-[4-({3-methyl-5-[4-(trifluoromethyl)phenyl]thien-2-yl}methoxy)phenyl]propanoic acid {2-methyl-4-[({3-(phenoxymethyl)-5-[4-(trifluoromethyl)phenyl]thien-2-yl}methyl)thio]phenoxy}acetic acid 3-[2-methyl-4-({3-methyl-5-[4-(trifluoromethyl)phenyl]thien-2-yl}methoxy)phenyl]propanoic acid {4-[({2-[(benzylthio)methyl]-5-[4-(trifluoromethyl)phenyl]-3-furyl}methyl)thio]-2-methylphenoxy}acetic acid {4-[({2-[(isopropylthio)methyl]-5-[4-(trifluoromethyl)phenyl]-3-furyl}methyl)thio]-2-methylphenoxy}acetic acid {2-methyl-4-[({2-{[methyl(phenyl)amino]methyl}-5-[4-(trifluoromethyl)phenyl]-3-furyl}methyl)thio]phenoxy}acetic acid

[2-methyl-4-(2-{2-methyl-5-[4-(trifluoromethyl)phenyl]-3-furyl}ethyl)phenoxy]acetic acid 3-[2-methyl-4-(2-{3-methyl-5-[4-(trifluoromethyl)phenyl]thien-2-yl}ethyl)phenyl]propanoic acid

[2-methyl-4-({2-methyl-5-[4-(trifluoromethyl)phenyl]thien-3-yl}methoxy)phenoxy]acetic acid {4-[({2-isopentyl-5-[4-(trifluoromethyl)phenyl]-3-furyl}methyl)thio]-2-methylphenoxy}acetic acid {2-methyl-4-[({2-methyl-5-[4-(trifluoromethyl)phenyl]thien-3-yl}methyl)thio]phenoxy}acetic acid

[4-[({2-methyl-5-[4-(trifluoromethyl)phenyl]-3-furyl}methyl)thio]-2-(trifluoromethyl)phenoxy]acetic acid Particularly preferred compounds are {4-[({3-ethyl-5-[4-(trifluoromethyl)phenyl]thien-2-yl}methyl)thio]-2-methylphenoxy}acetic acid

[4-({[5-(4-chlorophenyl)-2-(trifluoromethyl)-3-furyl]methyl}thio)-2-methylphenoxy]acetic acid

[2-methyl-4-({3-methyl-5-[4-(trifluoromethyl)phenyl]thien-2-yl}methoxy)phenoxy]acetic acid {2-methyl-4-[({3-methyl-5-[4-(trifluoromethyl)phenyl]thien-2-yl}methyl)thio]phenoxy}acetic acid {2-methyl-4-[({2-methyl-5-[4-(trifluoromethyl)phenyl]-3-furyl}methyl)thio]phenoxy}acetic acid {2-ethyl-4-[({2-methyl-5-[4-(trifluoromethyl)phenyl]-3-furyl}methyl)thio]phenoxy}acetic acid {2-isopropyl-4-[({2-methyl-5-[4-(trifluoromethyl)phenyl]-3-furyl}methyl)thio]phenoxy}acetic acid

[2-methyl-4-({3-methyl-5[4-(trifluoromethoxy)phenyl]thien-2-yl}methoxy)phenyl]acetic acid {4-[({2-[(benzylthio)methyl]-5-[4-(trifluoromethyl)phenyl]-3-furyl}methyl)thio]-2-methylphenoxy}acetic acid It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

The compounds of the invention may be prepared by one of the following routes:

(a) Coupling of a thiol or phenol (A) and a heterocyclic methanol (B), by the Mitsonobu reaction (O. Mitsunobu, Synthesis, 1981, 1) or by reaction of the thiol or phenol (A) with a heterocyclic methyl halide (eg chloride) prepared from the methanol (B), followed by hydrolysis of the ester $R_{10}$

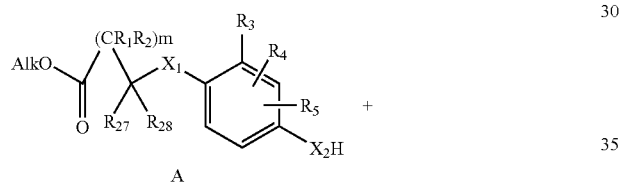

A

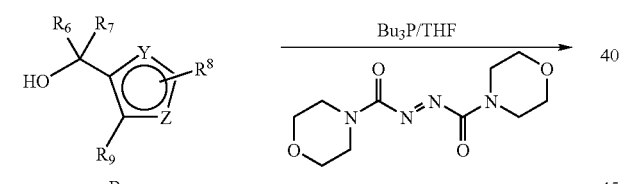

B

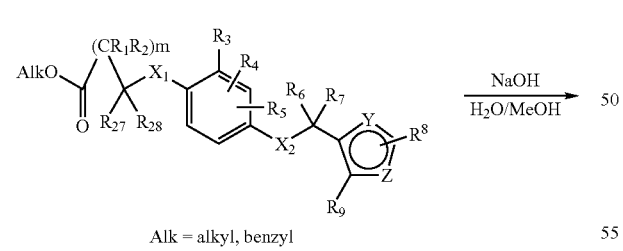

Alk = alkyl, benzyl

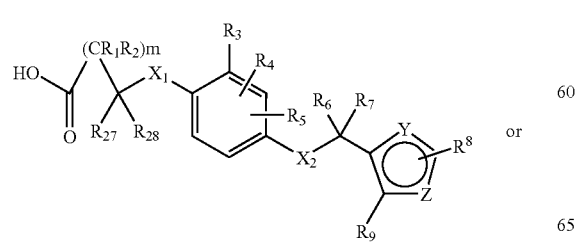

or

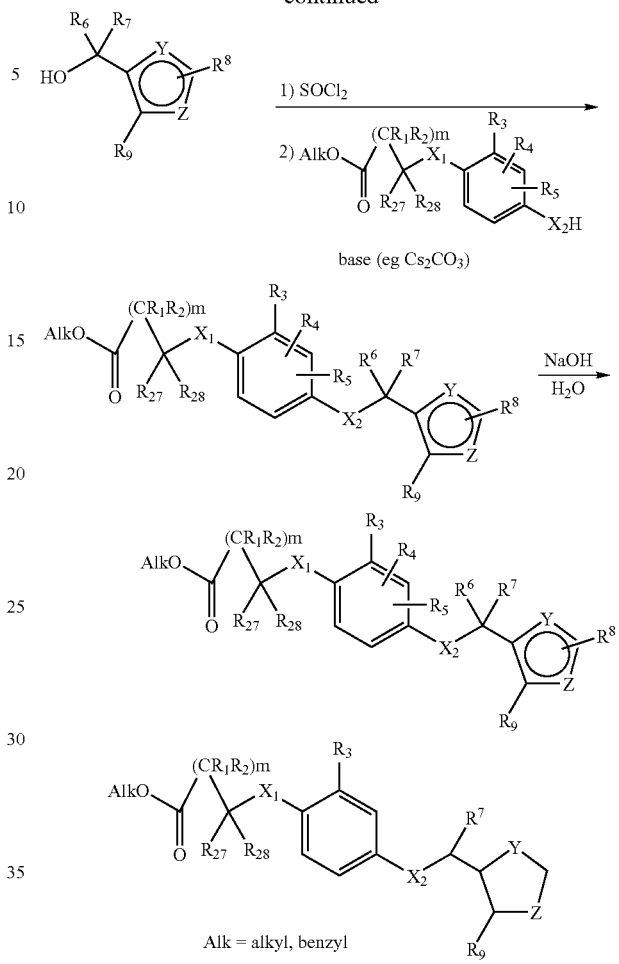

Alk = alkyl, benzyl or a further modification is to use a sulfonyl chloride, which is reduced and coupled in situ with a heterocyclic methanol.

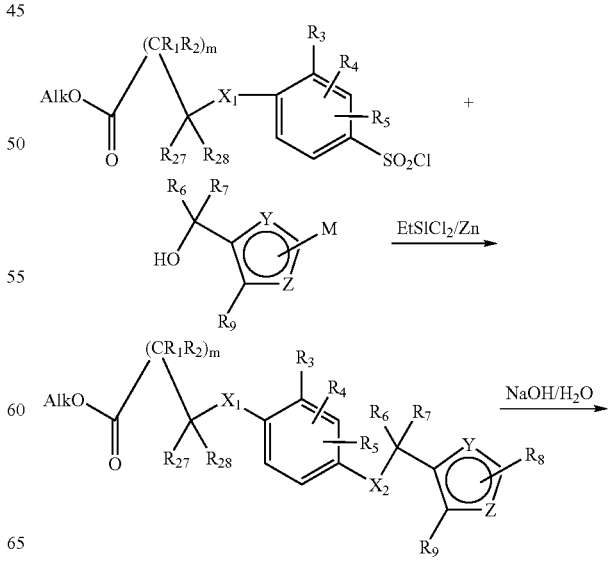

-continued

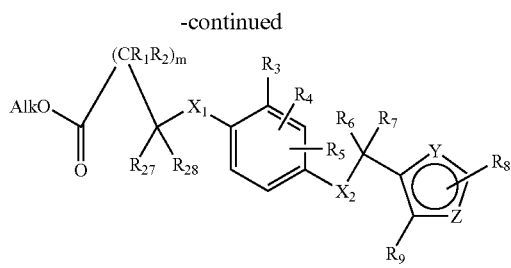

Alk = alkyl, benzyl

Intermediates A can be prepared as follows; where $X_2$=$SO_2Cl$, by direct sulfonation of an aromatic precursor such as commercially available ester C (A. Badawi et al, Pharmazie, 1983, 38(12), 838–41). The ester C may also be prepared from commercially available phenol by alkylation with ethyl bromoacetate. Where $X_2$=SH these compounds can be prepared by reduction of the sulfonyl chlorides (H. Uchiro et al, Tetrahedron Lett. (1999), 40(16), 3179–3182).

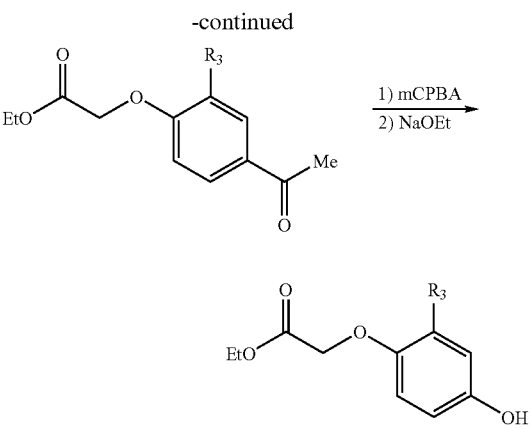

Where $X_2$=OH a commercially available phenol, such as E, is alkylated, and then reacted with a peracid such as meta chloroperbenzoic acid (mCPBA) to give an acetyl ester which is finally hydrolysed to give the product.

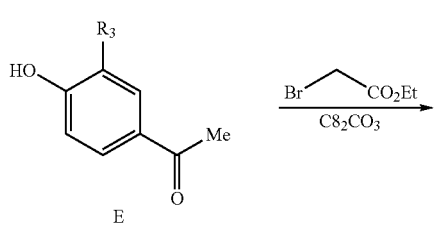

-continued

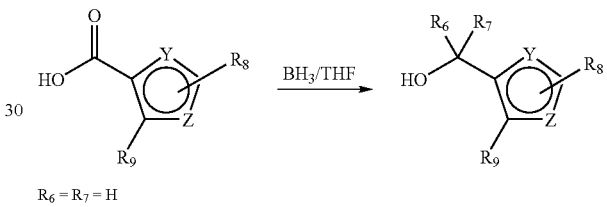

The intermediate alcohols B may be prepared by one of the following general routes:

i) Reduction of a commercially available acid using a reducing agent such as borane:

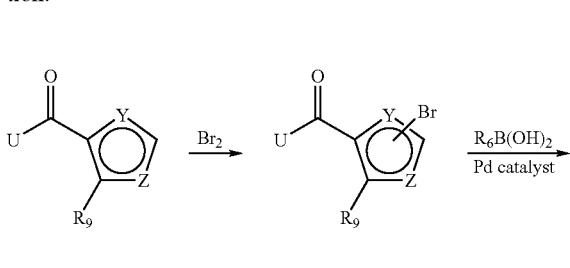

$R_6$ = $R_7$ = H ii) Bromination of a known/commercially available heterocyclic ester or aldehyde, followed by Suzuki coupling of the resulting bromide with a boronic acid and then reduction:

U = H or alkoxy iii) The Suzuki coupling of a protected heterocyclic boronate ester, prepared by the orthometallation of a heterocyclic ring with a strong base such as butyllithium followed by quenching with an alkoxyborane, with commercially available aryl bromide followed by subsequent removal of the protecting group, such as a silyl ether.

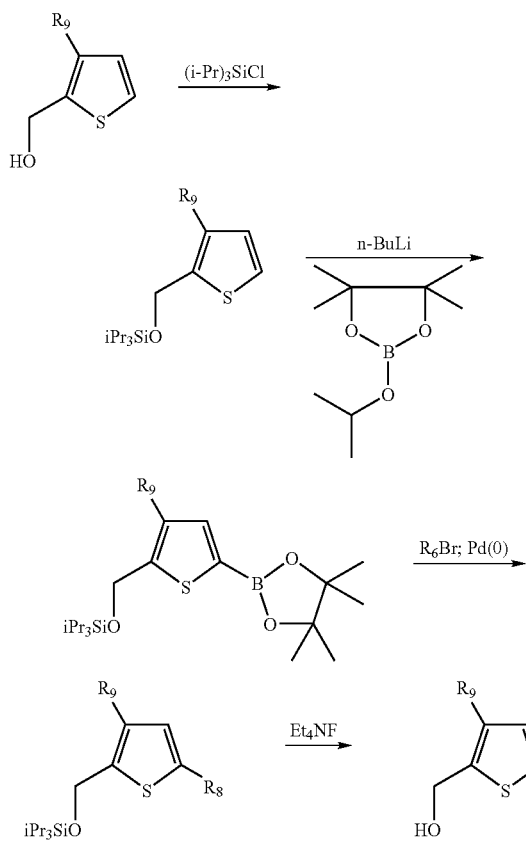

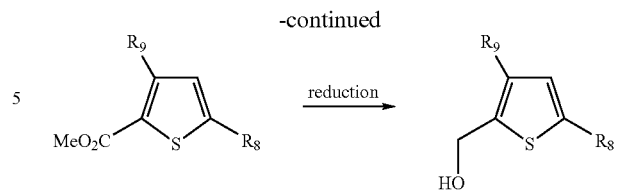

vi) Where $R_9$ is a more complex substituent (not methyl) this can be introduced by reacting a compound in which $R_9$ is methyl with a brominating agent to give F which can be converted to the desired methanol by one of two methods:

by reacting with a nucleophilic group $R_{11}$ ($R_{11}$ can be a thiol, amine, alcohol or an organometallic reagent such as an organocuprate) followed by reduction of the ester gives the desired methanol.

(a)

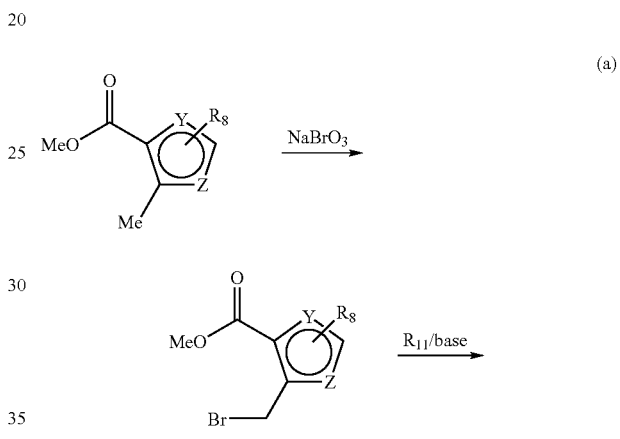

iv) Alkylation of heterocyclic aldehydes or ketones using organometallic reagents, the general methods for preparation of which are described elsewhere

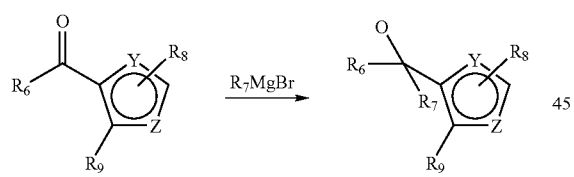

v) The heterocyclic ring may be constructed by the following procedure

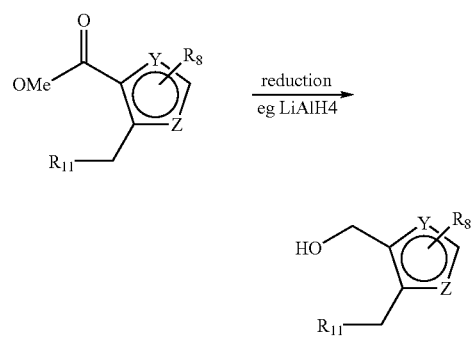

by reaction of the bromomethyl group to give a phosphorous reagent (such as a phosphonium salt) and reaction of this with a ketone or aldehyde. Hydrogenation followed by reduction of the ester gives the desired methanol.

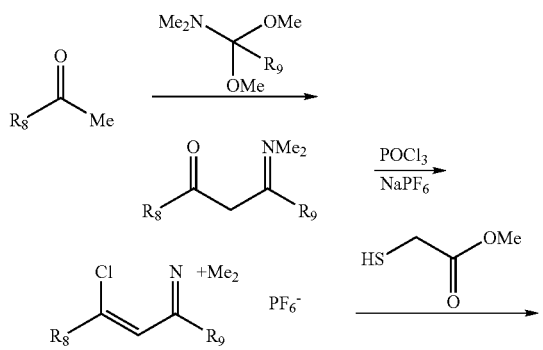

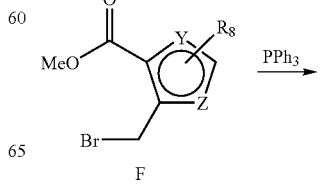

-continued

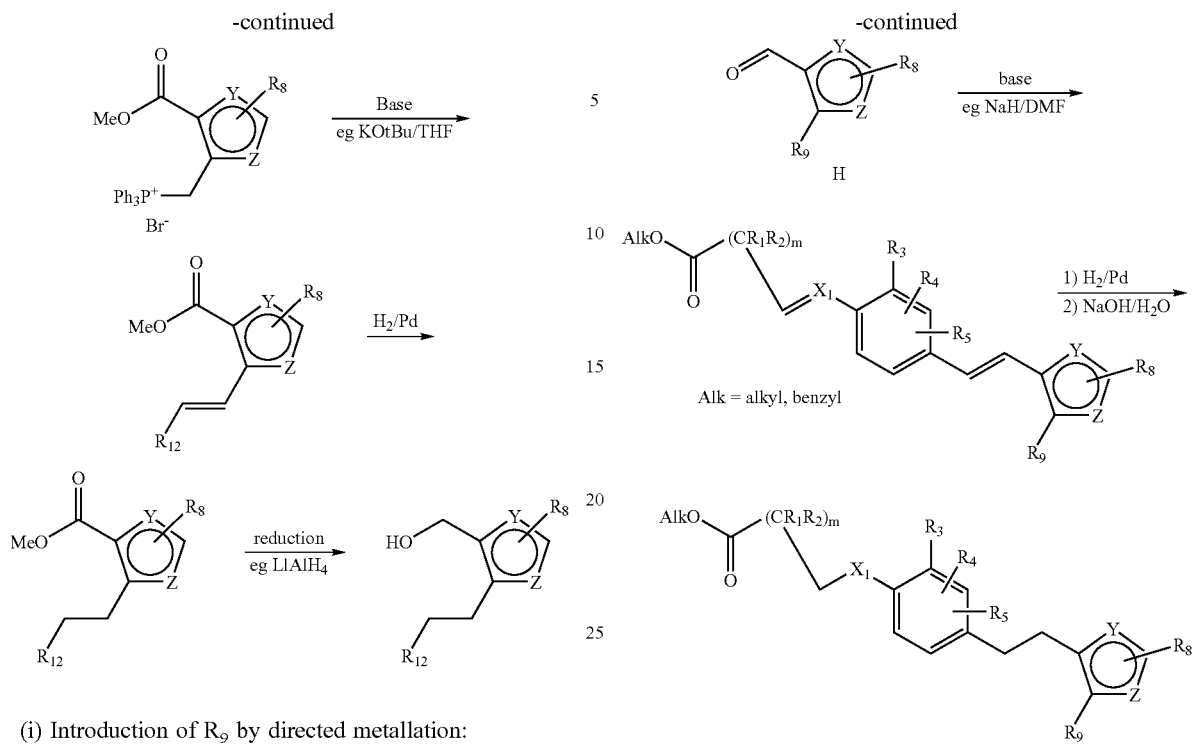

(i) Introduction of R$_9$ by directed metallation:

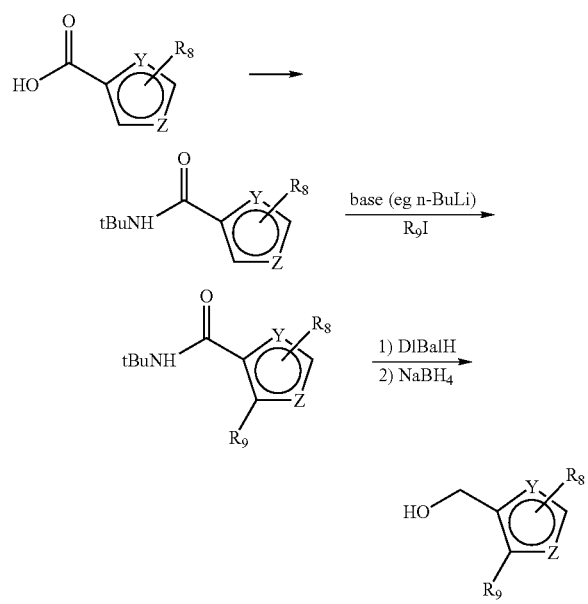

(b) Wittig (or related phosphorous reagent chemistry)

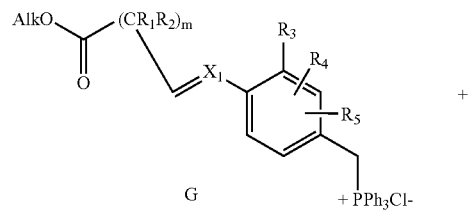

When X$_1$=C the bond between X$_1$ and the adjacent carbon may be single or double—where it is double it is removed in the hydrogenation step. Intermediates H are prepared by oxidation of the methanols described above. Intermediates G can be prepared can be prepared from a compound such as a commercially available ester C by treatment with formaldehyde and hydrochloric acid (Org. React. 1942, 1, 303) to give chloride I followed by reaction with triphenylphosphine.

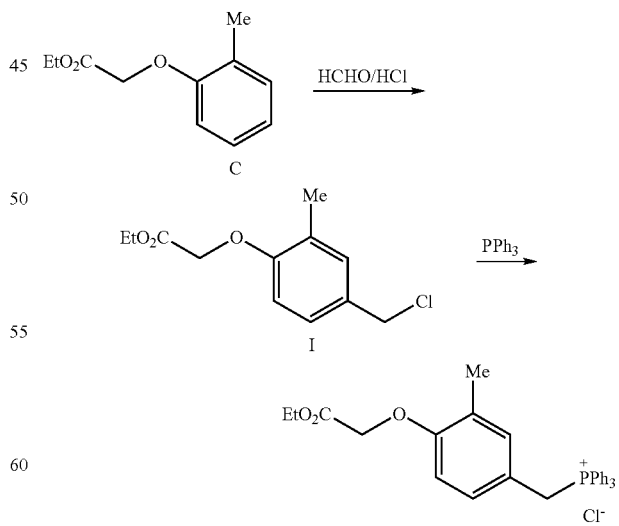

(c) By reaction of a bromide J with an organometallic reagent such as a boronic acid. There is hydrolysis of a base labile ester during the reaction.

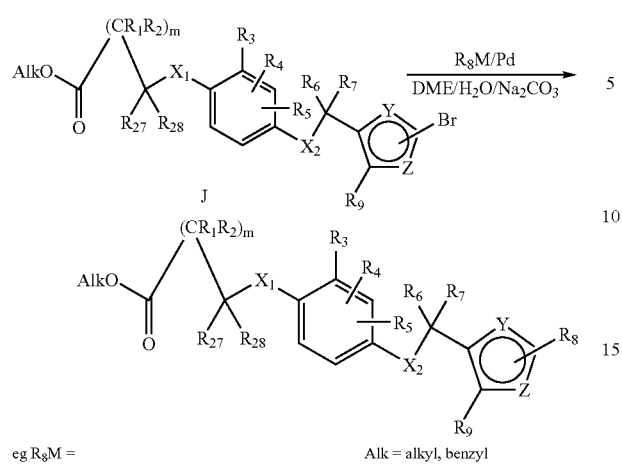

eg R₈M = Alk = alkyl, benzyl

Bromides J are prepared by the Mitsonobu reaction as described in section (a) from intermediates A and B, where B is an alcohol synthesized from commercially available starting materials using standard chemical methods.

(d) By reaction of an organometallic species (K) with an aryl bromide

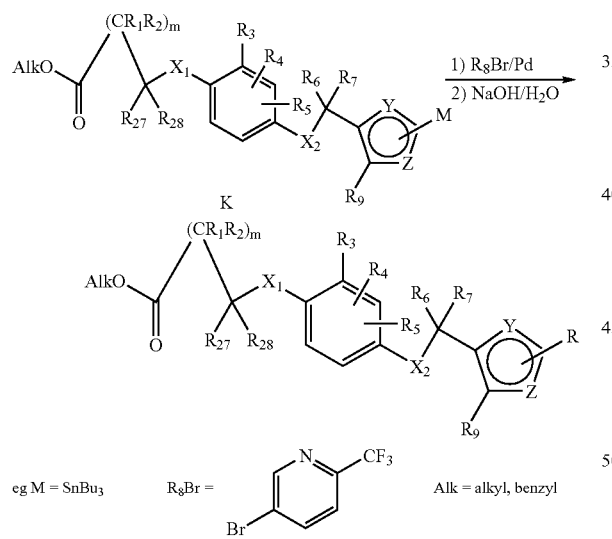

eg M = SnBu₃   R₈Br =   Alk = alkyl, benzyl

Intermediate K is prepared as described in section (a), intermediates B are prepared by routes analogous to that described below:

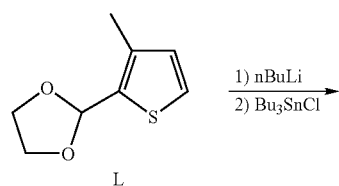

L

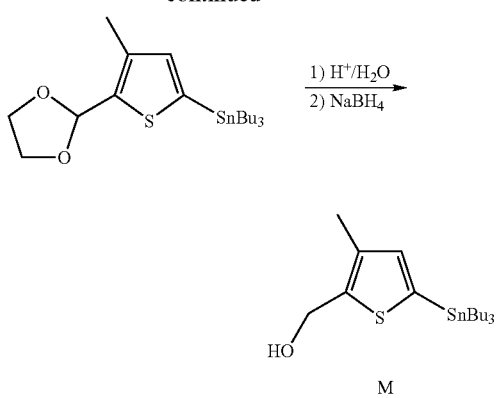

M

A protected aldehyde eg L is reacted with strong base such as n-butyl lithium followed by tributyltin chloride. Hydrolysis, followed by reduction gives the desired alcohol (f) By alkylation of an intermediate N and subsequent hydrolysis

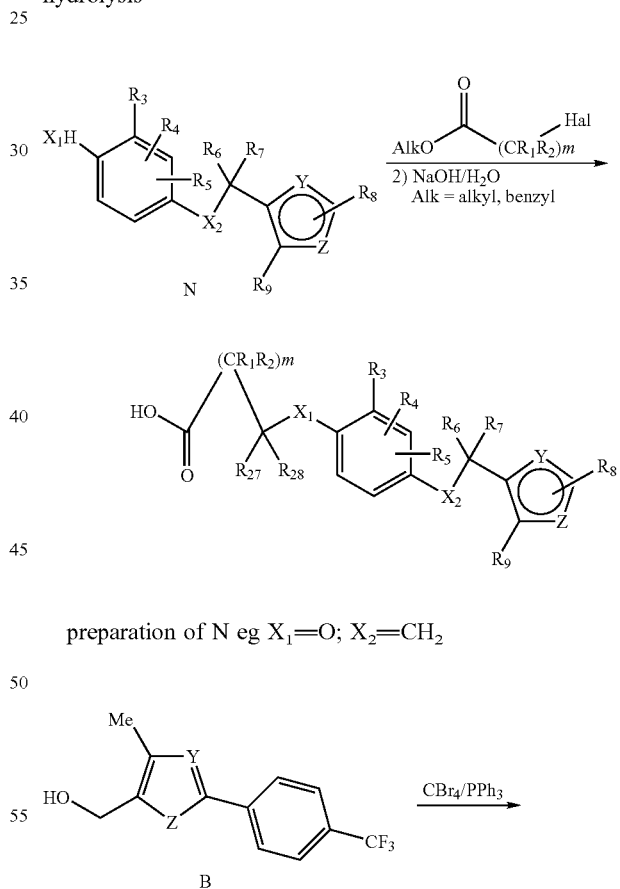

preparation of N eg $X_1$=O; $X_2$=CH₂

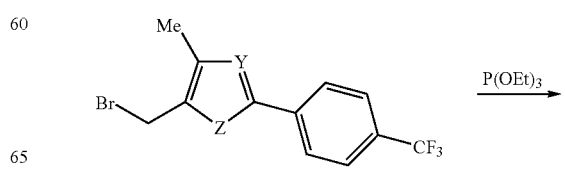

-continued

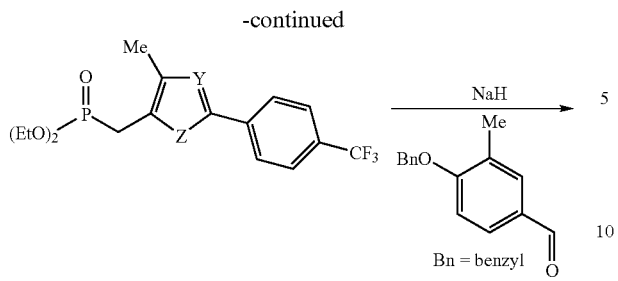

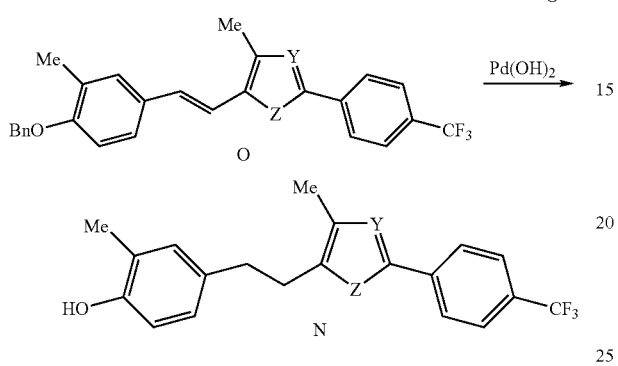

The alcohol B, prepared from known ester (see above), is converted to the bromide and then to the phophonate (Org. React., 1951, 6, 273), which reacts with the known benzaldehyde in the presecence of base, to give alkene O, reduction using hydrogen over a palladium catalyst gives N.

(g) by reaction of a halide P with a nucleophile reagent such as an amino ester with a palladium catalyst, where $X_1$=NHR

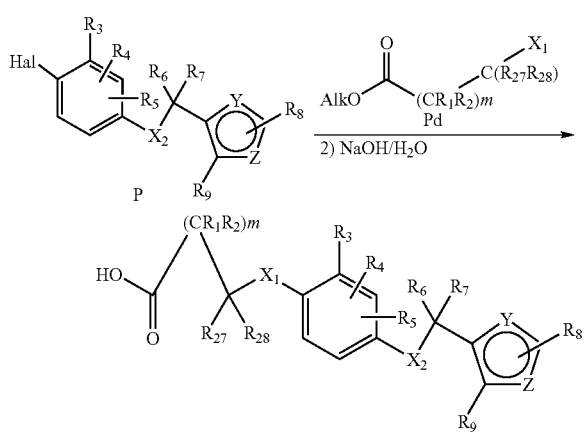

Intermediate P can be prepared as described in section (a) starting from a halide such as R

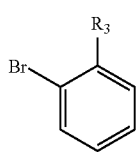

(h) By reaction of an organometallic species (S) with an aryl bromide.

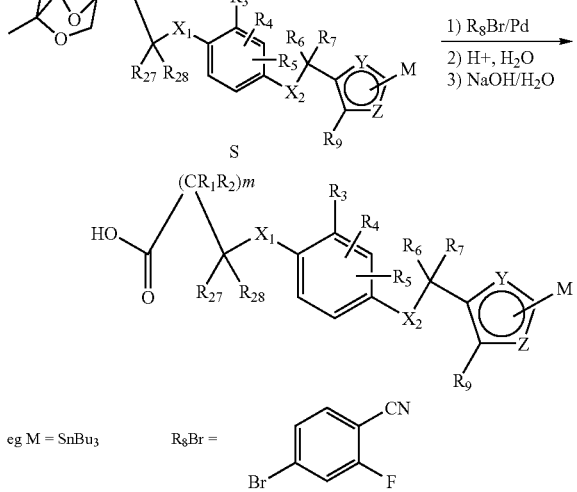

Intermediate S can be prepared as shown in the scheme below

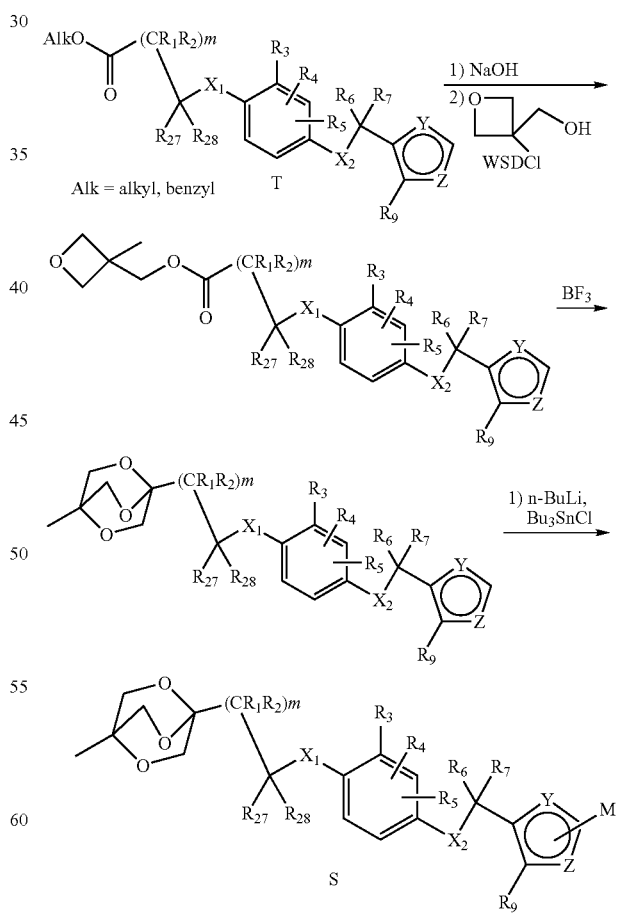

T can be prepared as outlined in the schemes above by Wittig or related phoshorus chemistry.

Intermediate Y may also be prepared by the following procedure to introduce alkyl groups ($R_{10}$; $R_{11}$=Me); The ketone X is prepared by Friedel-Crafts acylation of the thiophene U with the acid V. X may be dialkylated by using a strong non-nucleophilic base such as sodium hydride followed by quenching the enolate with alkyl iodides. Removal of the methyl ether followed by alkylation with ethyl bromoacetate furnishes ketone Y which may be reduced to the ester Z with triethylsilane and trifluoroacetic acid.

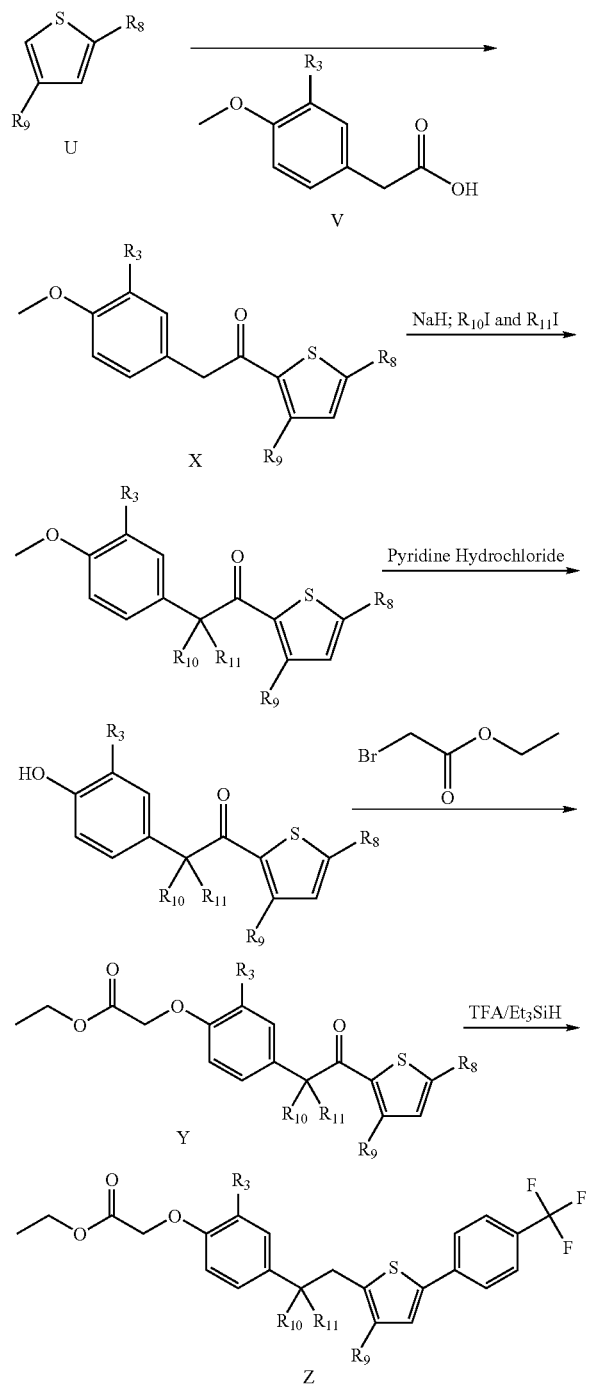

The invention is further illustrated by the following Examples which should not be construed as constituting a limitation thereto.

General Purification and Analytical Methods

Analytical HPLC was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 minutes 0% B, 0.7–4.2 minutes 100% B, 4.2–5.3 minutes 0% B, 5.3–5.5 minutes 0% B at a flow rate of 3 ml/minutes. The mass spectra (MS) were recorded on a Fisons VG Platform spectrometer using electrospray positive [(ES+ve to give $MH^+$ and $M(NH_4)^+$ molecular ions] or electrospray negative [(ES−ve to give $(M-H)^-$ molecular ion] modes.

$^1H$ nmr spectra were recorded using a Bruker DPX 400 MHz spectrometer using tetramethylsilane as the external standard.

Biotage chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+ 5 µm column (5 cm×10 mm i.d.) with 0.1% $HCO_2H$ in water and 95% MeCN, 5% water (0.5% $HCO_2H$) utilising gradient elution at a flow rate of 8 ml minutes$^{-1}$. The Gilson 202-fraction collector was triggered by a VG Platform Mass Spectrometer on detecting the mass of interest.

Hydrophobic frits refers to filtration tubes sold by Whatman.

SPE (solid phase extraction) refers to the use of cartridges sold by International Sorbent Technology Ltd.

TLC (thin layer chromatography) refers to the use of TLC plates sold by Merck coated with silica gel 60 $F_{254}$.

Preparation of Intermediates:

Intermediate 1:

ethyl[2-(trifluoromethyl)phenoxy]acetate

A mixture of 2-trifluoromethylphenol (1.62 g) in anhydrous acetonitrile was treated with cesium carbonate (3.25 g) and ethyl bromoacetate (1.75 g) and the reaction mixture stirred at room temperature for 2 hours. The reaction mixture was diluted with water and ethyl acetate and the organic layer washed with water and dried with brine and over sodium sulfate. Evaporation of ethyl acetate gave the title compound as a colourless oil.

$^1H$ NMR (CDCl$_3$) 7.60 (d, 1H), 7.47 (t, 1H), 7.06 (t, 1H), 6.88 (d, 1H), 4.72 (s, 2H), 6.55 (s, 1H), 4.26 (q, 2H), 1.29 (t, 3H).

Intermediate 2:

ethyl[4-(chlorosulfonyl)-2-methylphenoxy]acetate

Ethyl(2-methylphenoxy)acetate (0.5 g) was added to cooled chlorosulphonic acid (2 ml) at 0° C. The mixture was stirred with ice cooling for 30 minutes, then allowed to warm to ambient temperature and stirred for 3 hours.

The reaction mixture was then poured cautiously onto ice, and the mixture allowed to stand overnight. The title compound was isolated as a whire solid by filtration.

m/z ($MH^+$)=278

Intermediate 3:

ethyl[4-(chlorosulfonyl)-2-(trifluoromethyl)phenoxy]acetate prepared from intermediate 1, in an analogous way to intermediate 2, $^1H$ NMR (CDCl$_3$) 8.29 (s, 1H), 8.17 (dd, 2H), 7.04 (d, 1H), 4.88 (s, 2H), 6.55 (s, 1H), 4.30 (q,2H), 1.31 (t, 3H)

Intermediate 4:
ethyl(4-mercapto-2-methylphenoxy)acetate

A solution of ethyl[4-(chlorosulfonyl)-2-methylphenoxy]acetate (intermediate 2, 18.49) in chloroform was dried by using a hydrophobic frit and this solution was evaporated. The residue was dissolved in chloroform (125 ml) and this solution added to a mixture of zinc powder (14.4 g) and dimethyldichlorosilane (26.6 ml) in chloroform (125 ml). The mixture was cooled to 0° C. and 1,3-dimethyl-2-imidazolinone (20.6 ml) added cautiously. The reaction mixture was stirred at ambient temperature for 10 minutes and then stirred at reflux for 18 hours. The reaction mixture was evaporated and the resulting oil filtered and then partitioned between diethyl ether and 2M aqueous hydrochloric acid; the organic phase was dried with brine and over magnesium sulfate. The product isolated after evaporation of the solvent was further purified by flash column chromatography using neat chloroform as eluent to give the title compound as a colourless oil which solidified upon standing.

HPLC Rt=3.5 minutes

Intermediate 5:
ethyl(4-acetyl-2-methylphenoxy)acetate 1-(4-Hydroxy-3-methylphenyl)ethanone (90 g) and cesium carbonate (216 g) were stirred in acetonitrile (900 ml) at room temperature under nitrogen for 10 minutes. Ethyl bromoacetate (73 ml) was added and the mixture heated to 40° C. for 3 hours. Further ethyl bromoacetate (2.5 ml) and cesium carbonate (1 g) were added and heating continued for a further hour. The cooled reaction was filtered and the filtrate concentrated to give the title compound as a yellow oil.

m/z (MH$^+$)=237

Intermediate 6:
ethyl[4-(acetyloxy)-2-methylphenoxy]acetate

A solution of ethyl(4-acetyl-2-methylphenoxy)acetate (intermediate 5, 141 g) in dichloromethane (3000 ml) containing 4-toluenesulphonic acid (13.7) was heated to 39° C. under nitrogen m-chloro perbenzoic acid (312 g) was added portionwise over 40 minutes. The mixture was stirred for a further 7 hours and then allowed to cool with stirring overnight. Dichloromethane (1000 ml) was added and the mixture filtered. The filtrate was added slowly to a solution of potassium iodide (750 g) in water (5000 ml) and the mixture stirred for 10 minutes. The organic layer was separated and again added to a solution of potassium iodide (750 g) in water (5000 ml). After stirring for 10 minutes the organic layer was again separated, then washed with 10% aqueous sodium sulfite followed by water and brine, then dried over magnesium sulfate, filtered and the filtrate concentrated to give the title compound as an orange oil.

m/z (MH$^+$)=253

Intermediate 7:
ethyl(4-hydroxy-2-methylphenoxy)acetate

A solution of ethyl[4-(acetyloxy)-2-methylphenoxy]acetate (intermediate 6, 148 g) in ethanol (1300 ml) was treated with sodium ethoxide (41.3 g) and the mixture heated to 45° C. for 2.5 hours. The mixture as cooled to 22° C. and concentrated hydrochloric acid added to give a neutral (pH 7) solution. The resulting mixture was concentrated and the residue dissolved in a mixture of t-butylmethyl ether, water and brine. The organic layer was separated, washed with brine and dried over sodium sulfate and filtered. The filtrate was concentrated to give a brown solid which was further purified by precipitation from a solution in dichloromethane (100 ml) on addition of cyclohexane (710 ml) to give the title compound as a brown solid.

m/z (MH$^+$)=211

Intermediate 8:
ethyl 2-(4-acetyl-2-methylphenoxy)-2-methylpropanoate

A suspension of 1-(4-hydroxy-3-methylphenyl)ethanone (20.1 g) in acetonitrile (200 ml) was added to a suspension of cesium carbonate (86.6 g) in acetonitrile (400 ml) and the mixture stirred under nitrogen at room temperature for 2 minutes. ethyl 2-bromo-2-methylpropanoate (33 g) was added and the mixture stirred for 25 hours, further ethyl 2-bromo-2-methylpropanoate (33 g) was added and the mixture stirred for a further 16 hours. The mixture was filtered and the filtrate concentrated to give an orange oil, the oil was dissolved in ethyl acetate and the solution washed thrice with 1M sodium hydroxide and brine. The organic layer was separated, dried over sodium sulfate, filtered and the filtrate concentrated; the resulting oil was purified by Biotage® chromatography eluting with cyclohexane:ethyl acetate (9:1) to give the title compound as a clear oil.

m/z (MH$^+$)=265

Intermediate 9:
ethyl 2-[4-(acetyloxy)-2-methylphenoxy]-2-methylpropanoate

A solution of ethyl 2-(4-acetyl-2-methylphenoxy)-2-methylpropanoate (intermediate 8, 37.33 g) in dichloromethane (650 ml) was treated with 4-toluenesulphonic acid (2.75 g) followed by m-chloroperbenzoic acid (60.5 g) and the mixture warmed to 40° C. and stirred under nitrogen for 19 hours. The cooled mixture was treated with dichloromethane (350 ml) and the resulting mixture added to aqueous potassium iodide (1000 ml, 10% solution). The organic layer was collected and washed twice with water and brine, then dried over sodium sulfate, filtered and the filtrate concentrated to give the title compound as an orange oil.

m/z (MH$^+$)=281

Intermediate 10:
ethyl 2-(4-hydroxy-2-methylphenoxy)-2-methylpropanoate

A solution of ethyl 2-[4-(acetyloxy)-2-methylphenoxy]-2-methylpropanoate (intermediate 9, 40.8 g) in ethanol (280 ml) was treated with sodium ethoxide (12.9 g) at room temperature under nitrogen. The resulting solution was heated to 50° C. for 1 hour. 2M hydrochloric acid (95 ml) was added to the cooled reaction and the solution concentrated. The residue was dissolved in t-butylmethyl ether and the resulting solution washed with water followed by brine and then dried over sodium sulfate, filtered and the filtrate concentrated to give a brown oil. Further purification by Biotage® chromatography eluting initially with cyclohexane and then cyclohexane:ethyl acetate (5:1) gave the title compound as an orange oil.

m/z(MH$^+$)=239

Intermediate 11:
Ethyl 3-[4-(benzyloxy)-2-methylphenyl]prop-2-enoate

A solution of triethyl phosphonoacetate (0.88 ml) in dry tetrahydrofuran (20 ml) was cooled to 0° C. and treated in small portions with a 60% dispersion in oil of sodium hydride (0.194 g). Once effervescence was complete, a solution of 2-methyl-4-benzyloxybenzaldehyde (1.0 g) in dry tetrahydrofuran (20 ml) was added drop-wise. The resulting solution was stirred at 0° C. for 1.5 hours then the cooling bath removed and the reaction allowed to warm to 21° over 2.5 hours. The reaction was then poured into ethyl acetate/water and the aqueous phase separated and extracted with more ethyl acetate. The combined organic phases were washed with water, brine, dried over sodium sulfate and evaporated in vacuo. The product was further purified by flash column chromatography using cyclohexane:ethyl acetate (19:1) as an eluent to give the title compound as a white solid.

HPLC Rt=4.1 minutes

Intermediate 12:

Ethyl 3-(4-hydroxy-2-methylphenyl)propanoate

A solution of ethyl 3-[4-(benzyloxy)-2-methylphenyl]prop-2-enoate (intermediate 11, 1.054 g) in ethanol (50 ml) was added to a suspension of palladium hydroxide on carbon (0.15 g) in ethanol (5 ml) under nitrogen gas. The resulting suspension was then stirred under a hydrogen atmosphere for 3 hours. The mixture was filtered through Harborlite filter aid and the pad washed with more ethanol. The combined filtrates were evaporated in vacuo to give the title compound as a clear oil.

HPLC Rt=3.1 minutes.

Intermediate 13:

ethyl[4-(hydroxymethyl)-2,6-dimethylphenoxy]acetate

A solution of 4-(hydroxymethyl)-2,6-dimethylphenol (P. Claus et al., Monatsh. Chem. 1972, 103(4), 1178–1193) (1.9 g) in acetonitrile (50 ml) was treated with ethyl bromoacetate (2.17 g) and caesium carbonate (4.24 g) and the mixture stirred at room temperature overnight. The solution was concentrated and the residue partitioned between ethyl acetate and water. The organic layer was collected, dried over magnesium sulfate and filtered. The filtrate was concentrated to give the title compound as a yellow oil.

$^1$H NMR (CDCl$_3$) δ 7.0 (s, 2H), 4.6 (s, 2H), 4.4 (s, 2H), 4.3 (q, 2H), 2.3 (s, 6H), 1.35 (t, 3H)

Intermediate 14:

[4-(2-ethoxy-2-oxoethoxy)-3,5-(dimethylbenzyl](triphenyl)phosphonium bromide

A solution of ethyl[4-(hydroxymethyl)-2,6-dimethylphenoxy]acetate (3.0 g) in acetonitrile (100 ml) was treated with triphenylphosphine hydrobromide (4.32 g) and the mixture heated to reflux for 6 hours. The cooled solution was concentrated and the residue triturated with diethyl ether (100 ml) to precipitate the title compound which was isolated by filtration.

HPLC Rt=2.7 minutes

Intermediate 15:

[3-tert-butyl-4-(2-ethoxy-2-oxoethoxy)-5-methylbenzyl](triphenyl)phosphonium bromide The title compound was prepared by an analogous method to that used for the preparation of intermediate 14 starting from 2-tert-butyl-4-(hydroxymethyl)-6-methylphenol (P. G McCracken et al J. Org. Chem. (1997), 62(6), 1820–1825

HPLC Rt=3.1 minutes

Intermediate 16:

ethyl[4-(chloromethyl)-2-methylphenoxy]acetate

A mixture of ethyl(2-methylphenoxy)acetate (10.0 g) in petroleum ether (40–60) (24 ml) and concentrated hydrochloric acid (60 ml) was treated with 37% aqueous formaldehyde (4.2 ml) and the bi-phasic mixture stirred rapidly for 18 hours. The reaction mixture was diluted with ethyl acetate; the aqueous layer separated and the organic layer washed with water and then dried with brine and over sodium sulfate. The product isolated after evaporation of the solvent was further purified by flash column chromatography using cyclohexane:ethyl acetate (14:1) as eluent to give the title compound as a white solid.

m/z (M–Cl)$^+$=207

Intermediate 17:

[4-(2-ethoxy-2-oxoethoxy)-3-methylbenzyl](triphenyl)phosphonium chloride

A mixture of [4-(2-ethoxy-2-oxoethoxy)-3-methylbenzyl](triphenyl)phosphonium chloride (intermediate 16, 2.5 g) and triphenylphosphine (2.73 g) in toluene (25 ml) was stirred at reflux for 68 hours. The reaction mixture was cooled and the title compound, a white solid, isolated by filtration.

m/z (M–Cl)$^+$=465

Intermediate 18:

(4-bromo-3-methylphenyl)methanol

A solution of methyl-4-bromo-3-methylbenzoate (4.31 g) in dry tetrahydrofuran (20 ml) was stirred and cooled to 0° C. under nitrogen gas. A solution of 1.5M diisobutylaluminium hydride in toluene (44 ml) was added slowly and the reaction stirred for 2.5 hours, then quenched with methanol and allowed to warm to 21° C. Silica was added and the reaction concentrated in vacuo and purified using SPE (Si cartridge) using cyclohexane:ethyl acetate (3:1) as an eluent which furnished the title compound as a brown oil.

HPLC Rt=3.1 minutes

Intermediate 19:

Ethyl(2E)-3-[4-hydroxymethyl)-2-methylphenyl]prop-2-enoate

A solution of (4-bromo-3-methylphenyl)methanol (intermediate 18, 1.319 g) in dry dimethylformamide (15 ml) and triethylamine (7 ml) was stirred at 21° C. under nitrogen gas and treated with ethyl acrylate (0.7 ml), (trisdibenzylideneacetone) dipalladium (0) (0.6 g) and tri(o-tolyl)phosphine (2.0 g). The resulting brown solution was stirred and heated at 80° C. for 2 hours. The reaction was allowed to cool and poured into 2M aqueous sodium carbonate/ethyl acetate. The organic phase was separated and washed with more sodium carbonate. The combined aqueous phases were extracted with more ethyl acetate and the combined organic solution was washed with brine, dried over sodium sulfate and evaporated in vacuo. The isolated product was further purified by flash column chromatography using cyclohexane:ethyl acetate (3:1) as an eluent which gave the title compound as a yellow oil.

HPLC Rt=3.1 minutes

Intermediate 20:

Ethyl(2E)-3-[4-(bromomethyl)-2-methylphenyl]prop-2-enoate

A solution of ethyl(2E)-3-[4-(hydroxymethyl)-2-methylphenyl]prop-2-enoate (intermediate 19, 1.389 g) in dry dichloromethane (40 ml) was cooled to 0° C. and treated with carbon tetrabromide (2.3 g) followed by, in small portions, triphenylphosphine (1.82 g). The resulting solution was stirred thus overnight, then poured into dichloromethane/water and the organic phase separated and washed with more water, brine and dried over sodium sulfate then evaporated in vacuo. The isolated product was further purified by flash column chromatography using cyclohexane:ethyl acetate (9:1) as an eluent which gave the title compound as a white solid.

HPLC Rt=3.8 minutes.

Intermediate 21:

{4-[(1E)-3-ethoxy-3-oxoprop-1-enyl]-3-methylbenzyl}(triphenyl)phosphonium bromide.

A solution of ethyl(2E)-3-[4-(bromomethyl)-2-methylphenyl]prop-2-enoate (intermediate 20, 1.494 g) in toluene (30 ml) was stirred and treated with triphenylphosphine (1.52 g) and then heated at reflux for 2 hours then at 21° C. overnight. More triphenylphosphine (0.5 g) was then added and the reaction heated at reflux for a further 5 hours. The mixture was then allowed to cool and filtered to give the title compound as a white solid.

HPLC Rt=3.0 minutes.

Intermediate 22:

methyl 5-bromo-2-methyl-3-furoate

Bromine (2.0 ml) was added drop-wise to a mixture of methyl 2-methyl-3-furancarboxylate (5.0 g) in 1,4-dioxane (35 ml) stirred at 0° C. Stirring was continued at 0° C. for 2 hours and then at ambient temperature for 18 hours. Saturated aqueous sodium thiosulfate was added to the reaction mixture which was then extracted with ethyl acetate. The organic layer was dried with brine and over magnesium sulfate. The product isolated after evaporation of the solvent was further purified by flash column chromatography using cyclohexane:ethyl acetate (19:1) as eluent to give the title compound as a yellow oil.

HPLC Rt=3.3 min

Intermediate 23:

methyl 2-methyl-5-[4-trifluoromethyl)phenyl]-3-furoate

To a solution of methyl 5-bromo-2-methyl-3-furoate (intermediate 22, 0.7 g) and 4-trifluoromethylbenzene boronic acid (0.64 g,) in ethyleneglycol dimethyl ether (15 ml) was added sodium carbonate (0.84 g), tetrakis(triphenylphosphine)palladium (0) (0.130 g) and water (7.5 ml). The mixture was heated at reflux under nitrogen. After 3 hours the reaction was allowed to cool and was concentrated. The residue was partitioned between water and ethyl acetate; the organic solution was taken and were dried with brine and over $MgSO_4$, and concentrated. The product isolated after evaporation of the solvent was further purified by flash column chromatography using cyclohexane:ethyl acetate (14:1) as eluent to give the title compound as a white solid.

HPLC Rt=4.0 minutes

Intermediate 24:

{2-methyl-5-[4-(trifluoromethyl)phenyl]-3-furyl}methanol

A solution of methyl 2-methyl-5-[4-(trifluoromethyl)phenyl]-3-furoate (intermediate 23, 0.27 g) in tetrahydrofuran (10 ml) stirred at 0° C. under a nitrogen atmosphere was treated with 1M lithium aluminium hydride in ether (1.0 ml). The reaction mixture was stirred at this temperature for 4 hours and then water (2 ml) and 2M aqueous sodium hydroxide (2 ml) added. The reaction mixture was further diluted with water; extracted with ethyl acetate and the organic solution extracted with water and dried with brine and over sodium sulfate and concentrated. The product isolated after evaporation of the solvent was further purified by Biotage™ chromatography using a mixture of petroleum ether:ethyl acetate (1:1) as eluent to give the title compound as a white solid.

HPLC Rt=3.6 minutes

Intermediates 25–29

The following intermediates were prepared by methods analogous to those described for the preparation of intermediate 24.

Intermediate 25:

{3-methyl-5-[4-(trifluoromethyl)phenyl]-2-furyl}methanol

Prepared from methyl 5-bromo-2-methyl-3-furoate (D. W Knight et. al., J. Chem. Soc. Perkin Trans. 1 1981, (3) 679–683

$^1$H NMR (CDCl$_3$) δ 7.8 (d, 2H), 7.6 (d, 2H), 6.6 (s, 1H), 4.6 (s, 2H), 2.1 (s, 3H)

Intermediate 26:

{5-[4-(trifluoromethyl)phenyl]-2-furyl}methanol

Prepared from commercially available methyl 5-bromo-2-furoate.

HPLC Rt=3.3 minutes

Intermediate 27:

{5-[4-(trifluoromethyl)phenyl]-3-furyl}methanol

Prepared from 5-bromo-3-furancarboxylic acid, methyl ester (G. Johansson et al J. Med. Chem. 1997, 40(23), 3804–3819)

HPLC Rt=3.4 minutes

Intermediate 28:

{5-[4-(trifluoromethyl)phenyl]thien-2-yl}methanol

Prepared from commercially available 5-bromo-2-thiophenecarboxaldehyde.

HPLC Rt=3.6 minutes

Intermediate 29:

{5-[4-(trifluoromethyl)phenyl]thien-3-yl}methanol

Prepared from commercially available 5-bromo-3-thiophenecarboxaldehyde (via intermediate 37)

HPLC Rt=3.6 minutes

Intermediate 30:

5-(4-chlorophenyl)-3-hydroxymethyl-2-trifluoromethylfuran

A mixture of 5-(4-chlorophenyl)-2-(trifluoromethyl)furan-3-carboxylic acid (0.30 g) in tetrahydrofuran (10 ml) stirred under a nitrogen atmosphere at 0° C. was treated with a 1M solution of borane in tetrahydrofuran (10.33 ml) and the reaction stirred at room temperature for 2 hours. The reaction was cooled to 0° C.; treated with methanol (4 ml) and after 15 minutes the reaction mixture was evaporated. The residue was purified by SPE (Si cartridge) sequentially using dichloromethane, chloroform and chloroform:ether (9:1) as eluents to give the title compound as a white solid.

HPLC Rt=3.8 minutes

Intermediates 31 and 32 were prepared by an analogous method to that used to prepare intermediate 30

Intermediate 31:

{2-(trifluoromethyl)-5-[4-(trifluoromethyl)phenyl]-3-furyl}methanol

Prepared from commercially available 5-(4-trifluoromethylphenyl)-2-(trifluoromethyl)furan-3-carboxylic acid HPLC Rt=3.8 minutes Intermediate 32:

{2-methyl-5-[4-chlorophenyl]-3-furyl}methanol

Prepared from commercially available 5-(4-chlorophenyl)-2-methylfuran-3-carboxylic acid HPLC Rt=3.5 minutes Intermediate 33

3-(dimethylamino)-1-[4-(trifluoromethyl)phenyl]but-2-en-1-one

A mixture of 4'-(trifluoromethyl)acetophenone (9.8 g) and N-(1,1-dimethoxyethyl)-N,N-dimethylamine (8.2 g) was heated at 112° C. overnight, under nitrogen. The reaction mixture was cooled and concentrated giving an orange solid. Trituration with diethyl ether gave the title compound as a yellow solid $^1$H NMR (CDCl$_3$) δ 7.9(d, 2 H), 7.6 (d, 2 H), 5.6(s, 1 H), 3.1 (s, 6 H), 2.7(s, 3 H)

Intermediate 34

N-{3-chloro-1-methyl-3-[4-(trifluoromethyl)phenyl]prop-2-enylidene}-N-methylmethanaminium hexafluorophosphate A solution of 3-(dimethylamino)-1-[4-(trifluoromethyl)phenyl]but-2-en-1-one (intermediate 33, 2.6 g) in dichloromethane (25 ml) was treated with phosphorous oxychloride (1.5 g) at ambient temperature and the mixture stirred for 30 minutes. Solvent was removed in vacuo and the residue treated with a solution of sodium hexafluorophosphate (3.4 g) in methanol (40 ml). The title compound was isolated by filtration and dried in vacuo at ambient temperature.

$^1$H NMR (DMSO) δ 8.1(d, 2 H), 7.9 (d, 2 H), 7.6(s, 1H), 3.7(s, 3 H), 3.6(s, 3 H), 2.7(s, 3 H)

Intermediate 35 ethyl 3-methyl-5-[4-(trifluoromethyl)phenyl]thiophene-2-carboxylate

Sodium hydride (60% dispersion in mineral oil, 0.528 g) was added to dry ethanol (20 ml), N-{3-chloro-1-methyl-3-[4-(trifluoromethyl)phenyl]prop-2-enylidene}-N-methyl-methanaminium hexafluorophosphate (intermediate 34, 2.8 g) was added followed by ethyl thioglycolate (0.79 g) and the mixture heated at 110° C. for 2 hours under nitrogen. The cooled mixture was concentrated in vacuo and the residue partitioned between water and diethyl ether. The organic layer was collected, dried over magnesium sulphate and concentrated to give the title compound as a brown solid.

$^1$H NMR (CDCl$_3$) δ 7.7(d, 2 H), 7.6 (d, 2 H), 7.2(s, 1 H), 4.3(q, 2 H), 2.6(s, 3 H), 1.4(t, 3 H)

Intermediate 36:

{3-methyl-5-[4-trifluoromethyl)phenyl]thien-2-yl}methanol

A mixture of ethyl 3-methyl-5-[4-(trifluoromethyl)phenyl]thiophene-2-carboxylate (intermediate 35, 1.24 g) in tetrahydrofuran (10 ml), stirred under a nitrogen atmosphere, was treated with 1M lithium aluminum hydride in ether (4.5 ml) and the reaction mixture stirred at ambient temperature for 18 hours. The reaction mixture was treated with water (2 ml) and 2M aqueous sodium hydroxide (2 ml), diluted with water and then extracted twice with ethyl acetate. These solutions were sequentially washed with water, dried with brine, combined and the dried over sodium sulfate. The product isolated after evaporation of the solvent was further purified by Biotage® chromatography using a mixture of petroleum ether:ethyl acetate (5:1 and 4:1) as eluents to give the title compound as a white solid.

$^1$H NMR (CDCl$_3$) 7.7 (d, 2H), 7.6 (d, 2H), 6.8 (s, 1H), 4.7 (d, 2H), 2.5 (s, 3H), 1.8 (t, 1H).

Intermediate 37:

4-[4-(trifluoromethyl)phenyl]thiophene-2-carbaldehyde

To a solution of 3-bromothiophene-2-carboxaldehyde (2.0 g) and 3-trifluoromethylbenzene boronic acid (2.19 g) in ethylene glycol dimethyl ether (100 ml) was added sodium carbonate (2.9 g), tetrakis(triphenylphosphine) palladium (0) (0.12 g) and water (50 ml). The mixture was heated to 90° C. under nitrogen. After 18 hours the reaction was allowed to cool and was concentrated. The residue was partitioned between water and ethyl acetate; the organic solution was taken and was washed with brine and then dried (MgSO$_4$) and concentrated. The crude material was purified by SPE (Si); the product eluted with neat chloroform to furnish the title compound as a yellow solid.

$^1$H NMR (CDCl$_3$) δ 10.0 (s, 1H), 8.1 (d, 1H), 7.9 (m, 1H), 7.7 (bs, 4H)

Intermediate 38:

4-[4-(trifluoromethyl)phenyl]thiophene-2-carboxylic acid

A solution of 4-[4-(trifluoromethyl)phenyl]thiophene-2-carbaldehyde (intermediate 37, 1.23 g), t-butanol (20 ml) and 2-methyl-2-butene (10 ml) was cooled to 0° C. To this was added drop-wise, a solution of sodium chlorite (3.8 g) and sodium dihydrogen phosphate (4.03 g) in water (15 ml). After the addition was complete, the mixture was allowed to warm to room temperature and was stirred for 4 hours. The solution was then concentrated and partitioned between water and ethyl acetate. The aqueous layer was washed with a second ethyl acetate portion and the organic liquors were combined, washed with brine, then dried (MgSO$_4$). The solution was then absorbed onto silica and loaded onto a SPE (Si) cartridge. The product was eluted with neat ethyl acetate to afford the title compound as a white solid.

$^1$H NMR (CD$_3$OD) δ 8.1 (d, 1H), 8.0 (d, 1H), 7.8 (d, 2H), 7.6 (d, 2H)

Intermediate 39:

N-(tert-butyl)444-(trifluoromethyl)phenyl]thiophene-2-carboxamide

A solution of 4-[4-(trifluoromethyl)phenyl]thiophene-2-carboxylic acid (intermediate 38, 0.50 g) in thionyl chloride (4 ml) was refluxed for 3 hours. Excess thionyl chloride was then removed in vacuo and the crude acid chloride was dissolved in dichloromethane (20 ml) and cooled to 0° C. t-Butylamine (2.0 ml) was added slowly; the solution was allowed to warm to room temperature and was stirred thus overnight. The mixture was then poured into 1M aqueous potassium carbonate solution and passed through a hydrophobic frit. The concentrated product was purified by SPE (Si); the title compound eluted with 3:1 cyclohexane:ethyl acetate.

$^1$H NMR (CDCl$_3$) δ 7.7 (d, 1H), 7.6 (s, 4H), 7.6 (d, 1H), 5.8 (bs, 1H), 1.5 (s, 9H)

Intermediate 40:

N-(tert-butyl)-N,3-dimethyl-4-[4-(trifluoromethyl)phenyl]thiophene-2-carboxamide A solution of N-(tert-butyl)-4-[4-(trifluoromethyl)phenyl] thiophene-2-carboxamide (intermediate 39, 0.20 g) in tetrahydrofuran (50 ml) was cooled to −78° C. under nitrogen. n-Butyllithium (1.6M in hexanes, 840 µl) was added dropwise and the mixture was left to stir for 30 minutes. After this time, methyl iodide (380 µl) in tetrahydrofuran (10 ml) was added slowly and the reaction was stirred at −78° C. for 1 hour. After this time, the reaction was allowed to warm to room temperature and was left to stir for 24 hours. The reaction was then quenched with wet tetrahydrofuran, then water and 2M aqueous sodium hydroxide solution were added. The tetrahydrofuran was removed in vacuo and the aqueous mixture was added to ethyl acetate. The organic solution was taken, washed with water, brine and then was dried (magnesium sulfate) and concentrated. This furnished the title compound as an off-white crystalline solid.

$^1$H NMR (CDCl$_3$) δ 7.7 (d, 2H), 7.5 (d, 2H), 7.3 (s, 1H), 3.0 (s, 3H), 2.2 (s, 3H), 1.5 (s, 9H)

Intermediate 41:

{3-methyl-4-[4-(trifluoromethyl)phenyl]thien-2-yl}methanol n-Butyllithium (1.6M in hexanes, 1.1 ml) was added dropwise to a mixture of 1M diisobutylaluminium hydride in cyclohexane (1.77 ml) and tetrahydrofuran at 0° C. under nitrogen. This mixture was allowed to stir for 30 minutes then was added to a cooled (0° C.) solution of N-(tert-butyl)-N,3-dimethyl-4-[4-(trifluoromethyl)phenyl]thiophene-2-carboxamide (intermediate 40, 0.210 g) in tetrahydrofuran (2.5 ml) under nitrogen. After 1.5 hours, a solution of sodium borohydride (0.68 g) in ethanol (5 ml) was added and the reaction was allowed to warm to room temperature. After 2 hours, the reaction was quenched with wet tetrahydrofuran then 2M aqueous hydrochloric acid was added and the mixture was stirred for 15 minutes. Ether was added and the water layer removed. The aqueous was extracted with 2 further portions of ether then the combined organic solution was washed with brine then dried (MgSO$_4$) and concentrated. The crude product was purified by SPE (silica cartdrige) using cyclohexane:ethyl acetate (3:1) as eluent to furnish the title compound as a colourless oil.

$^1$H NMR (CDCl$_3$) δ 7.7 (d, 2H,), 7.5 (d, 2H,), 7.2 (s, 1H), 4.6 (s, 2H), 2.2 (s, 3H)

Intermediate 42:

{2-methyl-5-[4-(trifluoromethyl)phenyl]thien-3-yl}methanol

This compound was prepared from 5-bromothiophene-3-carboxaldehyde by a procedure analogous to that used to prepare intermediate 41 (intermediates 37–41)

HPLC Rt=3.7 minutes

Intermediate 43:

ethyl 3-bromomethyl)-5-[4-(trifluoromethyl)phenyl]thiophene-2-carboxylate

Ethyl 3-methyl-5-[4-(trifluoromethyl)phenyl]thiophene-2-carboxylate (intermediate 35, 0.100 g) and sodium bromate (0.144 g) were suspended in a mixture of cyclohexane and water (1:1 v/v, 4 ml). To this was added a solution sodium bisulfite (0.99 g) in water (1 ml). The mixture was stirred for 2 hours, quenched with 1M sodium thiosulfate solution, then extracted with ethyl acetate. The organic layer was taken and washed with water, sodium thiosulfate and dried with brine and over MgSO$_4$ and concentrated to give the title compound as a white crystalline solid.

HPLC Rt=4.3 minutes

Intermediate 44:

methyl 2-(bromomethyl)-5-[4-(trifluoromethyl)phenyl]-3-furoate

A solution of sodium bromate (8.14 g) in water (27 ml) was treated with a suspension of methyl 2-methyl-5-[4-(trifluoromethyl)phenyl]-3-furoate (intermediate 23, 5.12 g) in cyclohexane (36 ml). The system was cooled to <10° C. in ice/water bath and treated with a solution of sodium hydrogen sulfite (9.4 g) in water (54 ml) in a drop-wise manner over 30 minutes. The reaction was allowed to warm up to 10° C. for 2 hours and then poured into diethylether (400 ml) and washed with fresh water. The organic layer was washed with 10% sodium thiosulfite solution and dried over magnesium sulfate. The crude product isolated by evaporation, was pre-adsorbed onto silica and purified by flash column chromatography using 39:1 cyclohexane:ethyl acetate as eluent to give the title compound as a white powder.

HPLC Rt=4.1 minutes

Intermediate 45:

ethyl 3[(benzylthio)methyl]-5-[4-(trifluoromethyl)phenyl]thiophene-2-carboxylate A solution of ethyl 3-(bromomethyl)-5-[4-(trifluoromethyl)phenyl]thiophene-2-carboxylate (intermediate 43, 0.100 g) and benzyl mercaptan (0.30 g) in acetonitrile (10 ml) was treated with potassium carbonate (0.46 g) and the mixture stirred at ambient temperature overnight. The reaction mixture was partitioned between ethyl acetate and water the organic layer as collected, dried over magnesium sulfate and concentrated. The residue was purified by SPE (Si cartridge) eluting initially with cyclohexane:chloroform (5:1) and then cyclohexane:chloroform (1:3) to give the title compound as a colourless oil.

HPLC Rt=4.5 minutes

Intermediate 46:

{3-[(benzylthio)methyl]-5-[4-(trifluoromethyl)phenyl]thien-2-yl}methanol

A solution of ethyl 3-[(benzylthio)methyl]-5-[4-(trifluoromethyl)phenyl]thiophene-2-carboxylate (intermediate 45, 0.87 g) in dry tetrahydrofuran (5 ml) was cooled to 0° C. and 1M lithium aluminium hydride solution in diethyl, ether (0.299 ml) added. The reaction mixture as stirred with cooling for 3 hours. Water (0.5 ml) was added drop-wise followed by 2M hydrochloric acid (0.5 ml), the further water (50 ml), the resulting mixture was extracted twice with ethyl acetate, the extracts were combined, dried over magnesium sulfate and concentrated. The residue was purified by SPE (Si cartridge) eluting initially with cyclohexane:chloroform (1:1) and then chloroform to give the title compound as a white solid.

HPLC Rt=4.0 minutes

Intermediates 47–53 were prepared from intermediate 43 by methods analogous to those described above for the preparation of intermediate 46

Intermediate 47:

{3-(phenoxymethyl)-5-[4-(trifluoromethyl)phenyl]thien-2-yl}methanol

Prepared from intermediate 43 and phenol

HPLC Rt=3.9 minutes

Intermediate 48:

{3-[(isopropylthio)methyl]-5-[4-(trifluoromethyl)phenyl]thien-2-yl}methanol

Prepared from intermediate 43 and isopropylthiol

HPLC Rt=4.0 minutes

Intermediate 49:

-{3-{[(4'-methyl-1,1'-biphenyl-4-yl)oxy]methyl}-5-[4-(trifluoromethyl)phenyl]thien-2-yl}methanol Prepared from intermediate 43 and 4-hydroxy-4'-methyl-1,1'-biphenyl HPLC Rt=4.3 minutes Intermediate 50:

{3-{[methyl(phenyl)amino]methyl}-5-[4-trifluoromethyl)phenyl]thien-2-yl}methanol Prepared from intermediate 43 and N— methyl aniline HPLC Rt=3.4 minutes Intermediate 51:

{3-{[4-(trifluoromethyl)phenoxy]methyl}-5-[4-(trifluoromethyl)phenyl]thien-2-yl}methanol Prepared from intermediate 43 and 4-(trifluoromethyl) phenol HPLC Rt=4.0 minutes Intermediate 52:

-{3-{[4-(2-phenylethyl)phenoxy]methyl}-5-[4-(trifluoromethyl)phenyl]thien-2-yl}methanol Prepared from intermediate 43 and 4[2-(phenylethyl)] phenol HPLC Rt=4.3 minutes Intermediate 53:

{3-ethyl-5-[4-(trifluoromethyl)phenyl]thien-2-yl}methanol

Prepared from intermediate 43 and methylmagnesium bromide

HPLC Rt=3.2 minutes

Intermediates 54–42 were prepared from intermediate 44 by methods analogous to those described above for the preparation of intermediate 46

Intermediate 54:

{2-[(benzylthio)methyl]-5-[4-trifluoromethyl)phenyl]-3-furyl}methanol

Prepared from intermediate 44 and benzyl mercaptan

HPLC Rt=4.0 minutes

Intermediate 55:

{2-(phenoxymethyl)-5-[4-trifluoromethyl)phenyl]-3-furyl}methanol

Prepared from intermediate 44 and phenol $^1$H NMR (CDCl$_3$) δ 7.79 (d, 2H), 7.65 (d, 2H), 7.35 (t, 2H), 7.0 (m, 3H), 6.83 (s, 1H), 5.12 (s, 2H), 4.65 (d, 2H), Intermediate 56:

{2-[(isopropylthio)methyl]-5-[4-(trifluoromethyl)phenyl]-3-furyl}methanol

Prepared from intermediate 44 and isopropylthiol $^1$H NMR (CDCl$_3$) δ 7.75 (d, 2H), 7.63 (d, 2H), 6.8 (s, 1H), 7.58 (d, 2H), 7.87 (s, 2H), 2.95 (m, 1H), 1.90 (t, 1H), 1.31 (d, 6H)

Intermediate 57:

{2-{[methyl(phenyl)amino]methyl}-5-[4-trifluoromethyl)phenyl]-3-furyl}methanol

Prepared from intermediate 44 and N-methyl aniline $^1$H NMR (CDCl$_3$) δ 7.74 (d, 2H), 7.65 (d, 2H), 6.34 (m, 3H), 6.0 (d, 2H), 5.9 (t, 1H), 5.8 (s, 1H)

Intermediate 58:

{2-{[(2-furylmethyl)thio]methyl}-5-[4-(trifluoromethyl)phenyl]-3-furyl}methanol

Prepared from intermediate 44 and furan-2-methanethiol tlc: cyclohexane:ethylacetate (1:1) R$_f$=0.42

Intermediate 59:

{2-{[(3,5-dimethylphenyl)thio]methyl}-5-[4-trifluoromethyl)phenyl]-3-furyl}methanol Prepared from intermediate 44 and 3,5-dimethylthiophenol tlc: cyclohexane:ethylacetate (1:1) R$_f$=0.52

Intermediate 60:

{2-{[(2,4-difluorophenyl)thio]methyl}-5-[4-trifluoromethyl)phenyl]-3-furyl}methanol Prepared from intermediate 44 and 2,4-difluorothiophenol tlc: cyclohexane:ethyl acetate (1:1) R$_f$=0.49

Intermediate 61:

{2-{[(1H-benzimidazol-2-ylmethyl)thio]methyl}-5-[4-(trifluoromethyl)phenyl]-3-furyl}methanol Prepared from intermediate 44 and benzimidazole-2-methanethiol tlc: dichloromethane:methanol:"880" ammonia (196:3:1) R$_f$=0.14

Intermediate 62:

({3-(methoxycarbonyl)-5-[4-(trifluoromethyl)phenyl]-2-furyl}methyl)(triphenyl)phosphonium bromide Methyl 2-bromomethyl-5-[4-(trifluoromethyl)phenyl]-3-furoate (intermediate 44, 0.20 g) was dissolved in toluene (3 ml) treated with triphenylphosphine (0.159 g) and heated to reflux for 1 hour. The reaction was allowed to cool and the white precipitate was collected by filtration, washed with fresh toluene to give the title compound as a white powder.

HPLC Rt=4.0 minutes

Intermediate 63:

methyl2-[(E)-2-pyridin-4-ylethenyl]-5-[4-(trifluoromethyl)phenyl]-3-furoate hydrochloride ({3-(Methoxycarbonyl)-5-[4-(trifluoromethyl)phenyl]-2-furyl}methyl)(triphenyl)phosphonium bromide (intermediate 62, 0.200 g) was suspended in dry tetrahydrofuran (4 ml). Potassium t-butoxide (0.40 g) was added and the bright orange reaction mixture was allowed to stir for 25 minutes at ambient temperature. 4-Pyridinecarboxaldehyde (0.034 ml) was added and the reaction allowed to stir for 4.5 hours. The solvent was removed by evaporation and the residue partitioned between chloroform and water. The organic layer was dried using a hydrophobic frit, re-concentrated to a small volume under reduced pressure and loaded onto SPE (Si cartridge) eluting with a gradient from 25:1 to 4:1 cyclohexane:ethyl acetate. The resulting material was acidified with 2M aqueous hydrochloric acid, concentrated under reduced pressure, then triturated with diethyl ether to give the title compound as a yellow powder.

$^1$H NMR (MeOD) δ 8.81 (d, 2H), 8.3 (d, 1H), 8.14 (d, 2H), 7.85 (d, 2H), 7.75 (d, 1H), 7.52 (s, 1H), 4.0 (s, 3H)

Intermediate 64:

methyl 2-(2-pyridin-4-ylethyl)-5-[4-(trifluoromethyl)phenyl]-3-furoate hydrochloride Methyl 2-[(E)-2-pyridin-4-ylethenyl]-5-[4-(trifluoromethyl)phenyl]-3-furoate hydrochloride (intermediate 62, 0.88 g) was dissolved in ethyl alcohol (5 ml) and added to palladium on carbon (wet Degussa type E101 NE/W). The reaction mixture was stirred at ambient temperature under a hydrogen atmosphere for 4 hours. The catalyst was removed by filtration through Harbolite J2 and the filtrate concentrated to give the title compound as pale yellow sticky solid.

$^1$H NMR (MeOD) δ 8.63 (d, 2H), 7.89 (d, 2H), 7.73 (d, 2H), 7.61 (d, 2H), 7.09 (s, 1H), 3.73 (s, 3H), 3.5 (t, 2H), 3.35 (t, 2H).

Intermediate 65:

{2-(2-pyridin ylethyl)-5-[4-(trifluoromethyl)phenyl]-3-furyl}methanol

Methyl 2-(2-pyridin-4-ylethyl)-5-[4-(trifluoromethyl)phenyl]-3-furoate hydrochloride (intermediate 64, 0.69 g) was suspended in dry tetrahydrofuran (4 ml), cooled in ice and treated with 1M lithium aluminium hydride solution in diethyl ether (0.334 ml). The reaction mixture was allowed to warm up to room temperature and stirred for 3 hours. 1M Sodium hydroxide solution (2 ml) was added and the reaction stirred for a further 30 minutes. The reaction mixture was concentrated, the residue was partitioned between chloroform and aqueous sodium hydroxide. The organic layer through hydrophobic frit and finally concentrated under reduced pressure to give the title product as colourless gum.

$^1$H NMR (CDCl3) δ 8.50 (d, 2H), 7.68 (d, 2H), 7.61 (d, 2H), 7.15 (d, 2H), 6.71 (s, 1H), 4.34 (s, 2H), 3.06 (s, 4H)

Intermediates 65–67 were prepared by methodology analogous to that described above for the preparation of intermediate 64

Intermediate 66:

{2-[2-(4-methylphenyl)ethyl]-5-[4-(trifluoromethyl)phenyl]-3-furyl}methanol prepare from intermediate 62 and 4-methylbenzaldehyde $^1$H NMR (CDCl$_3$) δ 7.75 (d, 2H), 7.65 (d, 2H), 7.1 (d, 2H), 7.0 (d, 2H), 6.7 (s, 1H), 4.18 (s, 2H), 2.96 (m, 4H), 2.30 (s, 3H)

Intermediate 67:

{2-isopentyl-5-[4-(trifluoromethyl)phenyl]-3-furyl}methanol

Prepared from intermediate 62 and 2-methylpropanal $^1$H NMR (CDCl$_3$) δ 7.71 (d, 2H), 7.62 (d, 2H), 6.78 (s, 1H), 4.55 (s, 2H), 2.70 (t, 2H), 1.58 (m, 3H), 0.96 (d, 6H)

Intermediate 68:

{2-isobutyl-5-[4-(trifluoromethyl)phenyl]-3-furyl}methanol

Prepared from intermediate 62 and propanone $^1$H NMR (CDCl$_3$) δ 7.75 (d, 2H), 7.61 (d, 2H), 6.80 (s, 1H), 4.50 (s, 2H), 2.60 (d, 2H), 2.04 (sept, 1H), 0.98 (d, 6H)

Intermediate 69:

ethyl[2-methyl-4-(2-thien-2-ylethoxy)phenoxy]acetate

A solution of ethyl(4-hydroxy-2-methylphenoxy)acetate (intermediate 7, 1.05 g) and 2-(2-thienyl)ethanol (0.64 g) in dry tetrahydrofuran was treated with tri-n-butyl phosphine (1.2 g) and azodicarbonyldimorpholide (1.53 g) and the mixture stirred at ambient temperature for 3 days. The reaction mixture was concentrated and the residue partitioned between ethyl acetate and water. The organic layer was collected, dried over sodium sulfate, concentrated and the residue purified by SPE (Si cartridge) eluting with cyclohexane:ethyl acetate (20:1) to give the title compound as a colourless oil.

¹H NMR (CDCl₃) δ 7.15 (dd, 1H), 6.95 (dd, 1H), 6.9 (dd, 1H), 6.75 (s, 1H), 6.65 (s, 2H), 4.55 (s, 2H), 4.25 (q, 2H), 4.1 (t, 2H), 3.25 (t, 2H), 2.25 (s, 3H), 1.3 (t, 3H)

Intermediate 70:
ethyl{4-[2-(5-bromothien-2-yl)ethoxy]-2-methylphenoxy}acetate

A solution of ethyl[2-methyl-4-(2-thien-2-ylethoxy)phenoxy]acetate (intermediate 69, 0.306 g) in acetic acid (5 ml) was treated with bromine (0.180 g) at ambient temperature and the mixture stirred for 15 minutes. The mixture was poured into water and the resulting suspension extracted with diethyl ether. The organic layer was separated, dried over sodium sulfate and concentrated to give the title compound as a colourless oil.

¹H NMR (CDCl₃) δ 6.9 (d, 2H), 6.75 (d, 1H), 6.65 (d, 3H), 4.55 (s, 3H), 4.25 (q, 2H), 4.1 (t, 2H), 3.2 (t, 2H), 2.3 (s, 3H), 1.3 (t, 3H)

Intermediate 71:
5-4-chlorophenyl)-2-methyl-3-furaldehyde

A mixture 5-(4-chlorophenyl)-3-hydroxymethyl-2-methylfuran (intermediate 32, 0.70 g) in chloroform (50 ml) was treated with manganese dioxide (5.60 g) and the reaction mixture stirred for 1.20 hours. The reaction was filtered through Celite™ and the filtrate evaporated to give the title compound as a colourless solid.

¹H NMR (CDCl₃) δ 10.0 (s, 1H), 7.6 (d, 2H), 7.4 (d, 2H), 6.9 (s, 1H), 2.7 (s, 3H)

Intermediates 72–74 were prepared by methodology analogous to that described above for preparation of intermediate 71.

Intermediate 72:
5-[4-trifluoromethyl)phenyl]-2-methyl-3-furaldehyde
Prepared from intermediate 24
¹H NMR (CDCl₃) δ 10.0 (s, 1H), 7.8 (d, 2H,), 7.7 (d, 2H,), 7.0 (s, 1H), 2.7 (s, 3H).

Intermediate 73:
5-(4-chlorophenyl)-2-(trifluoromethyl)-3-furaldehyde
Prepared from intermediate 30
HPLC Rt=4.4 minutes Intermediate 74:
3-methyl-5-[4-(trifluoromethyl)phenyl]thiophene-2-carbaldehyde
Prepared from intermediate 36
HPLC Rt=2.7 minutes Intermediate 75:
2-(3-methylthien-2-yl)-1,3-dioxolane A mixture of 3-methylthiophene carboxaldehyde (6.8 g), ethylene glycol (10 ml) and p-toluenesulfonic acid (0.30 g) in toluene (125 ml) was heated at reflux for 18 hours. The reaction mixture was cooled; extracted with 2M aqueous sodium carbonate and then dried with brine and over magnesium sulfate. Analysis of the crude product indicated that the reaction was incomplete so the crude material was re-subjected to the ketalisation conditions as outlined above. The crude material isolated after reprocessing was distilled under reduced pressure (1 mmHg) to give the title compound as a yellow oil.

HPLC Rt=2.8 minutes

Intermediate 76:
tributyl[5-(1,3-dioxolan-2-yl)-4-methylthien-2-yl]stannane

A mixture of 2-(3-methylthien-2-yl)-1,3-dioxolane (intermediate 75, 1.5 g) in tetrahydrofuran (50 ml), stirred at −60° C. under a nitrogen atmosphere, was treated drop-wise with 1.6M n-butyl lithium in hexanes (6.1 ml). The reaction mixture was stirred at this temperature for 1 hour and tributyltin chloride (2.6 ml) was added; stirring was continued at −60° C. for 1 hour and then the reaction allowed to warm to ambient temperature. After 18 hours the reaction mixture was diluted with diethylether and this mixture was extracted with water and the ether layer dried with brine and over magnesium sulfate. The product isolated after evaporation of the solvent was further purified by flash column chromatography using cyclohexane:ethyl acetate (50:1) as eluent to give the title compound as a yellow oil.

HPLC Rt=4.9 minutes

Intermediate 77:
3-methyl-5-(tributylstannyl)thiophene-2-carbaldehyde

A mixture of tributyl[5-(1,3-dioxolan-2-yl)4-methylthien-2-yl]stannane (intermediate 76, 2.92 g), 1M aqueous hydrochloric acid (3 ml) and tetrahydrofuran (10 ml) was stirred at reflux for 30 minutes. The reaction mixture was cooled, extracted thrice with diethylether. The organic solutions were combined, extracted with saturated sodium bicarbonate and dried with brine and over magnesium sulfate. The product isolated after evaporation of the solvent was further purified by flash column chromatography using cyclohexane:ethyl acetate (50:1) as eluent to give the title compound as a yellow oil.

HPLC Rt=0.8 minutes

Intermediate 78:
3-methyl-5-[5-trifluoromethyl)pyridin-2-yl]thiophene-2-carbaldehyde A mixture of 2-bromo-4-trifluoromethylpyridine (0.073 g), tetrakis(triphenylphosphine)palladium (0) (0.019 g) and silver oxide (0.074 g) in N,N-dimethylformamide was heated at 100° C. for 5 minutes. A solution of 3-methyl-5-(tributylstannyl)thiophene-2-carbaldehyde (intermediate 77, 0.095 g) in N,N-dimethylformamide (2 ml) was added and the reaction stirred for 5 minutes at 100° C. The reaction mixture was cooled, N,N-dimethylformamide removed and a solution of the residue in dichloromethane filtered through Celite® 545. The solvent was evaporated and the residue further purified by flash column chromatography using cyclohexane:ethyl acetate (50:1) as eluent to give the title compound as a yellow oil.

HPLC Rt=3.6 minutes

Intermediate 79:
{3-methyl-5-[5-(trifluoromethyl)pyridin-2-yl]thien-2-yl}methanol A mixture of 3-methyl-5-[5-(trifluoromethyl)pyridin-2-yl]thiophene-2-carbaldehyde (intermediate 78, 0.144 g) in tetrahydrofuran (10 ml) and water (15 ml) was treated with sodium borohydride (0.03 g). The reaction was stirred at room temperature for 30 minutes, extracted with ethyl acetate and the organic layer washed with water and dried with brine and over magnesium sulfate. The title compound was isolated after removal of the desiccant and evaporation of the solvent.

HPLC Rt=3.4 minutes

Intermediate 80:
[3-methyl-5-(tributylstannyl)thien-2-yl]methanol
Prepared using a method analogous to the preparation of intermediate 79 using intermediate 77.
HPLC Rt=4.8 minutes Intermediate 81:
ethyl(2-methyl-4-{[3-methyl-5-(tributylstannyl)thien-2-yl]methoxy}phenoxy)acetate
The title compound was prepared from intermediates 7 and 80 using a procedure analogous to that used for the preparation of intermediate 69.
HPLC Rt=5.1 minutes Intermediate 82:

5-bromo-3-methylthiophene-2-carbaldehyde

A solution of 3-methyl-thiophene-2-carboxaldehyde (12.0 g) in chloroform (50 ml) was added drop-wise to bromine (5.1 ml) in chloroform over 30 minutes and then heated to 100° C. for 140 minutes. The reaction mixture was diluted with chloroform and washed with 10% aqueous sodium thiosulfate solution, saturated aqueous bicarbonate solution and water. The organic solution was dried over magnesium sulfate and concentrated. The product isolated after evaporation of the solvent was further purified by vacuum distillation (122° C., 4 mbar) to give the title compound as a green oil.

$^1$H NMR (CDCl$_3$) δ 9.9 (s, 1H), 6.95 (s, 1H), 2.55 (s, 3H)

Intermediate 83:

(5-bromo-3-methylthien-2-yl)methanol

A mixture of 1-(5-bromo-3-methylthien-2-yl)ethanone (intermediate 82, 5.13 g) in ethanol (50 ml) was treated with sodium borohydride (0.947 g). The reaction was stirred at 0° C. for 60 minutes and warmed to room temp for 30 minutes. 2M Aqueous hydrochloric acid was added and the reaction mixture was extracted with ethyl acetate twice. The organic solutions were combined and dried with brine and over magnesium sulfate. The title compound was isolated after removal of the desiccant and evaporation of the solvent.

HPLC Rt=3.0 minutes

Intermediate 84:

ethyl{4-[(5-bromo-3-methylthien-2-yl)methoxy]-2-methylphenoxy}acetate

The title compound was prepared from intermediates 7 and 83 using a procedure analogous to that used for the preparation of intermediate 69.

HPLC Rt=4.1 minutes.

Intermediate 85:

[5-(4-chlorophenyl)-2-(trifluoromethyl)-3-furyl]acetonitrile

To a solution of 1M potassium tert-butoxide solution in tetrahydrofuran (5.9 ml) in dry ethylene glycol dimethyl ether (80 ml) at −78° C. under nitrogen was added TOSMIC (0.61 g) in ethylene glycol dimethyl ether (10 ml) followed by -5-(4-chlorophenyl)-2-(trifluoromethyl)-3-furaldehyde (intermediate 73, 0.770 g) in dry ethylene glycol dimethyl ether (20 ml). The bright red solution was stirred at −70 to −50° C. for 1.5 hours. Dry methanol (20 ml) was then added and the solution was allowed to warm to room temperature. After 1 hour the mixture was heated to reflux for 30 minutes then allowed to cool back to room temperature. The solution was concentrated then partitioned between dichloromethane, water and acetic acid (few drops). The aqueous portion was taken and washed a second time with dichloromethane. The combined organics were washed with 1M aqueous potassium carbonate solution then dried (MgSO$_4$) and concentrated. The crude material was purified by SPE (Si): the product was eluted with cyclohexane:chloroform (1:1) and concentrated to form yellow crystals.

$^1$H NMR (CDCl$_3$) δ 7.58 (d, 2H), 7.34 (d, 2H), 6.74 (s, 1H), 3.69 (s, 2H)

Intermediate 86:

methyl[5-(4-chlorophenyl)-2-trifluoromethyl)-3-furyl]acetate

A solution of [5-(4-chlorophenyl)-2-(trifluoromethyl)-3-furyl]acetonitrile (intermediate 85, 0.171 g) in methanol (20 ml) was cooled to <−40° C. under nitrogen. Hydrogen chloride gas was bubbled through for ~10 minutes until the temperature had stopped rising. This mixture was stored at −20° C. overnight. The solution was then concentrated and water (20 ml) was added. This mixture was heated to reflux for 20 minutes then allowed to cool to room temperature. Ethyl acetate was added; the organic layer was separated and washed with water and brine then dried (MgSO$_4$) and concentrated. The crude material was passed down a SPE (Si): the product was eluted using cyclohexane:chloroform (1:1) and concentrated to form a yellow oil.

$^1$H NMR (CDCl$_3$) δ 7.56 (d, 2H), 7.32 (d, 2H), 6.66 (s, 1H), 3.68 (s, 3H), 3.59 (s, 2H)

Intermediate 87:

2-[5-(4-chlorophenyl)-2-(trifluoromethyl)-3-furyl]ethanol 1.5 M Diisobutylaluminium hydride in toluene (0.8 ml) was added to a solution of methyl[5-(4-chlorophenyl)-2-(trifluoromethyl)-3-furyl]acetate (intermediate 86, 0.10 g) in tetrahydrofuran (5 ml) at 0° C. under nitrogen. The solution was allowed to stir thus for 2.5 hours then was quenched with methanol and allowed to warm to room temperature. Silica was added and the solvent was removed in vacuo. The crude product was purified using SPE (silica cartridge): the product was eluted using cyclohexane:ethyl acetate (5:1) and concentrated to form a colourless oil.

$^1$H NMR (CDCl$_3$) δ 7.62 (d, 2H), 7.38 (d, 2H), 6.66 (s, 1H), 3.88 (q. 2H), 2.86 (t, 2H)

Intermediate 88

{2-{[isopropyl(methyl)amino]methyl}-5-[4-(trifluoromethyl)phenyl]-3-furyl}methanol Prepared using intermediate 44 and N-methylisopropylamine. This compound was used directly without collection of analytical data for the preparation of Example 75.

Intermediate 89

{2-{[methyl(2-phenylethyl)amino]methyl}-5-[4-(trifluoromethyl)phenyl]-3-furyl}methanol Prepared using intermediate 44 and N-methylphenethylamine.

$^1$H NMR (CDCl$_3$) δ 7.70 (d, 2H), 7.62 (d, 2H), 7.27 (m, 2H), 7.18 (m, 3H), 4.55 (s, 2H), 3.75 (s, 2H), 2.85 (d, t, 2H), 2.75 (d, t, 2H), 2.40 (s, 3H)

Intermediate 90

{2-{[cyclohexyl(methyl)amino]methyl}-5-[4-(trifluoromethyl)phenyl]-3-furyl}methanol Prepared using intermediate 44 and N-methylcyclohexylamine.

$^1$H NMR (CDCl$_3$) δ, 7.7 (d, 2H), 7.63 (d, 2H), 6.67 (s, 1H), 4.63 (s, 2H), 2.43 (m, 1H), 2.24 (s, 3H), 1.85 (m, 4H), 1.64 (d, 1H), 1.2 (m, 4H), 1.1 (m, 2H)

Intermediate 91

{2-{[(3,5-dimethoxybenzyl)(methyl)amino]methyl}-5-[4-(trifluoromethyl)phenyl]-3-furyl}methanol Prepared using intermediate 44 and N-methyl(3,5-dimethoxy)benzylamine.

$^1$H NMR (CDCl$_3$) δ 7.70 (d, 2H), 7.62 (d, 2H), 6.68 (s, 1H), 6.55 (s, 2H), 6.40 (t, 1H), 4.60 (s, 2H), 3.78 (s, 6H), 3.64 (s, 2H), 2.34 (s, 3H)

Intermediate 92

{2-{[methyl(pyridin-3-ylmethyl)amino]methyl-5-[4-(trifluoromethyl)phenyl]-3-furyl}methanol Prepared using intermediate 44 and N-methyl(3-pyridyl)methylamine.

$^1$H NMR (CDCl$_3$) δ 8.55 (s, 2H), 7.76, (d, 1H), 7.72 (d, 2H), 7.62 (d, 2H), 7.31 (d,d, 1H), 6.69 (s, 1H), 4.61 (s, 2H), 3.79, (s, 2H), 3.67 (s, 2H), 2.30 (s, 3H)

Intermediate 93 benzyl(4-formyl-2-methylphenoxy)acetate

Prepared using a method analogous to that used for the preparation of intermediate 1 using benzyl bromoacetate and 3-methyl-4-hydoxybenzaldehyde.

¹H NMR (CDCl₃) δ 9.98 (s, 1H), 7.71 (s, 1H), 7.64 (1H, d), 7.40–7.30 (bs, 5H), 6.75 (d, 1H), 5.24 (s, 2H), 4.78 (s, 2H), 2.34 (3H, s)

Intermediate 94

(3-methylthien-2-yl)methanol

Prepared from commercially available 3-methyl-1-thiophenecarboxaldehyde.

¹H NMR (CDCl₃) δ 7.17 (1H, d), 6.83 (d, 1 Hz), 4.76 (s, 2H), 2.25 (3H, s)

Intermediate 95

[(3-methylthien-2-yl)methyl](triphenyl)phosphonium bromide

Prepared using a method analogous to that used for the preparation of intermediate 14 using intermediate 94.

¹H NMR (CDCl₃) δ 7.80–7.64 (15H, m), 7.40 (1H, m), 6.83 (d, 1H), 5.29 (2H, d), 1.52 (3H, bs)

Intermediate 96

E/Z benzyl{2-methyl-4-[2-(3-methylthien-2-yl)ethenyl]phenoxy}acetate

Sodium hydride (0.204, 60% dispersion in mineral oil) was added to anhydrous N,N-dimethylformamide (5 ml) followed by [(3-methylthien-2-yl)methyl](triphenyl)phosphonium bromide (intermediate 95, 0.2.67 g) after 10 minutes. After a further 10 benzyl(4-formyl-2-methylphenoxy)acetate (intermediate 94, 1.42 g) was added and the reaction mixture stirred at ambient temperature for 3 hours. The reaction mixture was treated with water and then the mixture extracted with ethyl acetate. The ethyl acetate solution was extracted with water, 1M aqueous hydrochloric acid, water and finally dried with brine and over sodium sulfate. The crude product remaining after this treatment was purified by Biotage® chromatography using a mixture of petroleum ether:ethyl acetate (4:1) as eluent to give the title compounds as a mixture of isomers.

HPLC Rt=4.2 and 4.3 minutes.

Intermediate 97

{2-methyl-4-[2-3-methylthien-2-yl)ethyl]phenoxy}acetic acid

Prepared from intermediate 96 using methods analogous to that used for the preparation of examples 117 and 118.

HPLC Rt=3.81 minutes

Intermediate 98

(3-methyloxetan-3-yl)methyl{2-methyl-4-[2-(3-methylthien-2-yl)ethyl]phenoxy}acetate A mixture of {2-methyl-4-[2-(3-methylthien-2-yl)ethyl]phenoxy}acetic acid (intermediate 97, 0.615 g) in dichloromethane (10 ml) was treated with WSDCI (0.608 g); DMAP (0.010 g) and 3-methyloxetane-3-methanol (0.433 g). The reaction mixture was stirred for 16 hours; extracted with water and then dried with a hydrophobic frit. The solvent was removed under reduced pressure and the residue purified by Biotage® chromatography using a mixture of petroleum ether:ethyl acetate (5:1) as eluent to give the title compound.

HPLC Rt=3.8 minutes

Intermediate 99

4-methyl-1-({2-methyl-4-[2-(3-methylthien-2-yl)ethyl]phenoxy}methyl)-2,6,7-trioxabicyclo[2.2.2]octane A mixture of (3-methyloxetan-3-yl)methyl{2-methyl-4-[2-(3-methylthien-2-yl)ethyl]phenoxy}acetate (intermediate 98, 0.673 g) in dichloromethane stirred under nitrofgen in an ice/water bath was treated with boron trifluoride etherate (0.171 ml). The reaction mixture was stirred for 4 hours at this temperature then triethylamine (0.25 ml) added. The solvent was removed and the residue purified by Biotage® chromatography using a mixture of petroleum ether:ethyl acetate (5:1) as eluent to give the title compound.

HPLC Rt=3.9 minutes

Intermediate 100 tributyl[4-methyl-5-(2-{3-methyl-4-[(4-methyl-2,6,7-trioxabicyclo[2.2.2]oct-1-yl)methoxy]phenyl}ethyl)thien-2-yl]stannane Prepared from intermediate 99 using methods analogous to that used for the preparation of intermediate 76.

¹H NMR (CDCl₃) δ 6.95–6.92 (2H, m), 6.85–6.81 (2H, m), 3.99 (8H, s), 3.00–2.95 (2H, m), 2.84–2.79 (2H, m), 2.25 (s, 3H), 2.19 (s, 3H), 1.60–1.51 (6H, m), 1.39–1.29 (6H, m), 1.09–1.04 (6H, m), 0.90 (2H, t)

Intermediate 101

2-fluoro-4-[4-methyl-5-(2-{3-methyl-4-[(4-methyl-2,6,7-trioxabicyclo[2.2.2]oct-1-yl)methoxy]phenyl}ethyl)thien-2-yl]benzonitrile A mixture of tributyl[4-methyl-5-(2-{3-methyl-4-[(4-methyl-2,6,7-trioxabicyclo[2.2.2]oct-1-yl)methoxy]phenyl}ethyl)thien-2-yl]stannane (intermediate 100, 0.037 g) and 2-fluoro-4-bromobenzonitrile (0.011 g) in tetrahydrofuran (2 ml) was treated with palladium bis(dibenzylideneacetone) (0.0035 g) and trifuranyl phosphine (0.0013 g) and the resulting mixture stirred at reflux for 3 hours. The solvent was removed and the residue purified by Biotage® chromatography using a mixture of petroleum ether:ethyl acetate (4:1) as eluent to give the title compound.

HPLC Rt=4.2 minutes

Intermediate 102

4-methyl-2-[4-(trifluoromethyl)phenyl]thiophene

To a solution of 3-methylthiophene (2.31 ml) in anhydrous THF (75 ml) at −78° C. under N₂ was added dropwise n-BuLi (1.6 M in hexanes, 15 ml). Thirty minutes after the addition was complete, the reaction mixture was allowed to warm to 0° C. and stirred for a further 30 minutes. Zinc chloride (0.5 M in THF, 48 ml) was added drop-wise, after a further 15 minutes palladium (0) tetrakis(triphenylphosphine) (100 mg) and 4-bromobenzotrifluoride (3.36 ml) were added and the reaction allowed to attain room temperature. The reaction mixture was warmed to 40° C. and stirred at this temperature for 3 hours. The reaction mixture was then cooled to room temperature and the solvents removed in vacuo. The residue was partitioned between and ether and the aqueous extract further washed with ether. The combined organic extracts were dried (MgSO₄), filtered and evaporated to yield a brown oil. Purification by Biotage® chromatography eluting with cyclohexane yielded the title compound as a white solid.

HPLC Rt=4.2 minutes

Intermediate 103

2-(4-methoxy-3-methylphenyl)-1-{3-methyl-5-[4-(trifluoromethyl)phenyl]thien-2-yl}ethanone To methanesulfonic acid (8 ml) in a flask under N₂ was added P₂O₅ (0.56 g), the resulting suspension was heated to 60° C. until a clear solution formed. The mixture was cooled to room temperature prior to addition of 4-methoxy-3-methyl-phenylacetic acid (0.3549) and 4-methyl-2-[4-(trifluoromethyl)phenyl]thiophene (intermediate 102, 0.4 g). The mixture was then heated to 60° C. for 90 minutes. The reaction mixture was cooled to room temperature and then poured into iced water. The suspension was made basic by cautious addition of NaHCO₃ and the products extracted into ethyl acetate. The combined organic extracts were dried (MgSO₄), filtered and evaporated to yield a brown oil. Purification by flash column chromatography eluting with 5% EtOAc/cyclohexane yielded the title compound as a brown gum.

HPLC Rt=4.5 minutes

Intermediate 104

2-(4-methoxy-3-methylphenyl)-2-methyl-1-{3-methyl-5-[4-(trifluoromethyl)phenyl]thien-2-yl}propan-1-one To a suspension of sodium hydride (60% dispersion in mineral oil, 0.105 g) in anhydrous 1,2-dimethoxyethane (1 ml), under nitrogen, was added methyl iodide (0.164 ml). A solution of 2-(4-methoxy-3-methylphenyl)-1-{3-methyl-5-[4-(trifluoromethyl)phenyl]thien-2-yl}ethanone (intermediate 103, 0.425 g) in anhydrous 1,2-dimethoxyethane (2 ml) was then added drop-wise. After the addition was complete the reaction mixture was stirred at room temperature for 1 hour prior to heating to 80° C. for 18 hours. After cooling to room temperature, water was added and the product extracted into ether. The combined organic extracts were dried (MgSO$_4$) filtered and evaporated, to yield the title compound as a yellow oil.

HPLC Rt=4.5 minutes

Intermediate 105

2-(4-hydroxy-3-methylphenyl)-2-methyl-1-{3-methyl-5-[4-(trifluoromethyl)phenyl]thien-2-yl}propan-1-one To 2-(4-methoxy-3-methylphenyl)-2-methyl-1-{3-methyl-5-[4-(trifluoromethyl)phenyl]thien-2-yl}propan-1-one (intermediate 104, 0.35 g) in a pressure vessel was added pyridine hydrochloride (10 g), the vessel was sealed and heated to 150° C. for 72 hours. The reaction vessel was then allowed to cool to room temperature and the solid residue partioned between water and CH$_2$Cl$_2$, the aqueous extract was further extracted CH$_2$Cl$_2$. The combined organic extracts were dried (Na$_2$SO$_4$), filtered and evaporated to yield a brown oil. Purification by flash column chromatography eluting with 1% EtOAc/cyclohexane yielded the title compound as a pale yellow oil.

HPLC Rt=4.3 minutes

Intermediate 106 ethyl[4-(1,1-dimethyl-2-{3-methyl-5-[4-(trifluoromethyl)phenyl]thien-2-yl}-2-oxoethyl)-2-methylphenoxy]acetate To a solution of 2-(4-hydroxy-3-methylphenyl)-2-methyl-1-{3-methyl-5-[4-(trifluoromethyl)phenyl]thien-2-yl}propan-1-one (intermediate 105, 62.0 mg) in anhydrous acetonitrile (2 ml) was added caesium carbonate (106 mg) and ethyl bromoacetate (18 μl) and the reaction stirred at room temperature under nitrogen for 20 hours. The solid residue was filtered, and the filtrate was concentrated in vacuo and the residue purified by flash column chromatography, eluting with 1% EtOAc/cyclohexane yielded the title compound as a white solid.

$^1$H NMR (CDCl$_3$) 7.57 (d, 2 H), 7.51 (d, 2 H), 7.15–7.10 (m, 3 H), 6.70 (dd, 1H), 4.65 (s, 2H), 4.24 (q, 2 H), 2.55 (s, 3 H), 2.29 (s, 3 H), 1.58 (s, 6 H), 1.26 (t, 3 H).

Intermediate 107 ethyl(2-ethylphenoxy)acetate

A mixture of 2-ethylphenol (244 mg) in acetonitrile (20 ml) was treated with cesium carbonate (650 mg) and ethyl bromoacetate (0.221 ml) and the mixture stirred at 60° C. for 6 hours and then at ambient temperature for 17 hours. The reaction mixture was diluted with ethyl acetate; the suspension filtered and the title compound isolated by evaporation in vacuo of the filtrate as a colourless oil.

$^1$H NMR (CDCl$_3$) 7.18–7.11 (m, 2 H), 6.93 (t, 1 H), 6.71 (d, 1 H), 4.63 (s, 2H), 4.26 (q, 2 H), 2.72 (q, 2 H), 1.29 (t, 3 H), 1.23 (t, 3 H).

Intermediate 108 ethyl(2-isopropylphenoxy)acetate

Prepared using a method analogous to the preparation of ethyl(2-ethylphenoxy)acetate (intermediate 107).

$^1$H NMR (CDCl$_3$) 7.24–7.23 (m, 1 H), 7.14–7.10 (m, 1H), 6.96 (t, 1 H), 6.71 (d, 1 H), 4.63 (s, 2H), 4.27 (q, 2 H), 3.46–3.39 (m, 1 H), 1.25 (t, 3 H), 1.23 (d, 6 H).

Intermediate 109 ethyl(2-chlorophenoxy)acetate

Prepared using a method analogous to the preparation of ethyl(2-ethylphenoxy)acetate (intermediate 107)

$^1$H NMR (CDCl$_3$) 7.39 (d, 1 H), 7.20 (t, 1H), 6.95 (t, 1 H), 6.85 (d, 1 H), 4.70 (s, 2H), 4.27 (q, 2 H), 1.29 (t, 3 H)

Intermediate 110 ethyl(2-bromophenoxy)acetate

Prepared using a method analogous to the preparation of ethyl(2-ethylphenoxy)acetate (intermediate 107).

$^1$H NMR (CDCl$_3$) 7.56 (d, 1 H), 7.24 (t, 1H), 6.88 (t, 1 H), 6.82 (d, 1 H), 4.70 (s, 2H), 4.27 (q, 2 H), 1.29 (t, 3 H)

Intermediate 111 ethyl[4-(chlorosulfonyl)-2-ethylphenoxy]acetate

A solution of crude ethyl(2-ethylphenoxy)acetate (intermediate 107) in chloroform (6 ml) was stirred with chlorosulfonic acid (1.33 ml) at ambient temperature for 4 hours. The reaction mixture was quenched by the addition of ice and the organic mixture separated by using a hydrophobic frit. The title compound was isolated by evaporation of this filtrate.

$^1$H NMR (CDCl$_3$) 7.87–7.85 (m, 2 H), 6.81 (d, 1 H), 4.76 (s, 2H), 4.29 (q, 2 H), 2.72 (q, 2 H), 1.31 (t, 3 H), 1.28 (t, 3 H).

Intermediates 112–114 were repared using an analogous method to the preparation of ethyl[4-(chlorosulfonyl)-2-ethylphenoxy]acetate (intermediate 111).

Intermediate 112 ethyl[4-(chlorosulfonyl)-2-isopropylphenoxy]acetate

Prepared using intermediate 108.

$^1$H NMR (CDCl$_3$) 7.88–7.84 (m, 2 H), 6.82 (d, 1 H), 4.77 (s, 2H), 4.29 (q, 2 H), 3.47–3.40 (m, 1 H), 1.31 (t, 3 H), 1.29 (d, 6 H).

Intermediate 113 ethyl[4-(chlorosulfonyl)-2-chlorophenoxy]acetate

Prepared using intermediate 109.

$^1$H NMR (CDCl$_3$) 8.09 (d, 1 H), 7.91 (dd, 1 H), 6.94 (d, 1H), 4.84 (s, 2H), 4.30 (q, 2 H), 1.32 (t, 3 H).

Intermediate 114 ethyl[4-(chlorosulfonyl)-2-bromophenoxy]acetate

Prepared using intermediate 110.

$^1$H NMR (CDCl$_3$) 8.25 (d, 1 H), 7.95 (dd, 1 H), 6.90 (d, 1H), 4.83 (s, 2H), 4.30 (q, 2 H), 1.32 (t, 3 H).

Intermediate 115 triisopropyl[(3-methylthien-2-yl)methoxy]silane

A solution of (3-methylthien-2-yl)methanol (3.20 g) in tetrahydrofuran (10 ml) was added to a mixture of sodium hydride (60% dispersion in mineral oil, 1.05 g) in tetrahydrofuran (40 ml). After the evolution of hydrogen had subsided triisopropylsilyl chloride (5.2 ml) was added. The reaction mixture was stirred for 2 hours then diluted with ethyl acetate. The mixture was extracted with water, 2M aqueous sodium hydroxide, water and dried with brine and over sodium sulfate. The crude product was purified by Biotage chromatography® using 100:1 petroleum ether: ethyl acetate as eluent to give the title compound as a colorless oil.

HPLC Rt=4.5 minutes

Intermediate 116 triisopropyl{[3-methyl-5-(4,4,5,5-tetramethyl-1,3,2-dioxaborolan-2-yl)thien-2-yl]methoxy}silane

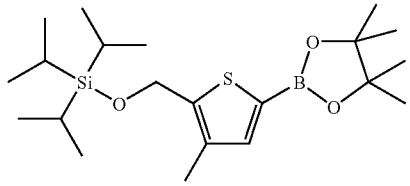

A mixture of triisopropyl[(3-methylthien-2-yl)methoxy]silane (intermediate 115, 1.42 g) in tetrahydrofuran (20 ml), stirred at −78° C. under nitrogen, was treated with 1.6M butyllithium in hexanes (3.9 ml). The reaction temperature was slowly allowed to rise to 0° C. over 2 hours and then re-cooled to −78° C. 2-Isopropoxy-4,4,5,5-tetramethyl-1,3,2-dioxaborolane (1.28 ml) was added and the reaction stirred at this temperature for 4 hours and then warmed to 0° C. The reaction was added to a mixture of saturated ammonium chloride and ice. The aqueous mixture was extracted with diethyl ether and the organic solution dried with brine and over sodium sulfate. Evaporation of the solvent afforded the title compound as a white solid HPLC Rt=4.7 minutes Intermediate 117 triisopropyl({3-methyl-5-[4-(trifluoromethoxy)phenyl]thien-2-yl}methoxy)silane

A mixture of triisopropyl{[3-methyl-5-(4,4,5,5-tetramethyl-1,3,2-dioxaborolan-2-yl)thien-2-yl]methoxy}silane (intermediate 116, 0.40 g) in 1,2-dimethoxyethane (12 ml) and water (6 ml) was treated with 4-bromo-trifluoromethoxybenzene (0.26 g), sodium carbonate (0.26 g) and tetrakis(triphenylphosphine)palladium (0) (0.120 g). The reaction mixture was stirred at reflux for 2 hours and then partitioned between water and ethyl acetate. The aqueous layer was separated and extracted with further ethyl acetate and then the organic solutions combined and dried over magnesium sulfate. The crude product was purified by Si SPE using dichloromethane as eluent to give the title compound as a yellow gum.

HPLC Rt=5.0 minutes

Intermediate 118

{3-methyl-5-[4-(trifluoromethoxy)phenyl]thien-2-yl}methanol

A mixture of triisopropyl({3-methyl-5-[4-(trifluoromethoxy)phenyl]thien-2-yl}methoxy)silane (intermediate 117, 0.97 g) in tetrahydrofuran (30 ml) was treated with tetraethylammonium fluoride (0.392 g) and the reaction mixture stirred at ambient temperature for 1 hour. The solvent was evaporated and the residue purified by flash column chromatography using cyclohexane:ethyl acetate (2:1) as eluent to give the title compound.

HPLC Rt=3.7 minutes

Intermediate 119

({5-[2,5-difluoro-4-(trifluoromethyl)phenyl]-3-methylthien-2-yl}methoxy)(triisopropyl)silane The title compound was prepared using a method analogous to that used for the preparation of triisopropyl({3-methyl-5[4-(trifluoromethoxy)phenyl]thien-2-yl}methoxy)silane (intermediate 117) using 2,5-difluoro-4-(trifluoromethylbromo)benzene.

HPLC Rt=5.0 minutes

Intermediate 120

{5-[2,5-difluoro-4-(trifluoromethyl)phenyl]-3-methylthien-2-yl}methanol

The title compound was prepared using a method analogous to that used for the preparation of {3-methyl-5-[4-(trifluoromethoxy)phenyl]thien-2-yl}methanol (intermediate 118) using ({5-[2,5-difluoro-4-(trifluoromethyl)phenyl]-3-methylthien-2-yl}methoxy)(triisopropyl)silane (intermediate 119).

HPLC Rt=3.7 minutes

Intermediate 121

({5-[2,3-difluoro-4-(trifluoromethyl)phenyl]-3-methylthien-2-yl}methoxy)(triisopropyl)silane The title compound was prepared using a method analogous to that used for the preparation of triisopropyl({3-methyl-5-[4-(trifluoromethoxy)phenyl]thien-2-yl}methoxy)silane (intermediate 117) using 2,3-difluoro-4-(trifluoromethylbromo)benzene.

HPLC Rt=5.0 minutes

Intermediate 122

{5-[2,3-difluoro-4-(trifluoromethyl)phenyl]-3-methylthien-2-yl}methanol

The title compound was prepared using a method analogous to that used for the preparation of {3-methyl-5-[4-(trifluoromethoxy)phenyl]thien-2-yl}methanol (intermediate 118) using ({5-[2,5-difluoro-4-(trifluoromethyl)phenyl]-3-methylthien-2-yl}methoxy)(triisopropyl)silane (intermediate 121).

HPLC Rt=3.7 minutes

Intermediate 123

({5-[2-fluoro-4-trifluoromethyl)phenyl]-3-methylthien-2-yl}methoxy)(triisopropyl)silane The title compound was prepared using a method analogous to that used for the preparation of triisopropyl({3-methyl-5-[4-(trifluoromethoxy)phenyl]thien-2-yl}methoxy)silane (intermediate 117) using 3-fluoro-4-(trifluoromethylbromo)benzene.

HPLC Rt=5.0 minutes

Intermediate 124

{5-[2-fluoro-4-(trifluoromethyl)phenyl]-3-methylthien-2-yl}methanol

The title compound was prepared using a method analogous to that used for the preparation of {{3-methyl-5-[4-(trifluoromethoxy)phenyl]thien-2-yl}methanol (intermediate 118) using ({5-[2-fluoro-4-(trifluoromethyl)phenyl]-3-methylthien-2-yl}methoxy)(triisopropyl)silane (intermediate 123).

HPLC Rt=3.7 minutes

Intermediate 125

4-[4-(trifluoromethyl)phenyl]thiophene-3-carbaldehyde

The title compound was prepared using a method analogous to that used for the preparation of 4-[4-(trifluoromethyl)phenyl]thiophene-2-carbaldehyde using 2-bromothiophene-4-carboxaldehyde (Foumari, P. et al., Bull. Soc. Chim. Fr., 1967, 4115–4120) and 4-trifluoromethylbenzene boronic acid.

HPLC Rt=4.1 minutes

Intermediate 126

1-{5-[4-(trifluoromethyl)phenyl]thien-3-yl}ethanol

A solution of methyl magnesium bromide (13.9 ml, 1.4M solution in THF/toluene) diluted with THF (30 ml) at 0° C. was treated with a solution of 4-[4-(trifluoromethyl)phenyl]thiophene-3-carbaldehyde (intermediate 125, 1.0 g) in THF (30 ml). The reaction mixture was allowed to ambient temperature, stirred for 3 hours and aqueous ammonium chloride added. The reaction mixture was partitioned with ethyl acetate and the organic layer separated; the aqueous layer was further extracted with ethyl acetate; the organic layers combines and extracted with water and dried with brine and over sodium sulfate. The crude product was purified by SPE (Si cartridge) using cyclohexane:ethyl acetate mixtures as eluents to give the title compound as a cream solid.

HPLC Rt=3.5 minutes

Intermediate 127 phenyl{5-[4-(trifluoromethyl)phenyl]thien-3-yl}methanol

The title compound was prepared using a method analogous to that used for the preparation of 1-{5-[4-(trifluoromethyl)phenyl]thien-3-yl}ethanol (intermediate 126) using 4-[4-(trifluoromethyl)phenyl]thiophene-3-carbaldehyde (intermediate 125) and phenyl magnesium bromide.

HPLC Rt=3.8 minutes

Intermediate 128

5-[4-(trifluoromethyl)phenyl]thiophene-2-carbaldehyde

The title compound was prepared using a method analogous to that used for the preparation of 4-[4-(trifluoromethyl)phenyl]thiophene-2-carbaldehyde (intermediate 37) using 2-bromothiophene-5-carboxaldehyde and 4-trifluoromethylbenzene boronic acid.

HPLC Rt=3.6 minutes

Intermediate 129

1-{5-[4-trifluoromethyl)phenyl]thien-2-yl}ethanol

The title compound was prepared using a method analogous to that used for the preparation of 1-{5-[4-(trifluoromethyl)phenyl]thien-3-yl}ethanol (intermediate 126) using 5-[4-(trifluoromethyl)phenyl]thiophene-2-carbaldehyde (intermediate 128) and methyl magnesium bromide.

HPLC Rt=3.6 minutes

Intermediate 130

1-{3-methyl-5-[4-(trifluoromethyl)phenyl]thien-2-yl}ethanol

The title compound was prepared using a method analogous to that used for the preparation of 1-{5-[4-(trifluoromethyl)phenyl]thien-3-yl}ethanol (intermediate 126) using 3-methyl-5-[4-(trifluoromethyl)phenyl]thiophene-2-carbaldehyde (intermediate 74) and methyl magnesium bromide.

HPLC Rt=3.8 minutes

Intermediate 130

3-methyl-5-[4-(trifluoromethyl)phenyl]thiophene-2-carboxylic acid

The title compound was prepared using 3-methyl-5-[4-(trifluoromethyl)phenyl]thiophene-2-carbaldehyde (intermediate 74) by a method analogous to the preparation of 4-[4-(trifluoromethyl)phenyl]thiophene-2-carboxylic acid (intermediate 38).

HPLC Rt=4.0 minutes

Intermediate 131 methyl 3-methyl-5-[4-(trifluoromethyl)phenyl]thiophene-2-carboxylate

A mixture of 3-methyl-5[4-(trifluoromethyl)phenyl]thiophene-2-carboxylic acid (intermediate 130, 8.1 g) in methanol (300 ml) was heated at 30° C. and hydrogen chloride gas bubbled through the mixture. The reaction mixture was then stirred at reflux for 21 hours; cooled and treated with further hydrogen chloride gas. The reaction mixture was stirred at reflux for a further 6 hours, cooled and concentrated. The resulting precipitate was filtered and washed with cyclohexane to give the title compound as a solid.

$^1$H NMR (CD$_3$OD) 7.85 (d, 2 H), 7.70 (d, 2 H), 7.41 (s, 1H), 3.86 (s, 3H), 2.55 (s, 3 H).

Intermediate 132 methyl 3-(bromomethyl)-5-[4-trifluoromethyl)phenyl]thiophene-2-carboxylate

The title compound was prepared using a method analogous to that used for the preparation of ethyl 3-(bromomethyl)-5-[4-(trifluoromethyl)phenyl]thiophene-2-carboxylate (intermediate 43) using methyl 3-methyl-5-[4-(trifluoromethyl)phenyl]thiophene-2-carboxylate (intermediate 131).

$^1$H NMR (CDCl$_3$) 7.73 (d, 2 H), 7.68 (d, 2 H), 7.45 (s, 1H), 4.92 (s, 2H), 3.94 (s, 3 H).

Intermediates 133–138 were prepared using intermediate 133 by methods analogous to those described above for the preparation of intermediate 46

Intermediate 133

{5-[4-(trifluoromethyl)phenyl]-3-[(isopropylthio)methyl]thien-2-yl}methanol

The title compound was prepared using methyl 3-(bromomethyl)-5-[4-(trifluoromethyl)phenyl]thiophene-2-carboxylate (intermediate 132) and isopropylthiol.

$^1$H NMR (CDCl$_3$) 7.66 (d, 2 H), 7.61 (d, 2 H), 7.26 (s, 1 H), 4.80 (s, 2H), 3.79 (s, 2 H), 2.92 (m, 1 H), 1.30 (d,6 H).=

Intermediate 134

{5-[4-(trifluoromethyl)phenyl]-3-[(2,3,6-trimethylphenoxy)methyl]thien-2-yl}methanol The title compound was prepared using methyl 3-(bromomethyl)-5-[4-(trifluoromethyl)phenyl]thiophene-2-carboxylate (intermediate 132) and 2,5,6-trimethylphenol.

$^1$H NMR (CDCl$_3$) 7.70 (d, 2 H), 7.64 (d, 2 H), 7.38 (s, 1 H), 6.96 (d, 1 H), 6.89 (d, 1 H), 4.83 (s, 2H), 4.79 (s, 2 H), 2.27 (s, 3 H), 2.25 (s, 3 H), 2.21 (s, 3 H).

Intermediate 135

{3-{[(2-isopropyl-6-methylpyrimidin-4-yl)oxy]methyl}-5-[4-(trifluoromethyl)phenyl]thien-2-yl}methanol The title compound was prepared using methyl 3-(bromomethyl)-5-[4-(trifluoromethyl)phenyl]thiophene-2-carboxylate (intermediate 132) and 2-isopropyl-6-methyl-4-pyrimidinol.

$^1$H NMR (CDCl$_3$) 7.66 (d, 2 H), 7.62 (d, 2 H), 7.40 (s, 1 H), 6.45 (s, 1 H), 5.49 (s, 2H), 4.53 (s, 2 H), 3.09 (m, 1 H), 2.47 (s, 3 H), 1.32 (d, 6 H).

Intermediate 136

{2-[(quinolin-2-ylthio)methyl]-5-[4-(trifluoromethyl)phenyl]-3-furyl}methanol

The title compound was prepared using methyl 2-(bromomethyl)-5-[4-(trifluoromethyl)phenyl]-3-furoate (intermediate 44) and 2-quinolinethiol.

HPLC Rt=4.0 minutes

Intermediate 137

{2-{[(3-phenyl-1H-1,2,4-triazol-5-yl)thio]methyl}-5-[4-(trifluoromethyl)phenyl]-3-furyl}methanol

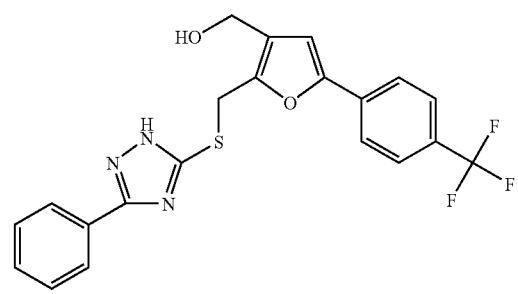

The title compound was prepared using methyl 2-(bromomethyl)-5-[4-(trifluoromethyl)phenyl]-3-furoate (intermediate 44) and 3-phenyl-1,2,4-triazole-5-thiol.

HPLC Rt=3.6 minutes

Intermediate 138

{2-{[4-(4-methoxyphenyl)piperazin-1-yl]methyl}-5-[4-(trifluoromethyl)phenyl]-3-furyl}methanol The title compound was prepared using methyl 2-(bromomethyl)-5-[4-(trifluoromethyl)phenyl]-3-furoate (intermediate 44) and 1-(4-methoxyphenyl)piperazine.

HPLC Rt=3.1 minutes

EXAMPLES

Example 1 ethyl{2-methyl-4-[({5-[4-(trifluoromethyl)phenyl]-3-furyl}methyl)thio]phenoxy}acetate A solution of {5-[4-(trifluoromethyl)phenyl]-3-furyl}methanol (0.15 g) in tetrahydrofuran (15 ml) stirred at 0° C. was treated with tributylphosphine (0.2 ml), as solution of ethyl(4-mercapto-2-methylphenoxy)acetate (0.150 g) in tetrahydrofuran (2 ml) and finally azodicarbonyldimorpholide (0.204 g). The reaction was allowed to warm to ambient temperature and stirred for 18 hours. The solvent was evaporated and the residue subjected to an aqueous work up using ethyl acetate and water. The organic phase was dried over magnesium sulfate. The product isolated after evaporation of the solvent was further purified by flash column chromatography using a cyclohexane:ethyl acetate (5:1) as eluent to give the title compound.

Example 2

2-methyl-4-[({5-[4-(trifluoromethyl)phenyl]-3-furyl}methyl)thio]phenoxy}acetic acid A mixture of ethyl{2-methyl-4-[({5-[4-(trifluoromethyl)phenyl]-3-furyl}methyl)thio]phenoxy}acetate (example 1, 0.050 g) in tetrahydrofuran (4 ml) and 2M aqueous sodium hydroxide (4 ml) was stirred at 60° C. for 2 hours. The solvent was evaporated and the residue partitioned between ether and water; the aqueous layer was acidified using 10% w/v aqueous citric acid and the then extracted thrice with ethyl acetate. The combined ethyl acetate solutions were dried over magnesium sulfate and evaporated to give the title compound.

m/z (M−H)⁻=420

HPLC Rt=4.6 minutes

The following compounds were prepared by analogous methodology to that described for the preparation of examples 1 and 2.

Example 3 ethyl{2-methyl-4-[({2-methyl-5-[4-(trifluoromethyl)phenyl]-3-furyl}methyl)thio]phenoxy}acetate Prepared from intermediates 4 and 24

Example 4

{2-methyl-4-[({2-methyl-5-[4-(trifluoromethyl)phenyl]-3-furyl}methyl)thio]phenoxy}acetic acid Prepared by hydrolysis of example 3
m/z (M−H)⁻=434
HPLC Rt=5.1 minutes Example 5 ethyl{2-methyl-4-[({3-methyl-5-[4-(trifluoromethyl)phenyl]-2-furyl}methyl)thio]phenoxy}acetate Prepared from intermediates 4 and 25

Example 6

{2-methyl-4-[({3-methyl-5-[4-(trifluoromethyl)phenyl]-2-furyl}methyl)thio]phenoxy}acetic acid Prepared by hydrolysis of example 5
m/z (M−H)⁻=436
HPLC Rt=4.8 minutes Example 7 ethyl{2-methyl-4-[({5-[4-(trifluoromethyl)phenyl]-2-furyl}methyl)thio]phenoxy}acetate Prepared from intermediates 4 and 26

Example 8

{2-methyl-4-[({5-[4-(trifluoromethyl)phenyl]-2-furyl}methyl)thio]phenoxy}acetic acid Example 9 ethyl{2-methyl-4-[({5-[4-(trifluoromethyl)phenyl]thien-3-yl}methyl)thio]phenoxy}acetate Prepared from intermediates 4 and 29

Example 10

2-methyl-4-[({5-[4-(trifluoromethyl)phenyl]-3-thienyl}methyl)thio]phenoxy}acetic acid Prepared by hydrolysis of example 9
HPLC Rt=4.3 minutes
m/z (M−H)⁻=448

Example 11 ethyl{2-methyl-4-[({5-[4-(trifluoromethyl)phenyl]thien-2-yl}methyl)thio]phenoxy}acetate Prepared from intermediates 4 and 28

Example 12

2-methyl-4-[({5-[4-(trifluoromethyl)phenyl]-2-thienyl}methyl)thio]phenoxy}acetic acid Prepared by hydrolysis of example 11
HPLC Rt=5.2 minutes
m/z (M−H)⁻=437

Example 13 ethyl{2-methyl-4-[({3-methyl-5-[4-(trifluoromethyl) phenyl]thien-2-yl}methyl)thio]phenoxy}acetate Prepared from intermediates 4 and 24

Example 14

{2-methyl-4-[({2-methyl-5-[4-(trifluoromethyl)phenyl]-3-furyl}methyl)thio]phenoxy}acetic acid Prepared by hydrolysis of example 13
HPLC Rt=5.1 minutes
m/z $(M-H)^-$=435

Example 15

Ethyl{2-methyl-4-[({3-methyl-4-[4-(trifluoromethyl) phenyl]thien-2-yl}methyl)thio]phenoxy}acetate Prepared from intermediates 4 and 36

Example 16

{2-methyl-4-[({3-methyl-4-[4-(trifluoromethyl)phenyl]thien-2-yl}methyl)thio]phenoxy}acetic acid Prepared by hydrolysis of example 15
HPLC Rt=4.0 minutes
m/z $(M-H)^-$=451

Example 17 ethyl[4-({[5-[4-(trifluoromethyl)phenyl]-2-methyl-3-furyl]methyl}thio)-2-methylphenoxy]acetate Prepared from intermediates 4 and 42

Example 18

{2-methyl-4-[({2-methyl-5-[4-(trifluoromethyl)phenyl]thien-3-yl}methyl)thio]phenoxy}acetic acid Prepared by hydrolysis of example 17
HPLC Rt=4.6 minutes
m/z $(M-H)^-$=451

Example 19 ethyl[4-({[5-(4-chlorophenyl)-2-(trifluoromethyl)-3-furyl]methyl}thio)-2-methylphenoxy]acetate Prepared from intermediates 4 and 30

Example 20

[4-({[5-(4-chlorophenyl)-2-(trifluoromethyl)-3-furyl] methyl}thio)-2-methylphenoxy]acetic acid Prepared by hydrolysis of example 19
m/e $(M-H)^-$=455/457
HPLC Rt=4.5 minutes

Example 21 ethyl{2-methyl-4-[({2-(trifluoromethyl)-5-[4-(trifluoromethyl)phenyl]-3-furyl}methyl)thio] phenoxy}acetate Prepared from intermediates 4 and 31

Example 22

2-methyl-4-[({2-(trifluoromethyl)-5-[4-(trifluoromethyl)phenyl]-3-furyl}methyl)thio]phenoxy}acetic acid Prepared by hydrolysis of example 21
m/z $(M-H)^-$=489
HPLC Rt=4.9 minutes

Example 23 ethyl{2-methyl-4-[({2-methyl)-5-[4-chlorophenyl]-3-furyl}methyl)thio]phenoxy}acetate Prepared from intermediates 4 and 32

Example 24

[4-({[5-(4-chlorophenyl)-2-methyl-3-furyl] methyl}thio)-2-methylphenoxy]acetic acid Prepared by hydrolysis of example 23
m/z $(M-H)^-$=402
HPLC Rt=5.2 minutes

Example 25 ethyl[2-methyl-4-({3-methyl-5-[5-trifluoromethyl) pyridin-2-yl]thien-2-yl}methoxy)phenoxy]acetate Prepared from intermediates 7 and 79

Example 26

[2-methyl-4-({3-methyl-5-[5-(trifluoromethyl)pyridin-2-yl]thien-2-yl}methoxy)phenoxy]acetic acid Prepared by hydrolysis of example 25
m/z $(M-H)^-$=436
HPLC Rt=4.2 minutes

Example 27 ethyl(4-{[5-(4-chlorophenyl)-2-methyl-3-furyl]methoxy}-2-methylphenoxy)acetate

Prepared from intermediates 7 and 32

Example 28

(4-{[5-(4-chlorophenyl)-2-methyl-3-furyl]methoxy}-2-methylphenoxy)acetic acid

Prepared by hydrolysis of example 27
m/z $(M-H)^-$=385
HPLC Rt=4.5 minutes

Example 29 ethyl[2-methyl-4-({2-trifluoromethyl)-5-[4-(trifluoromethyl)phenyl]-3-furyl}methoxy)phenoxy]acetate Prepared from intermediates 7 and 31

Example 30

[2-methyl-4-({2-(trifluoromethyl)-5-[4-(trifluoromethyl)phenyl]-3-furyl}methoxy)phenoxy]acetic acid Prepared by hydrolysis of example 29
m/z (M–H)$^-$=473
HPLC Rt=4.0 minutes

Example 31 ethyl[2-methyl-4-({2-methyl-5-[4-(trifluoromethyl)phenyl]-3-furyl}methoxy)phenoxy]acetate Prepared from intermediates 7 and 24

Example 32

[2-methyl-4-({2-methyl-5-[4-(trifluoromethyl)phenyl]-3-furyl}methoxy)phenoxy]acetic acid Prepared by hydrolysis of example 31
m/z (M–H)$^-$=419
HPLC Rt=4.0 minutes

Example 33 ethyl[2-methyl-4-({3-methyl-5-[4-(trifluoromethyl)phenyl]thien-2-yl}methoxy)phenoxy]acetate Prepared from intermediates 7 and 36

Example 34

[2-methyl-4-({3-methyl-5-[4-(trifluoromethyl)phenyl]thien-2-yl}methoxy)phenoxy]acetic acid Prepared by hydrolysis of example 33
m/z (M–H)$^-$=435
HPLC Rt=4.2 minutes

Example 35 ethyl[2-methyl-4-({3-methyl-5-[4-(trifluoromethyl)phenyl]-2-furyl}methoxy)phenoxy]acetate Prepared from intermediates 7 and 25

Example 36

[2-methyl-4-({3-methyl-5-[4-(trifluoromethyl)phenyl]-2-furyl}methoxy)phenoxy]acetic acid Prepared by hydrolysis of example 35
m/z (M–H)$^-$=419
HPLC Rt=3.9 minutes

Example 37 ethyl3-(4-{[5-(4-chlorophenyl)-2-trifluoromethyl)-3-furyl]methoxy}phenyl)propanoate Prepared from intermediates 7 and 30

Example 38

(4-{[5-(4-chlorophenyl)-2-(trifluoromethyl)-3-furyl]methoxy}-2-methylphenoxy)acetic acid Prepared by hydrolysis of example 37
m/z (M–H)$^-$=439
HPLC Rt=4.4 minutes

Example 39 ethyl[2-methyl-4-({2-methyl-5-[4-(trifluoromethyl)phenyl]thien-3-yl}methoxy)phenoxy]acetate Prepared from intermediates 7 and 42

Example 40

{2-methyl-4-[({2-methyl-5-[4-(trifluoromethyl)phenyl]thien-3-yl}methoxy)-2-methylphenoxy}acetic acid Prepared by hydrolysis of example 39
m/z (M–H)$^-$=436
HPLC Rt=4.3 minutes

Example 41 ethyl 2-(4-{[5-(4-chlorophenyl)-2-methyl-3-furyl]methoxy}-2-methylphenoxy)-2-methylpropanoate Prepared from intermediates 10 and 32

Example 42

2-(4-{[5-(4-chlorophenyl)-2-methyl-3-furyl]methoxy}-2-methylphenoxy)-2-methylpropanoic acid Prepared by hydrolysis of example 41
m/z (M–H)$^-$=413
HPLC Rt=4.3 minutes

Example 43 ethyl2-methyl-2-[2-methyl-4-({2-methyl-5-[4-(trifluoromethyl)phenyl]-3-furyl}methoxy)phenoxy]propanoate Prepared from intermediates 10 and 24

Example 44

2-methyl-2-[2-methyl-4-({2-methyl-5-[4-(trifluoromethyl)phenyl]-3-furyl}methoxy)phenoxy]propanoic acid Prepared by hydrolysis of example 43
m/z (M–H)$^-$=447
HPLC Rt=4.3 minutes

Example 45 ethyl 2-methyl-2-[2-methyl-4-({2-trifluoromethyl)-5-[4-(trifluoromethyl)phenyl]-3-furyl}methoxy)phenoxy]propanoate Prepared from intermediates 10 and 31

Example 46

2-methyl-2-[2-methyl-4-({2-trifluoromethyl)-5-[4-(trifluoromethyl)phenyl]-3-furyl}methoxy)phenoxy]propanoic acid Prepared by hydrolysis of example 45
m/z (M−H)⁻=501
HPLC Rt=4.4 minutes

Example 47 ethyl 2-methyl-2-[2-methyl-4-({3-methyl-5-[4-(trifluoromethyl)phenyl]thien-2-yl}methoxy)phenoxy]propanoate Prepared from intermediates 10 and 36

Example 48

2-methyl-2-[2-methyl-4-({3-methyl-5-[4-(trifluoromethyl)phenyl]thien-2-yl}methoxy)phenoxy]propanoic acid Prepared by hydrolysis of example 47
m/z (M−H)⁻=463
HPLC Rt=4.4 minutes

Example 49 ethyl 2-(4-{[5-(4-chlorophenyl)-2-(trifluoromethyl)-3-furyl]methoxy}-2-methylphenoxy)-2-methylpropanoate Prepared from intermediates 10 and 30

Example 50

2-(4-{[5-(4-chlorophenyl)-2-(trifluoromethyl)-3-furyl]methoxy}-2-methylphenoxy)-2-methylpropanoic acid Prepared by hydrolysis of example 49
m/z (M−H)⁻=467
HPLC Rt=4.4 minutes

Example 51 ethyl 2-methyl-2-[2-methyl-4-({2-methyl-5-[4-(trifluoromethyl)phenyl]thien-3-yl}methoxy)phenoxy]propanoate Prepared from intermediates 10 and 42

Example 52

2-methyl-2-[2-methyl-4-({2-methyl-5-[4-(trifluoromethyl)phenyl]thien-3-yl}methoxy)phenoxy]propanoic acid Prepared by hydrolysis of example 51
m/z (M−H)⁻=463
HPLC Rt=4.4 minutes

Example 53 ethyl 3-[4-({3-methyl-5-[4-(trifluoromethyl)phenyl]thien-2-yl}methoxy)phenyl]propanoate Prepared from commercially available ethyl 3-(4-hydroxyphenyl)propanoate and intermediate 36.

Example 54

3-[4-({3-methyl-5-[4-(trifluoromethyl)phenyl]thien-2-yl}methoxy)phenyl]propanoic acid Prepared by hydrolysis of example 53
m/z (M−H)⁻=419
HPLC Rt=4.1 minutes

Example 55 ethyl 3-(4-{[5-(4-chlorophenyl)-2-(trifluoromethyl)-3-furyl]methoxy}phenyl)propanoate Prepared from commercially available ethyl 3-(4-hydroxyphenyl)propanoate and intermediate 30

Example 56

3-(4-{[5-(4-chlorophenyl)-2-(trifluoromethyl)-3-furyl]methoxy}phenyl)propanoic acid Prepared by hydrolysis of example 55
m/z (M−H)⁻=423
HPLC Rt=4.2 minutes

Example 57 ethyl 3-(4-{[5-4-chlorophenyl)-2-(trifluoromethyl)-3-furyl]methoxy}-2-methylphenyl)propanoate Prepared from intermediates 12 and 30

Example 58

3-(4-{[5-(4-chlorophenyl)-2-(trifluoromethyl)-3-furyl]methoxy}-2-methylphenyl)propanoic acid Prepared by hydrolysis example 57
m/z (M−H)⁻=437
HPLC Rt=4.3 minutes

Example 59 ethyl 3-[2-methyl-4-({3-methyl-5-[4-(trifluoromethyl)phenyl]thien-2-yl}methoxy)phenyl]propanoate Prepared from intermediates 12 and 36

Example 60

3-[2-methyl-4-({3-methyl-5-[4-(trifluoromethyl)phenyl]thien-2-yl}methoxy)phenyl]propanoic acid Prepared by hydrolysis of example 59
m/z (M−H)⁻=433
HPLC Rt=4.3 minutes

Example 61 ethyl(4-{2-[5-(4-chlorophenyl)-2-trifluoromethyl)-3-furyl]ethoxy}-2-methylphenoxy)acetate Prepared from intermediates 7 and 87

Example 62

(4-{2-[5-(4-chlorophenyl)-2-(trifluoromethyl)-3-furyl]ethoxy-2-methylphenoxy)acetic acid Prepared by hydrolysis of example 61
m/z (M−H)⁻=453
HPLC Rt=4.3 minutes

Example 63 ethyl{2-methyl-4-[({2-(2-pyridin-4-ylethyl)-5-[4-(trifluoromethyl)phenyl]-3-furyl}methyl)thio]phenoxy}acetate {2-(2-Pyridin-4-ylethyl)-5-[4-(trifluoromethyl)phenyl]-3-furyl}methanol (intermediate 65, 0.59 g) was dissolved in dry dichloromethane (4 ml), cooled in ice/water bath and treated with thionyl chloride (0.124 ml). The reaction was allowed to warm up to room temperature, stirred for 2 hours and then concentrated under reduced pressure. The residue was then dissolved in acetonitrile (4 ml) followed by sequential addition of potassium carbonate (0.47 g) and ethyl(4-mercapto-2-methylphenoxy)acetate (intermediate 4, 0.46 g) and allowed to stir overnight at room temperature. The reaction was concentrated to dryness, partitioned between chloroform/water. The organic layer was dried through a hydrophobic frit, concentrated under reduced pressure and purified using SPE (Si cartridge) using dichloromethane:methanol: "880" ammonia (196:3:1) as eluent to give the title compound as a pale brown gum.

$^1$H NMR (CDCl3) δ 8.50 (d, 2H), 7.62 (2×d, 4H), 7.18 (d, 1H), 7.13 (m, 2H), 7.09 (d, 1H), 6.62 (s, 1H), 6.59 (d, 1H), 4.61 (s, 2H), 4.24 (q, 2H), 3.64 (s, 2H), 2.85 (t, 2H), 2.74 (t, 2H), 2.22 (s, 3H), 1.28 (t, 3H)

Example 64

{2-methyl-4-[({2-(2-pyridin-4-ylethyl)-5-[4-(trifluoromethyl)phenyl]-3-furyl}methyl)thio]phenoxy}acetic acid hydrochloride
Prepared by hydrolysis of example 63
m/z (M−H)⁻=525
HPLC Rt=3.8 minutes
The following compounds were prepared in an analogous manner to that described for the preparation of example 61.

Example 65 ethyl{4-[({2-[(isopropylthio)methyl]-5-[4-(trifluoromethyl)phenyl]-3-furyl}methyl)thio]-2-methylphenoxy}acetate Prepared from intermediates 4 and 56

Example 66

{4-[({2-[(isopropylthio)methyl]-5-[4-(trifluoromethyl)phenyl]-3-furyl}methyl)thio]-2-methylphenoxy}acetic acid
Prepared by hydrolysis of example 65
m/z (M−H)⁻=509
HPLC Rt=4.5 minutes

Example 67 ethyl{4-[({2-[(1H-benzimidazol-2-ylthio)methyl]-5-[4-(trifluoromethyl)phenyl]-3-furyl}methyl)thio]-2-methylphenoxy}acetate Prepared from intermediates 4 and 61

Example 68

{4-[({2-{[(1H-benzimidazol-2-ylmethyl)thio]methyl}-5-[4-(trifluoromethyl)phenyl]-3-furyl}methyl)thio]-2-methylphenoxy}acetic acid
Prepared by hydrolysis of example 67
m/z (M−H)⁻=597
HPLC Rt=3.9 minutes

Example 69 ethyl{4-[({2-{[(3,5-dimethylphenyl)thio]methyl}-5-[4-(trifluoromethyl)phenyl]-3-furyl}methyl)thio]-2-methylphenoxy]acetate Prepared from intermediates 4 and 59

Example 70

{4-[({2-{[(3,5-dimethylphenyl)thio]methyl}-5-[4-(trifluoromethyl)phenyl]-3-furyl}methyl)thio]-2-methylphenoxy}acetic acid Prepared by hydrolysis of example 69
m/z (M−H)⁻=571
HPLC Rt=4.8 minutes

Example 71 ethyl{4-[({2-{[(2,4-difluorophenyl)thio]methyl}-5-[4-(trifluoromethyl)phenyl]-3-furyl}methyl)thio]-2-methylphenoxy}acetate Prepared from intermediates 4 and 60

Example 72

{4-[({2-{[(2,4-difluorophenyl)thio]methyl}-5-[4-(trifluoromethyl)phenyl]-3-furyl}methyl)thio]-2-methylphenoxy}acetic acid Prepared by hydrolysis of example 71
m/z (M−H)⁻=579
HPLC Rt=4.6 minutes

Example 73 ethyl{4-[({2-{[(2-furylmethyl)thio]methyl}-5-[4-(trifluoromethyl)phenyl]-3-furyl}methyl)thio]-2-methylphenoxy}acetate Prepared from intermediates 4 and 58

Example 74

{4-[({2-{[(2-furylmethyl)thio]methyl}-5-[4-(trifluoromethyl)phenyl]-3 furyl}methyl)thio]-2-methylphenoxy}acetic acid Prepared by hydrolysis of example 73
m/z (M−H)⁻=547
HPLC Rt=4.5 minutes

Example 75 ethyl{4-[({2-[(benzylthio)methyl]-5-[4-(trifluoromethyl)phenyl]-3-furyl}methyl)thio]-2-methylphenoxy}acetate Prepared from intermediates 4 and 54

Example 76

{4-[({3-[(benzylthio)methyl]-5-[4-(trifluoromethyl)phenyl]thien-2-yl}methyl)thio]-2-methylphenoxy}acetic acid Prepared by hydrolysis of example 75
m/z (M−H)⁻=557
HPLC Rt=4.6 minutes

Example 77 ethyl{4-[({2-{[isopropyl(methyl)amino]methyl}-5-[4-(trifluoromethyl)phenyl]-3-furyl}methyl)thio]-2-methylphenoxy}acetate Prepared from intermediates 4 and intermediate 88.

Example 78

{4-[({2-{[isopropyl(methyl)amino]methyl}-5-[4-(trifluoromethyl)phenyl]-3-furyl}methyl)thio]-2-methylphenoxy}acetic acid Prepared by hydrolysis of example 77
m/z (M−H)⁻=506
HPLC Rt=3.2 minutes

Example 79 ethyl{2-methyl-4-[({2-(phenoxymethyl)-5-[4-(trifluoromethyl)phenyl]-3-furyl}methyl)thio]phenoxy}acetate Prepared from intermediates 4 and 55

Example 80

{2-methyl-4-[({2-(phenoxymethyl)-5-[4-(trifluoromethyl)phenyl]-3-furyl}methyl)thio]phenoxy}acetic acid Prepared by hydrolysis of example 79
m/z (M−H)⁻=527
HPLC Rt=4.5 minutes

Example 81 ethyl{2-methyl-4-[({2-{[methyl(phenyl)amino]methyl}-5-[4-(trifluoromethyl)phenyl]-3-furyl}methyl)thio]phenoxy}acetate Prepared from intermediates 4 and 57

Example 82

{2-methyl- 4-[({2-{[methyl(phenyl)amino]methyl}-5-[4-(trifluoromethyl)phenyl]-3-furyl}methyl)thio]phenoxy}acetic acid Prepared by hydrolysis of example 81
m/z (M−H)⁻=540
HPLC Rt=4.7 minutes

Example 83 ethyl{4-[({2-isobutyl-5-[4-(trifluoromethyl)phenyl]-3-furyl}methyl)thio]-2-methylphenoxy}acetate Prepared from intermediates 4 and 68

Example 84

{4-[({2-isobutyl-5-[4-(trifluoromethyl)phenyl]-3-furyl}methyl)thio]-2-methylphenoxy}acetic acid Prepared by hydrolysis of example 83
m/z (M−H)⁻=477
HPLC Rt=4.7 minutes

Example 85 ethyl{2-methyl-4-[({2-[2-4-methylphenyl)ethyl]-5-[4-(trifluoromethyl)phenyl]-3-furyl}methyl)thio]phenoxy}acetate Prepared from intermediates 4 and 66

Example 86

{2-methyl-4-[({2-[2-(4-methylphenyl)ethyl]-5-[4-(trifluoromethyl)phenyl]-3-furyl}methyl)thio]phenoxy}acetic acid Prepared by hydrolysis of example 85
m/z (M−H)⁻=539
HPLC Rt=4.8 minutes

Example 87 ethyl{4-[({2-isopentyl-5-[4-(trifluoromethyl)phenyl]-3-furyl}methyl)thio]-2-methylphenoxy}acetate Prepared from intermediates 4 and 67

Example 88

{4-[({2-isopentyl-5-[4-(trifluoromethyl)phenyl]-3-furyl}methyl)thio]-2-methylphenoxy}acetic acid Prepared by hydrolysis of example 87
m/z (M−H)⁻=491
HPLC Rt=4.8 minutes

Example 89 ethyl{2-methyl-4-[({2-{[methyl(2-phenylethyl)amino]methyl}-5-[4-(trifluoromethyl)phenyl]-3-furyl}methyl)thio]phenoxy}acetate Prepared from intermediates 4 and intermediate 89

Example 90

{2-methyl-4-[({2-{[methyl(2-phenylethyl)amino]methyl}-5-[4-trifluoromethyl)phenyl]-3-furyl}methyl)thio]phenoxy}acetic acid hydrochloride Prepared by hydrolysis of example 89
m/z (M−H)⁻=568
HPLC Rt=3.5 minutes

Example 91 ethyl{2-methyl-4-[({2-{[methyl(pyridin-3-ylmethyl)amino]methyl}-5-[4-(trifluoromethyl)phenyl]-3-furyl}methyl)thio]phenoxy}acetate Prepared from intermediates 4 and 92

Example 92

{2-methyl -4-[({2-{[methyl(pyridin-3-ylmethyl)amino]methyl}-5-[4-(trifluoromethyl)phenyl]-3-furyl}methyl)thio]phenoxy}acetic acid hydrochloride Prepared by hydrolysis of example 91
m/z (M−H)⁻=555
HPLC Rt=3.3 minutes

Example 93 ethyl{4-[({2-{[(3,5-dimethoxybenzyl)(methyl)amino]methyl}-5-[4-(trifluoromethyl)phenyl]-3-furyl}methyl)thio]-2-methylphenoxy}acetate Prepared from intermediates 4 and intermediate 91

Example 94

{4-[({2-{[(3,5-dimethoxybenzyl)(methyl)amino]methyl}-5-[4-(trifluoromethyl)phenyl]-3-furyl}methyl)thio]-2-methylphenoxy}acetic acid Prepared by hydrolysis of example 93
m/z (M−H)⁻=614
HPLC Rt=3.5 minutes

Example 95 ethyl{4-[({4-{[cyclohexyl(methyl)amino]methyl}-5-[4-(trifluoromethyl)phenyl]-3-furyl}methyl)thio]-2-methylphenoxy}acetate Prepared from intermediates 4 and intermediate 90

Example 96

{4-[({2-{[cyclohexyl(methyl)amino]methyl}-5-[4-(trifluoromethyl)phenyl]-3-furyl}methyl)thio]-2-methylphenoxy}acetic acid hydrochloride Prepared by hydrolysis of example 95
m/z (M−H)⁻=46
HPLC Rt=3.4 minutes

Example 97 ethyl{4-[({3-[(isopropylthio)methyl]-5-[4-(trifluoromethyl)phenyl]thien-2-yl}methyl)thio]-2-methylphenoxy}acetate Prepared from intermediates 4 and 48

Example 98

{4-[({3-[(isopropylthio)methyl]-5-[4-(trifluoromethyl)phenyl]thien-2-yl}methyl)thio]-2-methylphenoxy}acetic acid Prepared by hydrolysis of example 97
m/z (M−H)⁻=525
HPLC Rt=4.7 minutes

Example 99 ethyl{2-methyl-4-[({3-phenoxymethyl)-5-[4-(trifluoromethyl)phenyl]thien-2-yl}methyl)thio]phenoxy}acetate Prepared from intermediates 4 and 47

Example 100

{2-methyl 4-[({3-(phenoxymethyl)-5-[4-(trifluoromethyl)phenyl]thien-2-yl}methyl)thio]phenoxy}acetic acid Prepared by hydrolysis of example 99
m/z (M−H)⁻=543
HPLC Rt=4.6 minutes

Example 101 ethyl{4-[({3-[(benzylthio)methyl]-5-[4-trifluoromethyl)phenyl]thien-2-yl}methyl)thio]-2-methylphenoxy}acetate Prepared from intermediates 4 and 46

Example 102

{4-[({3-[(benzylthio)methyl]-5-[4-(trifluoromethyl)phenyl]thien-2-yl}methyl)thio]-2-methylphenoxy}acetic acid Prepared by hydrolysis of example 101
m/z (M−H)⁻=573
HPLC Rt=4.7 minutes

Example 103 ethyl{2-methyl-4-[({3-{[4-(trifluoromethyl)phenoxy]methyl}-5-[4-(trifluoromethyl)phenyl]thien-2-yl}methyl)thio]phenoxy}acetate Prepared from intermediates 4 and 51

Example 104

{2-methyl-4-[({3-{[4-(trifluoromethyl)phenoxy]methyl}-5-[4-(trifluoromethyl)phenyl]thien-2-yl}methyl)thio]phenoxy}acetic acid Prepared by hydrolysis of example 103
m/z (M−H)⁻=61 1
HPLC Rt=4.5 minutes

Example 105 ethyl{2-methyl-4-[({3-{[4-(2-phenylethyl)phenoxy]methyl}-5-[4-(trifluoromethyl)phenyl]thien-2-yl}methyl)thio]phenoxy}acetate Prepared from intermediates 4 and 52

Example 106

{2-methyl-4-[({3-{[4-2-phenylethyl)phenoxy]methyl}-5-[4-(trifluoromethyl)phenyl]thien-2-yl}methyl)thio]phenoxy}acetic acid Prepared by hydrolysis of example 105
m/z (M−H)⁻=648
HPLC Rt=4.80 minutes

Example 107 ethyl{2-methyl-4-[({3-{[(4'-methyl-1,1'-biphenyl-4-yl)oxy]methyl}-5-[4-(trifluoromethyl)phenyl]thien-2-yl}methyl)thio]phenoxy}acetate Prepared from intermediates 4 and 49:

Example 108

{2-methyl-4-[({3-{[(4'-methyl-1,1'-biphenyl-4-yl)oxy]methyl}-5-[4-(trifluoromethyl)phenyl]thien-2-yl}methyl)thio]phenoxy}acetic acid Prepared by hydrolysis of example 107
m/z (M−H)⁻=633
HPLC Rt=4.8 minutes

Example 109 ethyl{2-methyl-4-[({3-{[methyl(phenyl)amino]methyl}-5-[4-(trifluoromethyl)phenyl]thien-2-yl}methyl)thio]phenoxy}acetate Prepared from intermediates 4 and 50

Example 110

{2-methyl-4-[({3-{[methyl(phenyl)amino]methyl}-5-[4-(trifluoromethyl)phenyl]thien-2-yl}methyl)thio]phenoxy}acetic acid Prepared by hydrolysis of example 109
m/z (M−H)⁻=556
HPLC Rt=4.6 minutes

Example 111 ethyl{4-[({-ethyl-5-[4-(trifluoromethyl)phenyl]thien-2-yl}methyl)thio]-2-methylphenoxy}acetate Prepared from intermediates 4 and 53

Example 112

{4-[({3-ethyl-5-[4-(trifluoromethyl)phenyl]thien-2-yl}methyl)thio]-2-methylphenoxy}acetic acid Prepared by hydrolysis of example 111
m/z (M−H)⁻=465
HPLC Rt=4.4 minutes

Example 113 ethyl[4-[({2-methyl-5-[4-(trifluoromethyl)phenyl]-3-furyl}methyl)thio]-2-(trifluoromethyl)phenoxy]acetate To a mixture of zinc powder (0.357 g) in ethyl acetate (8 ml), stirred at 60° C., was added ethyl[4-(chlorosulfonyl)-2-(trifluoromethyl)phenoxy]acetate (intermediate 3, 0.5419) in portions. The reaction mixture was heated until the sulfonyl chloride had been consumed, then dichlorodimethylsilane (0.378 ml) was added drop-wise. The reaction was stirred at reflux for 1 hour, then a solution of {2-methyl-5-[4-(trifluoromethyl)phenyl]-3-furyl}methanol (intermediate 24, 0.40 g) in ethyl acetate (2 ml) was added and heating continued for 18 hours. The reaction mixture was allowed to cool to room temperature, partitioned between brine and fresh ethyl acetate, dried over magnesium sulfate, concentrated under reduced pressure. The residue was purified using SPE (Si cartridge) using cyclohexane:ethyl acetate (40:1) as eluent to give the title compound as a pale brown gum.

¹H NMR (CDCl₃) δ 7.8 (d, 2H), 7.7 (d, 2H), 7.7 (d, 1H), 7.4 (d,d, 1H), 6.8 (d, 1H), 6.65 (s, 1H), 4.70 (s, 2H), 4.26 (q, 2H), 3.80 (s, 2H), 2.08 (s, 3H), 1.25 (t, 3H)

Example 114

[4-[({2-methyl-5-[4-(trifluoromethyl)phenyl]-3-furyl}methyl)thio]-2-(trifluoromethyl)phenoxy]acetic acid Prepared by hydrolysis of example 113
m/z (M−H)⁻=489
HPLC Rt=4.4 minutes
The following examples were prepared by an analogous method to that described for the preparation of example 113 and 114

Example 115 ethyl[4-[({-5-[4-chlorophenyl]-2-methyl-3-furyl}methyl)thio]-2-(trifluoromethyl)phenoxy]acetate Prepared from intermediates 3 and 32

Example 116

[4-({[5-(4-chlorophenyl)-2-methyl-3-furyl]methyl}thio)-2-(trifluoromethyl)phenoxy]acetic acid Prepared by hydrolysis of example 115
m/z (M−H)⁻=456
HPLC Rt=4.4 minutes

Example 117 ethyl(4-{2-[5-4-chlorophenyl)-2-methyl-3-furyl]ethenyl}-2-methylphenoxy)acetate

Sodium hydride (0.015 g, 60% dispersion in mineral oil) was added to anhydrous ethanol (5 ml) followed by [4-(2-ethoxy-2-oxoethoxy)-3-methylbenzyl](triphenyl)phosphonium chloride (intermediate 17, 0.17 g) after 10 minutes. After a further 10 minutes 5-(4-chlorophenyl)-2-methyl-3-furaldehyde (intermediate 71, 0.082 g) was added and the reaction mixture stirred at ambient temperature for 20 hours. The reaction mixture was treated with water and then the mixture extracted with chloroform. The chloroform solution was separated with a hydrophobic frit and the excess aldehyde removed using 3-[4 (hydrazinosulfonyl)phenyl]propionyl AM resin. The crude product remaining after this treatment was purified by Biotage® chromatography using a mixture of petroleum ether:ethyl acetate (9:1) as eluent to give the title compounds.

Example 118 ethyl(4-{2-[5-(4-chlorophenyl)-2-methyl-3-furyl]ethyl}-2-methylphenoxy)acetate

A mixture of ethyl(4-{2-[5-(4-chlorophenyl)-2-methyl-3-furyl]ethenyl}-2-methylphenoxy)acetate (intermediate 117, 0.070 g) and 10% palladium on carbon (0.070 g) in ethyl acetate (10 ml) was stirred under a hydrogen atmosphere for 2 hours. The reaction mixture was filtered through Celite™ and the filtrate evaporated. The residue was purified by SPE (Si cartridge) and sequentially using petroleum ether; petroleum ether:ethyl acetate (50:1); petroleum ether:ethyl acetate (25:1); petroleum ether:ethyl acetate (9:1) and petroleum ether:ethyl acetate (4:1) as eluents to give the title compound.

Example 119 sodium(4-{2-[5-(4-chlorophenyl)-2-methyl-3-furyl]ethyl}-2-methylphenoxy)acetate

Prepared by hydrolysis of example 118:
A mixture of ethyl(4-{2-[5-(4-chlorophenyl)-2-methyl-3-furyl]ethyl}-2-methylphenoxy)acetate (0.030 g) in 1,4-dioxan (1.5 ml) was treated with 0.5M aqueous sodium hydroxide (0.145 ml) and the reaction stirred at reflux for 5 hours. The solvent was removed to give a pale yellow solid which was triturated with ethyl acetate
m/z (M−H)⁻=383
HPLC Rt=4.70 minutes
The following examples were prepared by an analogous route to that described for the preparation of example 119 (i.e examples 117–119), where the sodium salt is isolated the above procedure is adopted. Where the free acid is isolated the hydrolysis procedure is as for example 2

Example 120

Ethyl[2-methyl-4-(2-{3-methyl-5-[4-(trifluoromethyl)phenyl]thien-2-yl}ethyl)phenoxy]acetate Prepared from intermediates 17 and 74

Example 121

[2-methyl-4-(2-{3-methyl-5-[4-(trifluoromethyl)phenyl]thien-2-yl}ethyl)phenoxy]acetic acid Prepared by hydrolysis of example 120
m/z (M−H)⁻=433
HPLC Rt=4.6 minutes

Example 122 ethyl[2-methyl-4-(2-{2-methyl-5-[4-(trifluoromethyl)phenyl]-3-furyl}ethyl)phenoxy]acetate Prepared from intermediates 17 and 72

Example 123

[2-methyl-4-(2-{2-methyl-5-[4-(trifluoromethyl)phenyl]-3-furyl}ethyl)phenoxy]acetic acid Prepared by hydrolysis of example 122
m/z (M−H)⁻=417
HPLC Rt=4.4 minutes

Example 124 ethyl(4-{2-[5-(4-chlorophenyl)-2-(trifluoromethyl)-3-furyl]ethyl}-2-methylphenoxy)acetate Prepared from intermediates 17 and 73

Example 125

Sodium(4-{2-[5-(4-chlorophenyl)-2-(trifluoromethyl)-3-furyl]ethyl}-2-methylphenoxy)acetate Prepared by hydrolysis of example 124
m/z (M–H)⁻=437
HPLC Rt=4.6 minutes

Example 126 methyl3-[4-(2-{3-methyl-5-[4-(trifluoromethyl)phenyl]thien-2-yl}ethyl)phenyl]propanoate Prepared from intermediate 74 [4-(2-ethoxy-2-oxoethoxy)benzyl](triphenyl)phosphonium bromide (C. G Morgan et al., Biochim. Biophys. Acta 1982, 692(2), 196–201)

Example 127

3-[4-(2-{3-methyl-5-[4-(trifluoromethyl)phenyl]thien-2-yl}ethyl)phenyl]propanoic acid Prepared by hydrolysis of example 126
m/z (M–H)⁻=418
HPLC Rt=4.3 minutes

Example 128 ethyl[2-tert-butyl-6-methyl-4-(2-{3-methyl-5-[4-(trifluoromethyl)phenyl]thien-2-yl}ethyl)phenoxy]acetate Prepared from intermediates 74 and 15

Example 129

[2-tert-butyl-6-methyl-4-(2-{3-methyl-5-[4-(trifluoromethyl)phenyl]thien-2-yl}ethyl)phenoxy]acetic acid Prepared by hydrolysis of example 128
m/z (M–H)⁻=490
HPLC Rt=4.7 minutes

Example 130 ethyl[2,6-dimethyl-4-(-2-{3-methyl-5-[4-(trifluoromethyl)phenyl]thien-2-yl}ethyl)phenoxy]acetate Prepared from intermediates 74 and 14

Example 131

[2,6-dimethyl-4-2-{3-methyl-5-[4-(trifluoromethyl)phenyl]thien-2-yl}ethyl)phenoxy]acetic acid Prepared by hydrolysis of example 130
m/z (M–H)⁻=448
HPLC Rt=4.7 minutes

Example 132 ethyl 3-[2-methyl-4-(2-{3-methyl-5-[4-(trifluoromethyl)phenyl]thien-2-yl}ethyl)phenyl]propanoate Prepared from intermediates 21 and 74

Example 133

3-[2-methyl-4-(2-{3-methyl-5-[4-(trifluoromethyl)phenyl]thien-2-yl}ethyl)phenyl]propanoic acid Prepared by hydrolysis of example 132
m/z (M–H)⁻=431
HPLC Rt=4.6 minutes

Example 134 ethyl 3-[2-methyl-4-(2-{2-methyl-5-[4-(trifluoromethyl)phenyl]-3-furyl}ethyl)phenyl]propanoate Prepared from intermediates 21 and 72

Example 135

3-[2-methyl-4-(2-{2-methyl-5-[4-(trifluoromethyl)phenyl]-3-furyl}ethyl)phenyl]propanoic acid Prepared by hydrolysis of example 134
m/z (M–H)⁻=433
HPLC Rt=4.3 minutes

Example 136

[2-methyl-4-({3-methyl-5-[4-(trifluoromethoxy)phenyl]thien-2-yl}methoxy)phenoxy]acetic acid A mixture of ethyl{4-[(5-bromo-3-methylthien-2-yl)methoxy]-2-methylphenoxy)acetate (intermediate 84, 0.20 g), 4-(trifluoromethoxy)benzeneboronic acid (0.11 g), tetrakis(triphenylphosphine)palladium (0) (0.04 g) and sodium carbonate (0.138 g) in ethylene glycol dimethylether (10 ml) and water (10 ml) were heated at reflux for 2 hours. The reaction mixture was concentrated and the residue partitioned between 2M hydrochloric acid and ethyl acetate and extracted thrice into ethyl acetate. The organic solutions were combined, dried with brine and over magnesium sulfate.

The product isolated after evaporation was further purified using SPE (aminopropyl) and using ethyl acetate; methanol; 10% acetic acid in methanol as eluents to give the title compound. Finally mass-directed autoprep was necessary to give the pure title compound as a white solid.
m/z (M–H)⁻=451
HPLC Rt=4.7 minutes The following example was prepared by an analogous method to that described for example 134

Example 137

[2-methyl-4-(2-{5-[4-(trifluoromethyl)phenyl]thien-2-yl}ethoxy)phenoxy]acetic acid Prepared from intermediate 70 and 4-trifluoromethylbenzene boronic acid
m/z (M–H)⁻=436
HPLC Rt=4.1 minutes

Example 138 ethyl[2-methyl-4-({3-methyl-5-[6-(trifluoromethyl) pyridin-3-yl]thien-2-yl}methoxy)phenoxy]acetate Prepared from intermediate 81 and 5-bromo-2-trifluoromethylpyridine using an analogous method used for the preparation of intermediate 78.
HPLC Rt4.2 minutes

Example 139

[2-methyl-4-({3-methyl-5-[6-(trifluoromethyl)pyridin-3-yl]thien-2-yl}methoxy)phenoxy]acetic acid Prepared by hydrolysis of example 138 m/z MH$^+$=466
HPLC Rt=4.1 minutes

Example 140 ethyl(4-{[5-5-chloropyridin-2-yl)-3-methylthien-2-yl]methoxy}-2-methylphenoxy)acetate Prepared from intermediate 81 and 2-bromo-5-chloropyridine using an analogous method used for the preparation of intermediate 78.

Example 141

{4-{[5-(5-chloropyridin-2-yl)-3-methylthien-2-yl]methoxy}-2-methylphenoxy}acetic acid Prepared by hydrolysis of example 140
m/z MH$^+$=402
HPLC Rt=4.1 minutes

Example 142

(4-{2-[5-(4-cyano-3-fluorophenyl)-3-methylthien-2-yl]ethyl}-2-methylphenoxy)acetic acid A mixture of 2-fluoro-4-[4-methyl-5-(2-{3-methyl-4-[(4-methyl-2,6,7-trioxabicyclo[2.2.2]oct-1-yl)methoxy]phenyl}ethyl)thien-2-yl]benzonitrile (intermediate 101, 0.016 g) in 2-propanol (2 ml) was treated with 2M aqueous hydrochloric acid (1 ml) and the mixture stirred at reflux for 2 hours. The solvent was removed and the residue dissolved in 1,4-dioxane (2 ml) and water (1 ml). This mixture was treated with 2M aqueous sodium hydroxide (0.5 ml) and the mixture stirred for 16 hours). The solvent was removed and the residue purified by SPE (aminopropyl). The title compound, as the free acid, was recovered by treating a solution of this product with Dowex H$^+$.
m/z (M–H)$^-$=408
HPLC Rt=4.3 minutes

Example 143 ethyl[4-(1,1-dimethyl-2-{3-methyl-5-[4-(trifluoromethyl)phenyl]thien-2-yl}ethyl)-2-methylphenoxy]acetate To a reactivial containing ethyl[4-(1,1-dimethyl-2-{3-methyl-5-[4-(trifluoromethyl)phenyl]thien-2-yl}-2-oxoethyl)-2-methylphenoxy]acetate (intermediate 106, 36 mg) was added trifluoroacetic acid (0.22 ml) and triethylsilane (0.11 ml). The vial was then sealed and heated at 50° C. for 18 hours. The reaction was then allowed to cool to room and concentrated in vacuo. Purification by flash column chromatography eluting cyclohexane-1% EtOAc/cyclohexane yielded the title compound as a colourless oil.
HPLC Rt=4.5 minutes
m/z (MNH$_4^+$) 508

Example 144

[4-1,1-dimethyl-2-{3-methyl-5-[4-(trifluoromethyl) phenyl]thien-2-yl}ethyl)-2-methylphenoxy]acetic acid To a solution of ethyl[4-(1,1-dimethyl-2-{3-methyl-5-[4-(trifluoromethyl)phenyl]thien-2-yl}ethyl)-2-methylphenoxy]acetate (Example 143, 0.03 g) in methanol (1 ml) and tetrahydrofuran (1 ml) was added 2M NaOH (0.5 ml). After 30 minutes stirring at room temperature the solvent was removed in vacuo. The residue was acidified with 2M HCl and the product extracted into dichloromethane, the organic extract was separated by hydrophobic frit and the solvent removed in vacuo, to yield the title compound as a colourless gum.
LCMS Rt=4.5 minutes
m/z (M–H)$^-$=461

Example 145

{2-ethyl-4-[({2-methyl-5-[4-(trifluoromethyl)phenyl]-3-furyl}methyl)thio]phenoxy}acetic acid To a mixture of zinc (407 mg) in ethyl acetate (10 ml) stirred at 60° C. was added acetic acid (0.203 ml) followed by a solution of ethyl[4-(chlorosulfonyl)-2-ethylphenoxy] acetate (intermediate 111, 546 mg) in ethyl acetate. The reaction mixture was stirred 60° C. for 2 hours and then dichlorodimethylsilane (0.431 ml) was added drop-wise. After a further 90 minutes {2-methyl-5-[4-(trifluoromethyl) phenyl]-3-furyl}methanol (472 mg) was added and the reaction mixture stirred at reflux for 17 hours. The reaction mixture was diluted with ethyl acetate; extracted with water, saturated aqueous sodium bicarbonate, water and dried with brine and over sodium sulfate. An attempt was purify the crude material by Biotage® chromatography using 3:2 petroleum ether: ethyl acetate as eluent. The partially purified material (223 mg) was hydrolyzed in 1,4-dioxan (6 ml) using 0.5 M aqueous sodium hydroxide (1.86 ml) for 16 hours. The reaction mixture was neutralized with 50W×2-200 Dowex; evaporated and the residue purified by mass-directed autopreparative HPLC to give the title compound as a solid.
LCMS Rt=4.3 minutes
m/z (M–H)$^-$=449

Example 146

{2-isopropyl-4-[({2-methyl-5-[4-trifluoromethyl) phenyl]-3-furyl}methyl)thio]phenoxy}acetic acid The title compound was prepared using ethyl[4-(chlorosulfonyl)-2-isopropylphenoxy]acetate (intermediate 112) by a method analogous to that used for the preparation of {2-ethyl-4-[({2-methyl-5-[4-(trifluoromethyl)phenyl]-3-furyl)methyl)thio]phenoxy}acetic acid (example 145).
LCMS Rt=4.30 minutes
m/z (M–H)$^-$=463

Example 146

{2-chloro-4-[({2-methyl-5-[4-(trifluoromethyl)phenyl]-3-furyl}methyl)thio]phenoxy}acetic acid The title compound was prepared from ethyl[4-(chlorosulfonyl)-2-chlorophenoxy]acetate (intermediate 113) by a method analogous to that used for the preparation of {2-ethyl-4-[({2-methyl-5-[4-(trifluoromethyl)phenyl]-3-furyl}methyl)thio]phenoxy}acetic acid (example 145).
LCMS Rt=4.30 minutes
m/z (M–H)⁻=454

Example 147

{2-bromo-4-[({2-methyl-5-[4-(trifluoromethyl)phenyl]-3-furyl}methyl)thio]phenoxy}acetic acid The title compound was prepared from ethyl[4-(bromosulfonyl)-2-chlorophenoxy]acetate (intermediate 114) by a method analogous to that used for the preparation of {2-ethyl4-[({2-methyl-5-[4-(trifluoromethyl)phenyl]-3-furyl}methyl)thio]phenoxy}acetic acid (example 145).
LCMS Rt=4.20 minutes
m/z (M–H)⁻=502

Example 148 ethyl{2-methyl-4-[({3-methyl-5-[4-(trifluoromethoxy)phenyl]thien-2-yl}methyl)thio]phenoxy}acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-mercapto-2-methylphenoxy)acetate (intermediate 4) and {3-methyl-5-[4-(trifluoromethoxy)phenyl]thien-2-yl}methanol (intermediate 118).
LCMS Rt=4.4 minutes
m/z (MH)⁺=497

Example 149

{2-methyl-4-[({3-methyl-5-[4-(trifluoromethoxy)phenyl]thien-2-yl}methyl)thio]phenoxy}acetic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl{2-methyl-4-[({3-methyl-5-[4-(trifluoromethoxy)phenyl]thien-2-yl}methyl)thio]phenoxy}acetate (example 148).
LCMS Rt=4.4 minutes
m/z (M–H)⁻=467

Example 150 ethyl[4-({5-[2,5-difluoro-4-(trifluoromethyl)phenyl]-3-methylthien-2-yl}methoxy)-2-methylphenoxy]acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and {5-[2,5-difluoro-4-(trifluoromethyl)phenyl]-3-methylthien-2-yl}methanol (intermediate 120).
LCMS Rt=4.3 minutes
m/z (MH)⁺=518

Example 151

[4-({5-[2,5-difluoro-4-(trifluoromethyl)phenyl]-3-methylthien-2-yl}methoxy)-2-methylphenoxy]acetic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[4-({5-[2,5-difluoro-4-(trifluoromethyl)phenyl]-3-methylthien-2-yl}methoxy)-2-methylphenoxy]acetate (example 150)
LCMS Rt=4.6 minutes
m/z (M–H)⁻=471

Example 152 ethyl[4-({5-[2,3-difluoro-4-(trifluoromethyl)phenyl]-3-methylthien-2-yl}methoxy)-2-methylphenoxy]acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and {5-[2,3-difluoro-4-(trifluoromethyl)phenyl]-3-methylthien-2-yl}methanol (intermediate 122).
LCMS Rt=4.3 minutes
m/z (MH)⁺=501

Example 153 ethyl[4-({5-[2,3-difluoro-4-(trifluoromethyl)phenyl]-3-methylthien-2-yl}methoxy)-2-methylphenoxy]acetate The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[4-({5-[2,3-difluoro-4-(trifluoromethyl)phenyl]-3-methylthien-2-yl}methoxy)-2-methylphenoxy]acetate (example 152).
LCMS Rt=4.6 minutes
m/z (M–H)⁻=471

Example 154 ethyl[4-({5-[2-fluoro-4-(trifluoromethyl)phenyl]-3-methylthien-2-yl}methoxy)-2-methylphenoxy]acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and {5-[2-fluoro-4-(trifluoromethyl)phenyl]-3-methylthien-2-yl}methanol (intermediate 124).
LCMS Rt=4.3 minutes
m/z (MNH)⁺=500

Example 155

[4-({5-[2-fluoro-4-(trifluoromethyl)phenyl]-3-methylthien-2-yl}methoxy)-2-methylphenoxy]acetate The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[4-({5-[2-fluoro-4-(trifluoromethyl)phenyl]-3-methylthien-2-yl}methoxy)-2-methylphenoxy]acetate (example 154).
LCMS Rt=4.3 minutes
m/z (M−H)⁻=453

Example 156 ethyl[2-methyl-4-(1-{5-[4-(trifluoromethyl)phenyl]thien-3-ylethoxy)phenoxy]acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and 1-{5-[4-(trifluoromethyl)phenyl]thien-3-yl}ethanol (intermediate 126).
LCMS Rt=4.2 minutes
m/z (MNH₄)⁺=482

Example 157

[2-methyl-4-(1-{5-[4-(trifluoromethyl)phenyl]thien-3-yl}ethoxy)phenoxy]acetic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[2-methyl-4-(1-{5-[4-(trifluoromethyl)phenyl]thien-3-yl}ethoxy)phenoxy]acetate (example 156).
LCMS Rt=4.1 minutes
m/z (M−H)⁻=435

Example 158 ethyl[2-methyl-4-(phenyl{5-[4-trifluoromethyl)phenyl]thien-3-yl}methoxy)phenoxy]acetate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and phenyl{5-[4-(trifluoromethyl)phenyl]thien-3-yl}methanol (intermediate 127).
LCMS Rt=4.3 minutes
m/z (MNH₄)⁺=544

Example 159

[2-methyl-4-(phenyl{5-[4-(trifluoromethyl)phenyl]thien-3-yl}methoxy)phenoxy]acetic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[2-methyl-4-(phenyl{5-[4-(trifluoromethyl)phenyl]thien-3-yl}methoxy)phenoxy]acetate (example 158).
LCMS Rt=4.3 minutes
m/z (M−H)⁻=497

Example 160 ethyl 2-methyl-2-[2-methyl-4-(phenyl{5-[4-(trifluoromethyl)phenyl]thien-3-yl}methoxy)phenoxy]propanoate The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl 2-(4-hydroxy-2-methylphenoxy)-2-methylpropanoate (intermediate 10) and phenyl{5-[4-(trifluoromethyl)phenyl]thien-3-yl}methanol (intermediate 127).
LCMS Rt=4.5 minutes
m/z (MNH₄)⁺=572

Example 161

2-methyl-2-[2-methyl-4-(phenyl{5-[4-(trifluoromethyl)phenyl]thien-3-yl}methoxy)phenoxy]propanoic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl 2-methyl-2-[2-methyl-4-(phenyl{5-[4-(trifluoromethyl)phenyl]thien-3-yl}methoxy)phenoxy]propanoate (example 160).
LCMS Rt=4.3 minutes
m/z (M−H)⁻=525

Example 162

Ethyl[2-methyl-4-(1-{3-methyl-5-[4-(trifluoromethyl)phenyl]thien-2-yl}ethoxy)phenoxy]acetic acid The title compound was prepared by a method analogous to that used for the preparation of ethyl{2-methyl-4-[({5-[4-(trifluoromethyl)phenyl]-3-furyl}methyl)thio]phenoxy}acetate (example 1) using ethyl(4-hydroxy-2-methylphenoxy)acetate (intermediate 7) and 1-{3-methyl-5-[4-(trifluoromethyl)phenyl]thien-2-yl}ethanol (intermediate 130).
LCMS Rt=4.4 minutes

Example 163

[2-methyl-4-(1-{3-methyl-5-[4-(trifluoromethyl)phenyl]thien-2-yl}ethoxy)phenoxy]acetic acid The title compound was prepared by using a method analogous to that used for the preparation of 2-methyl-4-[({5-[4-(trifluoromethyl)phenyl]-3-furyl}methyl)thio]phenoxy}acetic acid (example 2) using ethyl[2-methyl-4-(1-{3-methyl-5-[4-(trifluoromethyl)phenyl]thien-2-yl}ethoxy)phenoxy]acetic acid (example 162).
LCMS Rt=4.0 minutes
m/z (M−H)⁻=449

Examples 163–168 were prepared using intermediates 133–138 respectively by methods analogous to those described above for the preparation of example 63

Example 163 ethyl[4-({3-[(isopropylthio)methyl]-5-[4-trifluoromethyl)phenyl]thien-2-yl}methoxy)-2-methylphenoxy]acetate $R_f$=0.33 (chloroform)

Example 164 ethyl{2-methyl-4-[({5-[4-(trifluoromethyl)phenyl]-3-[(2,3,6-trimethylphenoxy)methyl]thien-2-yl}methyl)thio]phenoxy}acetate $R_f$=0.56 (chloroform)

Example 165 ethyl{4-[({3-{[(2-isopropyl-6-methylpyrimidin-4-yl)oxy]methyl}-5-[4-(trifluoromethyl)phenyl]thien-2-yl}methyl)thio]-2-methylphenoxy}acetate HPLC Rt=4.5 minutes
m/z MH$^+$=631

Example 166 ethyl{2-methyl-4-[({2-[(quinolin-2-ylthio)methyl]5-[4-(trifluoromethyl)phenyl]-3-furyl}methyl)thio]phenoxy}acetate HPLC Rt=4.7 minutes

Example 167 ethyl{2-methyl-4-[({2-4[{(3-phenyl-1H-1,2,4-triazol-5-yl)thio]methyl}-5-[4-(trifluoromethyl)phenyl]-3-furyl}methyl)thio]phenoxy}acetate HPLC Rt=4.4 minutes

Example 168 ethyl{4-[({2-{[4-(4-methoxyphenyl)piperazin-1-yl]methyl)-5-[4-(trifluoromethyl)phenyl]-3-furyl}methyl)thio]-2-methylphenoxy}acetate $^1$H NMR (CDCl3) δ 7.73 (d, 2 H), 7.62 (d, 2 H), 7.24 (d, 1 H), 7.16 (dd, 1 H), 6.85 (m, 4 H), 6.69 (s, 1 H), 6.60 (d, 1 H), 4.61 (s, 2 H), 4.25 (bs, 4 H)), 2.04 (s, 3H)), 1.28 (t, 3H)

Examples 169–174 were prepared using examples by hydrolysis of the ethyl esters (examples 163–168).

Example 169

[4-({13-[(isopropylthio)methyl]-5-[4-(trifluoromethyl)phenyl]thien-2-yl}methoxy)-2-methylphenoxy]acetic acid HPLC Rt=4.4 minutes
m/z (M–H)$^-$=509

Example 170

{2-methyl-4-[({5-[4-trifluoromethyl)phenyl]-3-[(2,3,6-trimethylphenoxy)methyl]thien-2-yl}methyl)thio]phenoxy}acetic acid HPLC Rt=4.7 minutes
m/z (M–H)$^-$=585

Example 171

{4-[({3-{[(2-isopropyl-6-methylpyrimidin-4-yl)oxy]methyl}-5-[4-(trifluoromethyl)phenyl]thien-2-yl}methyl)thio]-2-methylphenoxy}acetic acid HPLC Rt=4.6 minutes
m/z (M–H)$^-$=601

Example 172

{2-methyl-4-[({-2-[(quinolin-2-ylthio)methyl]-5-[4-(trifluoromethyl)phenyl]-3-furyl}methyl)thio]phenoxy}acetic acid HPLC Rt=4.7 minutes
m/z (M–H)-594

Example 173

{2-methyl-4-[({2-{[(3-phenyl-1H-1,2,4-triazol-5-yl)thio]methyl}-5-[4-(trifluoromethyl)phenyl]-3-furyl}methyl)thio]phenoxy}acetic acid HPLC Rt=4.3 minutes
m/z (M–H)$^-$=610

Example 174

{4-[({2-{[4-(4-methoxyphenyl)piperazin-1-yl]methyl}-5-[4-(trifluoromethyl)phenyl]-3-furyl}methyl)thio]-2-methylphenoxy}acetic acid HPLC Rt=3.6 minutes
m/z MH$^+$=625

The following intermediates and ligands were prepared for the binding and transfection assays described below:
The following intermediates and ligands were prepared for the binding and transfection assays described below:

(i) 2-{2-methyl-4-[({4-methyl-2-[4-trifluoromethyl)phenyl]-1,3-thiazol-5-yl}methyl)sulfanyl]phenoxy}acetic acid.

This compound was used as a PPARdelta reference in the transfection assays described below and was prepared according to the following method:

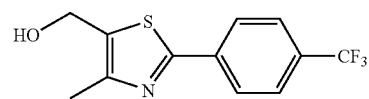

Intermediate 1

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH₂Cl₂ and THF. After evaporation, a yellow solid was obtained, that was crystallyzed from MeOH-water to afford intermediate 1 depicted above (9.90 g, 36 mmol, 90%) as a yellow solid mp 120–122° C.

Intermediate 2

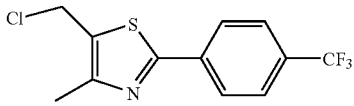

To a cold (0° C.) stirred solution of intermediate 1 (8.2 g, 30 mmol) and Et3N (6.07 g, 8.36 mL, 60 mmol), in dry CH₂Cl₂ (120 mL) was slowly added MeSO₂Cl (5.49 g, 3.71 mL, 48 mmol). After 2 hs at 0° C. more Et3N (6 mmol) and MeSO₂Cl (4.8 mmol) were added. After 2 more h a tic (hexane:EtOAc, 1:1) showed complete reaction. The reaction mixture was diluted with CH₂Cl₂ (120 mL) and washed with NaHCO₃ (sat.) (2×240 mL) and water (2×240 mL), dried, filtered and evaporated to afford intermediate 2 (8.0 g, 27 mmol, 90%) as a yellow solid.

Intermediate 3

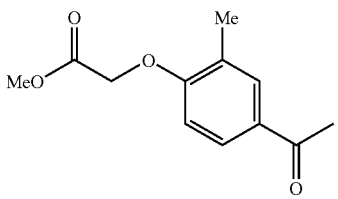

A mixture of methyl bromoacetate (3.80 g, 2.35 mL, 25.0 mmol), 4-hydroxy-3-methylacetophenone (4.13 g, 27.5 mmol), and Cs₂CO₃ (17.9 g, 55 mmol) in dry acetonitrile (125 mL) was stirred overnight at r.t. The mixture was filtered, washed with acetonitrile, and the solvent evaporated. The remaining syrup was redissolved in EtOAc (400 mL), washed with 1N NaOH (3×400 mL) and water (2×400 mL), dried, filtered, and evaporated to afford the pure title compound (5.50 g, 24.7 mmol, 99%) as a white solid.

Intermediate 4

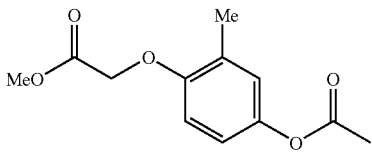

A solution of Intermediate 3 (5.33 g, 24 mmol), mCPBA (7.25 g, 42 mmol) and p-TsOH (480 mg) in dry dichloromethane (120 mL) was refluxed for 48 h. The reaction mixture was diluted with dichloromethane (120 mL), and successively washed with: aq. KI (2×200 mL), NaHSO₃ (2×200 mL), dried, filtered and evaporated to afford the title compound (5.0 g, 21 mmol, 87%) as a syrup.

Intermediate 5

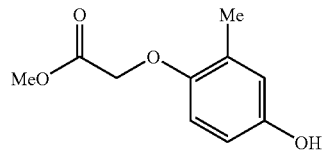

A solution of intermediate 4 (4.76 g, 20 mmol) in dry methanol (180 mL) was treated with a 0.5 N solution of NaOCH₃ in MeOH (40 mL, 20 mmol). After 1 h at r.t., the solution was neutralized with 1N HCl (20 mL). The solvent was evaporated, and the residue partitioned between dichloromethane (300 mL) and water (300 mL). The organic solution was separated, washed with water (300 mL), dried, filtered, and evaporated to afford the title compound (3.3 g, 16.8 mmol, 84%) as a brown solid.

Intermediate 6

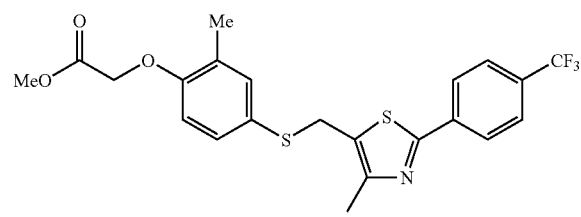

Intermediate 2 and intermediate 5 were coupled as in dry acetonitrile (5.0 mL) was stirred overnight at room temperature. The reaction mixture was diluted with CH₂Cl₂— (50 mL) and water (50 mL). The organic phase was separated and further washed with 1N NaOH (2×50 mL), and water (3×50 mL), dried, filtered, and evaporated to afford the final product (87%) as brown solid.

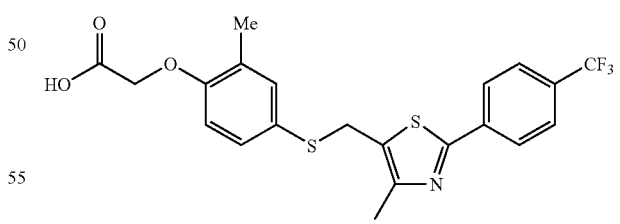

2-{2-methyl-4-[({4-methyl-2-[4-(trifluoromethyl)phenyl]-1,3-thiazol-5-yl}methyl)sulfanyl]phenoxy}acetic acid Intermediate 6 was hydrolyzed as described below. A solution of the corresponding ester (1 mmol) in THF (10 mL) (in some cases few drops of MeOH were added to help solubility), was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

The crude material was crystallized from MeOH:water to afford the title compound (60%) as yellow solid: mp 139–141° C.

Anal. Calcd. for $C_{21}H_{18}NO_3F_3S_2$: C, 55.62; H, 4.00; N, 3.09; S, 14.14. Found: C, 55.52; H, 4.11; N, 3.13; S, 14.29.

(ii) 2-methyl-2-[4-{[(4-methyl-2-[4-trifluoromethylphenyl]-thiazol-5-yl carbonyl)amino]methyl}-phenoxy]propionic acid.

This compound was used as a PPAR alpha reference in the transfection assay described below and was prepared according to the following method.

Intermediate A:

Same procedure as Stout, D. M. *J. Med. Chem.* 1983, 26(6), 808–13. To 4-methoxybenzyl amine (25 g, 0.18 mol; Aldrich) was added 46% HBr in $H_2O$ (106 ml, 0.9 mol; Aldrich). The reaction was refluxed overnight, then the reaction cooled to 0° C. and neutralized to pH7 slowly with KOH(s). The reaction is allowed to stir for ~30 min, then the solid filtered and dried. The solid redisolved in hot MeOH, filtered and the solution cooled to afford 19 g (85%) intermediate A.

$^1H$ NMR (DMSO-$d_6$): δ 8.0 (bs, 1H), 7.2 (d, 2H), 6.75 (d, 2H), 3.85 (s, 2H), 3.50 (bs, 2H).

Intermediate 2:

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent removed in vacuo. The final product (intermediate 2) was recrystallized from a minimum of MeOH to afford 40 g (59%) of final product as a white solid. $^1H$ NMR (CDCl$_3$): δ 8.10 (d, 2H), 7.70 (d, 2H), 4.40 (q, 2H), 2.80 (s, 3H), 1.4 (t, 3H).

Intermediate 3:

To intermediate 2 (1.84 g, 5.8 mmol) in THF was added 1N LiOH (6 mL, 6 mmol) and the reaction stirred at rt. After ~3 h, the reaction neutralized with 1N HCl, extracted 3×100 mL EtOAc, dried over Na$_2$SO$_4$, filtered and the solvent removed under vaccum to afford 1.5 g (89%) intermediate 3 as a white solid. $^1H$ NMR (DMSO-$d_6$): δ 13.55 (bs, 1H), 8.25 (d, 2H), 7.95 (d, 2H), 2.75 (s, 3H).

Intermediate 4:

To intermediate 3 (1 g, 7 mmol) in CH$_2$Cl$_2$/DMF (1:1) was added HOBT (565 mg, 4.2 mmol; Aldrich), EDC (800 mg, 4.2 mmol; Aldrich) and intermediate 1 (860 mg, 7 mmol). The reaction stirred at rt for 18 h. The solvent removed in vacuo, treated with H$_2$O and extracted 3×100 mL CH$_2$Cl$_2$. The organic phases combined and washed with 1N HCl, dried over Na$_2$SO$_4$, filtered and evaporated to afford a mixture (N-substituted and N,O-substituted). The mixture disolved in MeOH and treated with 1N NaOH. The reaction stirred 18 h at 50° C. The solvent removed in vacuo, dissolved in CH$_2$Cl$_2$, washed with H$_2$O, and dried over Na$_2$SO$_4$. The solvent evaporated the residue chromatographed (CH$_2$Cl$_2$/MeOH: 99/1) to afford 610 mg (47%) of intermediate 4 as a white solid. $^1H$ NMR (DMSO-$d_6$): δ 9.30 (s, 1H), 8.80 (t, 1H), 8.20 (d, 2H), 6.70 (d, 2H), 4.35 (d, 2H), 2.6 (s, 3H).

Intermediate 5:

2-methyl-2-[4-{[(4-methyl-2-[4-trifluoromethylphenyl] thiazol-5-ylcarbonyl)amino]methyl}phenoxy]propionic acid ethyl ester To intermediate 4 (710 mg, 1.81 mmol) in DMF (50 mL) was added the K$_2$CO$_3$ (275 mg, 1.99 mmol) followed by the ethyl 2-bromo-2-methylpropanate (280 μL, 1.91 mmol; Aldrich) and the reaction heated to 80° C. After 18 h, the reaction cooled to rt and the solvent removed in vacuo. The residue treated with water (200 mL), extracted 3×50 mL CH$_2$Cl$_2$, dried over Na$_2$SO$_4$, filtered and the solvent removed under vaccum. The residue was chromatographed (CH$_2$Cl$_2$/MeOH: 99/1). To afford 680 mg (77%) of Intermediate 5 as a clear oil. $^1H$ NMR(CDCl$_3$): δ 7.95 (d, 2H), 7.60 (d, 2H), 7.15 (d, 2H), 6.75 (d, 2H), 6.05 (t, 1H), 4.45 (d, 2H), 4.15 (q, 2H), 2.65 (s, 3H), 1.50 (s, 6H), 1.20 (t, 3H).

2-methyl-2-[4-{[(4-methyl-2-[trifluoromethylphenyl]-thiazol-5-ylcarbonyl)amino]methyl}phenoxy]propionic acid To Intermediate 5 (680 mg, 1.39 mmol) in MeOH was added 1N NaOH (1.6 mL, 1.6 mmol) and the reaction stirred at 60° C. After 18 h, the reaction cooled to rt and the solvent evaporated. The residue treated with 1N HCl, extracted 3×20 mL THF and the solvent removed under vacuum. 500 mg (75%) The title compound was precipitated as a white solid from a minimum CH$_2$Cl$_2$ and pentane. mp: changes the form between 60–70° C.; LC/MS (m/z): 477.22 (100%, AP–), 479.12 (100%, AP+); anal. C23H21F3N2O4S: C, 5.71 (57.73); H, 4.56 (4.42); N, 5.77 (5.85), S, 6.15 (6.70).

Binding Assay:

Compounds were tested for their ability to bind to hPPAR gamma hPPAR alpha, or PPAR delta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPAR gamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al. *Chem. Biol.* 1997, 4, 909–918. For the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent K$_I$ values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.* 1998, 257, 112–119).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor γ (PPARγ), *J. Biol. Chem.*, 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPAR gamma assay. The positive control in the hPPAR alpha assays was 2-methyl-2-[4-[(4-methyl-2-[4-trifluoromethylphenyl]-thiazol-5-yl-carbonyl)amino]methyl)phenoxy] propionic acid. The positive control for PPAR delta assays was 2-{2-methyl-4-[({4-methyl-2-{trifluoromethyl)phenyl]-1,3-thiazol-5-yl}methyl)sulfanyl]phenoxy}acetic acid.

What is claimed is:

1. A compound of formula (I) or pharmaceutically acceptable salts and solvates thereof,

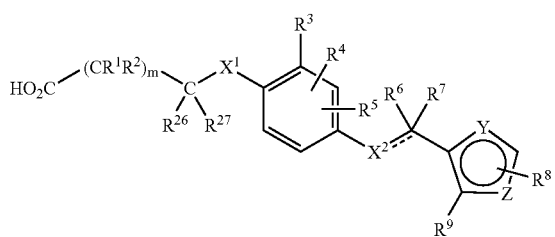

(I)

wherein
- $X^1$ is O, S, NH or NCH$_3$, C$_{1-3}$alkyl,
- $R^1$ and $R^2$ are independently H or C$_{1-3}$alkyl,
- $R^3$, $R^4$ and $R^5$ are independently H, CH$_3$, OCH$_3$, CF$_3$ or halogen;
- $R^{26}$ and $R^{27}$ are independently H, C$_{1-3}$ alkyl or an $R^{26}$ and $R^{27}$ may, together with the carbon atom to which they are bonded form a 3–5 membered cycloalkyl ring;
- m is 0–3;
- $X^2$ is $(CR^{10}R^{11})_n$, O, S, OCH$_2$;
- n=1 or 2;
- $R^6$, $R^7$, $R^{10}$ and $R^{11}$ independently represent H, F, C$_{1-6}$alkyl, phenyl or allyl or form a double bond as indicated by the depicted dashed line;
- one of Y and Z is CH, the other is S or O with the proviso that Y cannot be substituted and Z can only be substituted when it is carbon,
- $R^8$ is phenyl or pyridyl (wherein the N is in position 2 or 3) either of which may optionally be substituted by one or more halogen, CF$_3$, OCF$_3$, C$_{1-6}$ straight or branched alkyl with the provision that when $R^3$ is pyridyl, the N is unsubstituted,
- $R^9$ is C$_{1-4}$ alkyl, CF$_3$ or —CH$_2$D, wherein D is selected from:

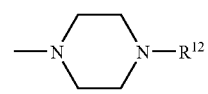

A wherein
$R^{12}$ is selected from the group consisting of moieties depicted below,

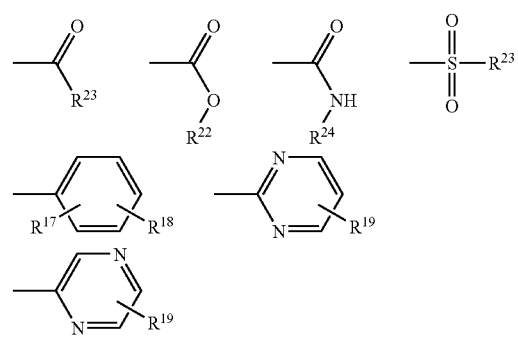

$R^{17}$ and $R^{18}$ are independently hydrogen C$_{1-6}$alkyl, C$_{1-6}$perfluoroalkyl, C$_{1-6}$acyl, —OC$_{1-6}$alkyl, perfluoroOC$_{1-6}$alkyl, or 1-hydroxyC$_{1-6}$alkyl;

$R^{19}$ is C$_{1-6}$alkyl;

$R^{22}$ is C$_{1-6}$alkyl, 6-memberedaryl, 5-membered heteroaryl, —C$_{1-6}$alkylenearyl;

$R^{23}$ is C$_{1-6}$alkyl, C$_{1-6}$cycloalkyl, 6-membered aryl or a 5-membered heteroaryl optionally substituted with one or two substituents selected from perfluroC$_{1-6}$alkyl, perfluroOC$_{1-6}$alkyl, C$_{1-6}$alkyl, —OC$_{1-6}$alkyl and —SC$_{1-6}$alkyl; and, $R^{24}$ is C$_{1-6}$alkyl, —C$_{1-6}$alkylenearylC$_{1-6}$alkylaryl, or a 6-membered aryl optionally substituted with one or two substituents selected from perfluroC$_{1-6}$alkyl, perfluroOC$_{1-6}$alkyl, C$_{1-6}$alkyl, —OC$_{1-6}$alkyl, and —SC$_{1-6}$alkyl;

B where Z is O, N or S (note that when Z is N, the depicted bond can be attached to the nitrogen in the ring as well as any of the carbons in the ring);

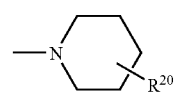

C $R^{20}$ is C$_{1-6}$alkyl, 6 membered aryl, —OC$_{1-6}$alkyl, hydroxy or 1-alkoxy C$_{1-6}$alkyl,

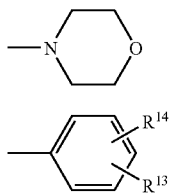

D

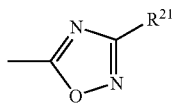

E where $R^{13}$ and $R^{14}$ are independently halogen, a 6-membered aryl or a 5-membered heteroaryl optionally substituted with one or two substituents selected from perfluro$C_{1-6}$alkyl, perfluroO$C_{1-6}$alkyl, $C_{1-6}$alkyl, —O$C_{1-6}$alkyl, and —S$C_{1-6}$alkyl;

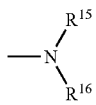

F $R^{21}$ is $C_{1-3}$-alkyl, —$C_{1-6}$alkylenephenyl, 6-membered aryl, optionally substituted with one or two substituents selected from CN, 5 or 6-membered heteroaryl, bicyclic aryl or bicyclic heteroaryl, perfluro$C_{1-6}$alkyl, perfluroO$C_{1-6}$alkyl, $C_{1-6}$alkyl, —O$C_{1-6}$alkyl and —S$C_{1-6}$alkyl,

G

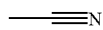

$R^{15}$ and $R^{16}$ are independently $C_{1-6}$alkyl, $C_{3-6}$cycloalkyl, $C_{0-6}$alkylene 6-membered aryl optionally substituted with 1 or 2 $C_{1-3}$alkyl or alkoxy groups, $C_{0-6}$alkylene 5-membered heteroaryl, pyridyl, bicyclic aryl or bicyclic heteroaryl or $R^{12}$ as defined above,

H

——≡N

I

——(CH$_2$)$_n$—$R^{28}$ wherein n is 1 or 3, $R^{28}$ is 6 membered aryl, 5 or 6 membered heteroaryl or bicyclic aryl or bicyclic heteroaryl.

J

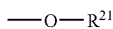

K

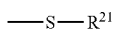

wherein $R^{21}$ is defined above.

2. A compound according to claim 1 wherein $R^{26}$ and $R^{27}$ are independently H or CH$_3$.

3. A compound according to claim 2 wherein $R^{26}$ and $R^{27}$ are both H.

4. A compound according to claim 1 wherein M is O.

5. A compound according to claim 1 wherein $X^1$ is O or S.

6. A compound according to claim 1 wherein $X^2$ is C($R^{10}R^{11}$)$_n$, O or S.

7. A compound according to claim 6 wherein n is 1.

8. A compound according to claim 1 wherein $R^6$, $R^7$, $R^{10}$ and $R^{11}$ are H.

9. A compound according to claim 1 wherein $R^8$ is phenyl optionally substituted by 1, 2, 3, 4, or 5 substituents independently selected from CH$_3$, OCH$_3$, CF$_3$, or halogen.

10. A compound according to claim 9 wherein the phenyl group is monosubstituted.

11. A compound according to claim 10 wherein the compound is monositued in the para position.

12. A compound according to claim 11 wherein the substituent is CF$_3$.

13. A compound according to claim 1 wherein $R^3$ is H, CH$_3$ or CF$_3$.

14. A compound according to claim 13 wherein $R^3$ is CH$_3$.

15. A compound according to claim 14 wherein $R^4$ and $R^5$ are H.

16. A compound according to claim 1 wherein $R^9$ is $C_{1-6}$alkyl, CF$_3$, CH$_2$D wherein D is selected from moieties G, H, I, J and K.

17. A compound according to claim 1 selected from:
{4-[({3-ethyl-5-[4-(trifluoromethyl)phenyl]thien-2-yl}methyl)thio]-2-methylphenoxy}acetic acid,
[4-({[5-(4-chlorophenyl)-2-(trifluoromethyl)-3-furyl]methyl}thio)-2-methylphenoxy]acetic acid,
[2-methyl-4-({3-methyl-5-[4-(trifluoromethyl)phenyl]thien-2-yl}methoxy)phenoxy]acetic acid,
{2-methyl-4-[({3-methyl-5-[4-(trifluoromethyl)phenyl]thien-2-yl}methyl)thio]phenoxy}acetic acid,
{2-methyl-4-[({2-methyl-5-[4-(trifluoromethyl)phenyl]-3-furyl}methyl)thio]phenoxy}acetic acid,
{2-ethyl-4-[({2-methyl-5-[4-(trifluoromethyl)phenyl]-3-furyl}methyl)thio]phenoxy}acetic acid,
{2-isopropyl-4-[({2-methyl-5-[4-(trifluoromethyl)phenyl]-3-furyl}methyl)thio]phenoxy}acetic acid,
[2-methyl-4-({3-methyl-5-[4-(trifluoromethoxy)phenyl]thien-2-yl}methoxy)phenoxy]acetic acid,
{4-[({2-[(benzylthio)methyl]-5-[4-(trifluoromethyl)phenyl]-3-furyl}methyl)thio]-2-methylphenoxy}acetic acid,
{2-methyl-4-[({3-methyl-5-[4-(trifluoromethyl)phenyl]-2-furyl}methyl)thio]phenoxy}acetic acid,
{2-methyl-4-[({3-methyl-4-[4-(trifluoromethyl)phenyl]thien-2-yl}methyl)thio]phenoxy}acetic acid,
[4-({[5-(4-chlorophenyl)-2-methyl-3-furyl]methyl}thio)-2-methylphenoxy]acetic acid,
{2-methyl-4-[({2-(trifluoromethyl)-5-[4-(trifluoromethyl)phenyl]-3-furyl}methyl)thio]phenoxy}acetic acid,
[2-methyl-4-(2-{4-methyl-2-[4-(trifluoromethyl)phenyl]-1,3-thiazol-5-yl)ethyl)phenoxy]acetic acid,
[2-methyl-4-(2-{3-methyl-5-[4-(trifluoromethyl)phenyl]thien-2-yl}ethyl)phenoxy]acetic acid,
(4-{2-[5-(4-chlorophenyl)-2-(trifluoromethyl)-3-furyl]ethyl}-2-methylphenoxy)acetic acid,
3-[4-({3-methyl-5-[4-(trifluoromethyl)phenyl]thien-2-yl}methoxy)phenyl]propanoic acid,
{2-methyl-4-[({3-(phenoxymethyl)-5-[4-(trifluoromethyl)phenyl]thien-2-yl}methyl)thio]phenoxy}acetic acid,
3-[2-methyl-4-[({3-methyl-5-[4-(trifluoromethyl)phenyl]thien-2-yl}methoxy)phenyl]propanoic acid, {4-[({2-[(benzylthio)methyl]-5-[4-(trifluoromethyl)phenyl]-3-furyl}methyl)thio]-2-methylphenoxy}acetic acid,
{4-[({2-[(isopropylthio)methyl]-5-[4-(trifluoromethyl)phenyl]-3-furyl}methyl)thio]-2-methylphenoxy}acetic acid,
{2-methyl-4-[({2-{[methyl(phenyl)amino]methyl}-5-[4-(trifluoromethyl)phenyl]-3-furyl}methyl)thio]phenoxy}acetic acid,
[2-methyl-4-(2-{2-methyl-5-[4-(trifluoromethyl)phenyl]-3-furyl}ethyl)phenoxy]acetic acid,
3-[2-methyl-4-(2-{3-methyl-5-[4-(trifluoromethyl)phenyl]thien-2-yl}ethyl)phenyl]propanoic acid,
[2-methyl-4-({2-methyl-5-[4-(trifluoromethyl)phenyl]thien-3-yl}methoxy)phenoxy]acetic acid,
{4-[({2-isopentyl-5-[4-(trifluoromethyl)phenyl]-3-furyl}methyl)thio]-2-methylphenoxy}acetic acid,
{2-methyl-4-[({2-methyl-5-[4-(trifluoromethyl)phenyl]thien-3-yl}methyl)thio]phenoxy}acetic acid,
[4-[({2-methyl-5-[4-(trifluoromethyl)phenyl]-3-furyl}methyl)thio]-2-(trifluoromethyl)phenoxy]acetic acid,
{2-methyl-4-[({5-[4-(trifluoromethyl)phenyl]-3-furyl}methyl)thio]phenoxy}acetic acid,
{2-methyl-4-[({5-[4-(trifluoromethyl)phenyl]-2-furyl}methyl)thio]phenoxy}acetic acid,
{2-methyl-4-[({5-[4-(trifluoromethyl)phenyl]thien-3-yl}methyl)thio]phenoxy}acetic acid,
{2-methyl-4-[({5-[4-(trifluoromethyl)phenyl]thien-2-yl}methyl)thio]phenoxy}acetic acid,
[4-({[5-(4-chlorophenyl)-2-(trifluoromethyl)-3-furyl]methyl}thio)-2-methylphenoxy]acetic acid,
(4-{[5-(4-chlorophenyl)-2-methyl-3-furyl]methoxy}-2-methylphenoxy)acetic acid,
[2-methyl-4-({2-(trifluoromethyl)-5-[4-(trifluoromethyl)phenyl]-3-furyl}methoxy)phenoxy]acetic acid,
[2-methyl-4-({2-methyl-5-[4-(trifluoromethyl)phenyl]-3-furyl}methoxy)phenoxy]acetic acid,
[2-methyl-4-({3-methyl-5-4-(trifluoromethyl)phenyl]-2-furyl}methoxy)phenoxy]acetic acid,
3-(4-{[5-(4-chlorophenyl)-2-(trifluoromethyl)-3-furyl]methoxy}phenyl)propanoic acid,
(4-{[5-(4-chlorophenyl)-2-(trifluoromethyl)-3-furyl]methoxy}2-methylphenoxy)acetic acid,
[4-({[5-(4-chlorophenyl)-2-methyl-3-furyl]methyl}thio)-2-(trifluoromethyl)phenoxy]acetic acid,
{4-[({3-[(isopropylthio)methyl]-5-[4-(trifluoromethyl)phenyl]thien-2-yl}methyl)thio]-2-methylphenoxy}acetic acid,
{4-[({3-[(benzylthio)methyl]-5-[4-(trifluoromethyl)phenyl]thien-2-yl}methyl)thio]-2-methylphenoxy}acetic acid,
3-(4-}[5-(4-chlorophenyl)-2-(trifluoromethyl)-3-furyl]methoxy}-2-methylphenyl)propanoic acid,
{2-methyl-4-[({2-(phenoxymethyl)-5-[4-(trifluoromethyl)phenyl]-3-furyl}methyl)thio]phenoxy}acetic acid,
3-[2-methyl-4-(2-{2-methyl-5-[4-(trifluoromethyl)phenyl]-3-furyl}ethyl)phenyl]propanoic acid,
{2-methyl-4-[({3-{[4-(trifluoromethyl)phenoxy]methyl}-5-[4-(trifluoromethyl)phenyl]thien-2-yl}methyl)thio]phenoxy}acetic acid,
{4-[({2-{[(2-furyl)methyl]thio]methyl}-5-[4-(trifluoromethyl)phenyl]-3-furyl}methyl)thio]-2-methylphenoxy}acetic acid,
{2-methyl-4-[({2-[2-(4-methylphenyl)ethyl]-5-[4-(trifluoromethyl)phenyl]-3-furyl}methyl)thio]phenoxy}acetic acid,
{4-[({2{[(2,4-difluorophenyl)thio]methyl}-5-[4-(trifluoromethyl)phenyl]-3-furyl}methyl)thio]-2-methylphenoxy}acetic acid,
{4-[({2-{[(3,5-dimethylphenyl)thio]methyl}-5-[4-(trifluoromethyl)phenyl]-3-furyl}methyl)thio]-2-methylphenoxy}acetic acid,
{4-[({2{[(4-tert-butylphenyl)thio]methyl}-5-[4-(trifluoromethyl)phenyl]-3-furyl}methyl)thio]-2-methylphenoxy}acetic acid,
{2-methyl-4-[({3-{[methyl(phenyl)amino]methyl}-5-[4-(trifluoromethyl)phenyl]thien-2-yl}methyl)thio]phenoxy}acetic acid,
{2-methyl-4-[({2-(2-pyridin-4-ylethyl)-5-[4-(trifluoromethyl)phenyl]-3-furyl}methyl)thio]phenoxy}acetic acid hydrochloride,
{4-[({2-isobutyl-5-[4-(trifluoromethyl)phenyl]-3-furyl}methyl)thio]-2-methylphenoxy}acetic acid,
{2-methyl-4-[({2-{[methyl(pyridin-3-ylmethyl)amino]methyl}-5-[4-(trifluoromethyl)phenyl]-3-furyl}methyl)thio]phenoxy}acetic acid hydrochloride,
{4-[({2-{[cyclohexyl(methyl)amino]methyl}-5-[4-(trifluoromethyl)phenyl]-3-furyl}methyl)thio]-2-methylphenoxy}acetic acid hydrochloride,
{2-methyl-4-[({2-{[methyl(2-phenylethyl)amino]methyl}-5-[4-(trifluoromethyl)phenyl]-3-furyl}methyl)thio]phenoxy}acetic acid hydrochloride,
[2-methyl-4-(1-{3-methyl-5-[4-(trifluoromethyl)phenyl]thien-2-yl}ethoxy)phenoxy]acetic acid,
[4-({3-[(isopropylthio)methyl]-5-[4-(trifluoromethyl)phenyl]thien-2-yl}methoxy)-2-methylphenoxy]acetic acid,
[2-methyl-4-(1-{5-[4-(trifluoromethyl)phenyl]thien-2-yl}ethoxy)phenoxy]acetic acid,
[2-methyl-4-(1-{5-[4-(trifluoromethyl)phenyl]thien-3-yl}ethoxy)phenoxy]acetic acid,
[2-methyl-4-(phenyl{5-[4-(trifluoromethyl)phenyl]thien-3-yl}methoxy)phenoxy]acetic acid,
2-methyl-2-[2-methyl-4-(phenyl{5-[4-(trifluoromethyl)phenyl]thien-3-yl}methoxy)phenoxy]propanoic acid,
{2-methyl-4-[({3-methyl-5-[4-(trifluoromethoxy)phenyl]thien-2-yl}methyl)thio]phenoxy}acetic acid,
[4-({5-[2,5-difluoro-4-(trifluoromethyl)phenyl]-3-methylthien-2-yl}methoxy)-2-methylphenoxy]acetic acid,
[4-({5-[2,3-difluoro-4-(trifluoromethyl)phenyl]-3-methylthien-2-yl}methoxy)-2-methylphenoxy]acetic acid,
[2-methyl-4-({3-methyl-5-[4-(1,1,2,2-tetrafluoroethoxy)phenyl]thien-2-yl}methoxy)phenoxy]acetic acid,
[4-({5-[2-fluoro-4-(trifluoromethyl)phenyl]-3-methylthien-2-yl}methoxy)-2-methylphenoxy]acetic acid.

18. A compound according to claim 1 selected from:
{2-methyl-4-[({3-methyl-5-[4-(trifluoromethyl)phenyl]-2-furyl}methyl)thio]phenoxy}acetic acid
{2-methyl-4-[({3-methyl-4-[4-(trifluoromethyl)phenyl]thien-2-yl}methyl)thio]phenoxy}acetic acid
[4-({[5-(4-chlorophenyl)-2-methyl-3-furyl]methyl}thio)-2-methylphenoxy]acetic acid,
{2-methyl-4-[({2-(trifluoromethyl)-5-[4-(trifluoromethyl)phenyl]-3-furyl}methyl)thio]phenoxy}acetic acid,
[2-methyl-4-(2-{4-methyl-2-[4-(trifluoromethyl)phenyl]-1,3-thiazol-5-yl}ethyl)phenoxy]acetic acid,
[2-methyl-4-(2-{3-methyl-5-[4-(trifluoromethyl)phenyl]thien-2-yl}ethyl)phenoxy]acetic acid, (4-{2-[5-(4-chlorophenyl)-2-(trifluoromethyl)-3-furyl]
 ethyl}-2-methylphenoxy)acetic acid,
3-[4-({3-methyl-5-[4-(trifluoromethyl)phenyl]thien-2-
 yl}methoxy)phenyl]propanoic acid,
{2-methyl-4-[({3-(phenoxymethyl)-5-[4-(trifluorom-
 ethyl)phenyl]thien-2-yl}methyl)thio]phenoxy}acetic
 acid,
3-[2-methyl-4-({3-methyl-5-[4-(trifluoromethyl)phenyl]
 thien-2-yl}methoxy)phenyl]propanoic acid,
{4-[({2-[(benzylthio)methyl]-5-[4-(trifluoromethyl)phe-
 nyl]-3-furyl}methyl)thio]-2-methylphenoxy}acetic
 acid,
{4-[({2-[(isopropylthio)methyl]-5-[4-(trifluoromethyl)
 phenyl]-3-furyl}methyl)thio]-2-methylphenoxy}acetic
 acid,
{2-methyl-4-[({2{[methyl(phenyl)amino]methyl}-5-[4-
 (trifluoromethyl)phenyl]-3-furyl}methyl)thio]
 phenoxy}acetic acid,
[2-methyl-4-(2-{2-methyl-5-[4-(trifluoromethyl)phenyl]-
 3-furyl}ethyl)phenoxy]acetic acid,
3-[2-methyl-4-(2-{3-methyl-5-[4-(trifluoromethyl)phe-
 nyl]thien-2-yl}ethyl)phenyl]propanoic acid,
[2-methyl-4-({2-methyl-5-[4-(trifluoromethyl)phenyl]
 thien-3-yl}methoxy)phenoxy]acetic acid,
{4-[({2-isopentyl-5-[4-(trifluoromethyl)phenyl]-3-
 furyl}methyl)thio]-2-methylphenoxy}acetic acid,
{2-methyl-4-[({2-methyl-5-[4-(trifluoromethyl)phenyl]
 thien-3-yl}methyl)thio]phenoxy}acetic acid,
[4-[({2-methyl-5-[4-(trifluoromethyl)phenyl]-3-
 furyl}methyl)thio]-2-(trifluoromethyl)phenoxy]acetic
 acid.

19. A compound according to claim 1 selected from:
{4-[({3-ethyl-5-[4-(trifluoromethyl)phenyl]thien-2-
 yl}methyl)thio]-2-methylphenoxy}acetic acid,
[4-({[5-(4-chlorophenyl)-2-(trifluoromethyl)-3-furyl]
 methyl}thio)-2-methylphenoxy]acetic acid,
[2-methyl-4-({3-methyl-5-[4-(trifluoromethyl)phenyl]
 thien-2-yl}methoxy)phenoxy]acetic acid,
{2-methyl-4-[({3-methyl-5-[4-(trifluoromethyl)phenyl]
 thien-2-yl}methyl)thio]phenoxy}acetic acid,
{2-methyl-4-[({2-methyl-5-[4-(trifluoromethyl)phenyl]-
 3-furyl}methyl)thio]phenoxy}acetic acid,
{2-ethyl-4-[({2-methyl-5-[4-(trifluoromethyl)phenyl]-3-
 furyl}methyl)thio]phenoxy}acetic acid,
{2-isopropyl-4-[({2-methyl-5-[4-(trifluoromethyl)phe-
 nyl]-3-furyl}methyl)thio]phenoxy}acetic acid,
[2-methyl-4-({3-methyl-5-[4-(trifluoromethoxy)phenyl]
 thien-2-yl}methoxy)phenoxy]acetic acid,
{4-[({2-[(benzylthio)methyl]-5-[4-(trifluoromethyl)phe-
 nyl]-3-furyl}methyl)thio]-2-methylphenoxy}acetic
 acid.

20. A pharmaceutical composition comprising a compound of any of claim 1.

21. A pharmaceutical composition according to claim 20 further comprising a pharmaceutically acceptable diluent or carrier.

22. A method of treatment of a hPPAR mediated disease or condition comprising administering a therapeutically effective amount of a compound according to any of claim 1 wherein the hPPAR mediated disease or condition id dyslipidemia, syndrome X, heart failure, hypercholesteremia, cardiovascular disease, type II diabetes mellitus type 1 diabetes, insulin resistance hyperlipidemia, obesity, anorexia bulimia, inflammation and anorexia nervosa.

* * * * *

UNITED STATES PATENT AND TRADEMARK OFFICE
CERTIFICATE OF CORRECTION

PATENT NO.       : 7,091,237 B2
APPLICATION NO.  : 10/476194
DATED            : August 15, 2006
INVENTOR(S)      : Beswick et al.

It is certified that error appears in the above-identified patent and that said Letters Patent is hereby corrected as shown below:

On the Title:

The chemical structure of Item (57) ABSTRACT should read as follows:

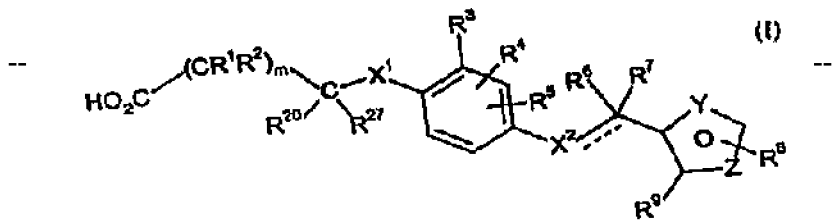

In the Claims:

Claim 1 (Column 84, Line 1) should read as follows:

-- $R^9$ is $C_{1-6}$ alkyl, $CF_3$ or $-CH_2D$, wherein D is selected --

Claim 1 (Column 84, Line 37) should read as follows:

-- $R^{23}$ is $C_{1-6}$alkyl, $C_{3-6}$cycloalkyl, 6-membered aryl or a --

Claim 22 (Column 90, Line 27-28) should read as follows:

-- effective amount of a compound according to claim 1 wherein the hPPAR mediated disease or condition is --

Signed and Sealed this

Twentieth Day of November, 2007

JON W. DUDAS
*Director of the United States Patent and Trademark Office*